United States Patent
Schweitzer et al.

(10) Patent No.: US 6,893,822 B2
(45) Date of Patent: May 17, 2005

(54) ENZYMATIC MODIFICATION OF A NUCLEIC ACID-SYNTHETIC BINDING UNIT CONJUGATE

(75) Inventors: Markus Schweitzer, Frankfurt am Main (DE); Richard R. Anderson, Encinitas, CA (US); Michael D. Fiechtner, Poway, CA (US); Jochen Müller, Diez (DE); Stefan Raddatz, Wiesbaden (DE); Christoph Brücher, Sulzbach (DE); Norbert Windhab, Hofheim am Taunus (DE); Jill M. Orwick, San Diego, CA (US); Eberhard Schneider, Kelkheim (DE); Marc Pignot, Bad Soden/Ts. (DE); Stefan Kienle, Frankfurt (DE)

(73) Assignee: Nanogen Recognomics GmbH, Frankfurt (DE)

( * ) Notice: Subject to any disclaimer, the term of this patent is extended or adjusted under 35 U.S.C. 154(b) by 0 days.

(21) Appl. No.: 09/910,469

(22) Filed: Jul. 19, 2001

(65) Prior Publication Data

US 2003/0175702 A1 Sep. 18, 2003

(51) Int. Cl.[7] ........................ C12Q 1/68; C12P 19/34; C07H 21/04
(52) U.S. Cl. .................... 435/6; 435/91.1; 435/91.2; 435/183; 536/23.1; 536/24.1; 536/25.1; 536/25.3; 536/26.6
(58) Field of Search ................. 435/6, 91.1, 91.2, 435/183; 536/23.1, 24.1, 25.1, 25.3, 26.6

(56) References Cited

U.S. PATENT DOCUMENTS

| 4,563,419 A | 1/1986 | Ranki et al. .............. 435/6 |
| 4,751,177 A | 6/1988 | Stabinsky ................. 435/6 |
| 4,787,963 A | 11/1988 | MacConnell ............. 204/450 |

(Continued)

FOREIGN PATENT DOCUMENTS

| EP | 0 305 145 A2 | 3/1989 |
| EP | 0 360 940 A2 | 4/1990 |
| EP | 0 360 940 B1 | 1/1996 |

(Continued)

OTHER PUBLICATIONS

Nelson et al "Addition of Homopolymers to the 3' ends of duplex DNa with terminal transferase" Methods in Enzymology, 197 68: 41–50.*

Beier, M. et al., "Chemical Etiology of Nucleic Acid Structure: Comparing Pentopyranosyl-(2'→4') Oligonucleotides with RNA", *Science*, vol. 283, pp. 699–703, Jan. 29, 1999.

Shchepinov, M.S. et al., "Oligonucleotide dendrimers: synthesis and use as polylabelled DNA probes", *Nucleic Acids Research*, vol. 25, No. 22, pp. 4447–4454, 1997.

(Continued)

*Primary Examiner*—Bj Forman
(74) *Attorney, Agent, or Firm*—O'Melveny & Myers LLP

(57) ABSTRACT

The present invention relates to conjugates of synthetic binding units and nucleic acids. The present invention also relates to methods for sorting and immobilizing nucleic acids on support materials using such conjugates by specific molecular addressing of the nucleic acids mediated by the synthetic binding systems. Particularly, the present invention also relates to novel methods of utilizing conjugates of synthetic binding units and nucleic acids to in active electronic array systems to produce novel array constructs from the conjugates, and the use of such constructs in various nucleic acid assay formats. In addition, the present invention relates to various novel forms of such conjugates, improved methods of making solid phase synthesized conjugates, and improved methods of conjugating pre-synthesized synthetic binding units and nucleic acids. The present invention also relates to the use of conjugates of synthetic binding units and nucleic acids as substrates for various enzymatic reactions, including nucleic acid amplification reactions.

84 Claims, 33 Drawing Sheets

U.S. PATENT DOCUMENTS

| | | | |
|---|---|---|---|
| 5,143,854 A | | 9/1992 | Pirrung et al. ............... 436/518 |
| 5,194,370 A | * | 3/1993 | Berninger et al. ............. 435/6 |
| 5,202,231 A | | 4/1993 | Drmanac et al. ............. 435/6 |
| 5,219,726 A | | 6/1993 | Evans ........................... 435/6 |
| 5,605,662 A | | 2/1997 | Heller et al. ............... 422/68.1 |
| 5,632,957 A | | 5/1997 | Heller et al. ............... 422/68.1 |
| 5,653,939 A | | 8/1997 | Hollis et al. ................... 422/50 |
| 5,695,940 A | | 12/1997 | Drmanac et al. ............. 435/6 |
| 5,744,305 A | | 4/1998 | Fodor et al. .................... 435/6 |
| 5,763,175 A | | 6/1998 | Brenner ......................... 435/6 |
| 5,876,924 A | * | 3/1999 | Zhang et al. ................... 435/5 |
| 6,051,380 A | | 4/2000 | Sosnowski et al. ............ 435/6 |
| 6,077,668 A | * | 6/2000 | Kool ............................. 435/6 |
| 6,399,302 B1 | * | 6/2002 | Lannigan et al. .............. 435/6 |

FOREIGN PATENT DOCUMENTS

| | | |
|---|---|---|
| GB | 2156074 | 10/1985 |
| JP | Hei 3-151900 | 6/1991 |
| WO | 86/03782 | 7/1986 |
| WO | 86/07387 | 12/1986 |
| WO | 89/10977 | 11/1989 |
| WO | 90/01564 | 2/1990 |
| WO | 93/13223 | 7/1993 |
| WO | 93/13225 | 7/1993 |
| WO | 93/25563 | 12/1993 |
| WO | 96/13522 | 5/1996 |
| WO | 97/32999 | 9/1997 |
| WO | 97/43232 | 11/1997 |
| WO | 98/25943 | 6/1998 |
| WO | 98/51819 | 11/1998 |
| WO | 99/15509 | 4/1999 |
| WO | 99/15539 | 4/1999 |
| WO | 99/15540 | 4/1999 |
| WO | 99/15541 | 4/1999 |
| WO | 99/15542 | 4/1999 |
| WO | 99/15893 | 4/1999 |
| WO | WO 00/4192 | 6/1999 |
| WO | 99/29711 | 6/1999 |
| WO | 99/42558 | 8/1999 |
| WO | 00/11011 | 3/2000 |
| WO | 00/39581 | 7/2000 |
| WO | 00/58516 | 10/2000 |
| WO | 00/60124 | 10/2000 |
| WO | 01/07657 A1 | 2/2001 |

OTHER PUBLICATIONS

Gilles, P.N. et al., "Single nucleotide polymorphic discrimination by an electronic dot blot assay on semiconductor microchips", Nature Biotechnology, vol. 17, pp. 365–370, Apr. 17, 1999.

Liu, J. et al., "Template–directed photoligation of oligodeoxyribonucleotides via 4–thiothymidine", Nucleic Acids Research, vol. 26, No. 13, pp. 3300–3304, 1998.

Green, N. M., "Advances in Protein Chemistry", pp. 85–132, 1975.

Chikoti, A., et al., "Molecular Origins of the Slow Streptavidin—Biotin Dissociation Kinetics", J. Am. Chem. Soc. vol. 117, pp. 10622–10628, 1995.

Chu, B.C.F. et al., "Ligation of oligonucleotides to nucleic acids or proteins via disulfide bonds", Nucleic Acids Research, vol. 16, No. 9, pp. 3671–3691, 1988.

Goodwin, J.T. et al., "Template–Directed Synthesis: Use of a Reversible Reaction", J. Am. Chem. Soc., vol. 114, pp. 9197–9198, 1992.

Gryaznov, S.M. et al., "Chemical Ligation of Oligonucleotides in the Presence and Absence of a Template", J. Am. Chem. Soc., vol. 115, pp. 3808–3809, 1993.

Uhlmann et al., "Antisense Oligonucleotides: A New Therapeutic Principle", Chemical Abstracts, vol. 90, No. 4, pp. 543–584, 1990.

Pitsch, S. et al., "147. Why Pentose– and Not Hexose–Nucleic Acids" Helv. Chim. Acta, vol. 76, pp. 2161–2183, 1993.

Pitsch, S. et al., "122. Pyranosyl–RNA ('p–RNA'): Base–Pairing Selectivity and Potential to Replicate", Helv. Chim. Acta, vol. 78, pp. 1621–1635, 1995.

Schlonvogt, I. et al., "188. Pyranosyl–RNA ('p–RNA'): NMR and Molecular–Dynamics Study of the Duplex Formed by Self–pairing of Ribopyranosyl–(C–G–A–A–T–T–C–G)" Helv. Chim. Acta, vol. 79, pp. 2316–2345, 1996.

Bolli, M. et al., "131. Pyranosyl–RNA: Further Observations on Replication", Helv. Chim. Acta, vol. 80, pp. 1901–1951, 1997.

Westin, L.. et al., "Antimicrobial Resistance and Bacterial Identification Utilizing a Microelectronic Chip Array", J. Clinical Microbiol., vol. 39, No. 3, pp. 1097–1104, 2001.

Anderson and Young, "Quantitative Filter Hybridization," Nucleic Acid Hybridization—A Practical Approach, Ed. B.D. Hames and S.J. Higgins (Washington, D.C. :IRL Press 1985) pp. 73–111.

Bains, "Setting a Sequence to Sequence a Sequence," Bio/Technology, 10:757–758 (1992).

Beattie et al., "Genosensor Technology," The 1992 San Diego Conference: Genetic Recognition, pp. 1–5 (Nov. 1992).

Beltz et al., "Isolation of Multigene Families and Determination of Homologies by Filter Hybridization Methods," Methods in Enzymology, 100:266–285 (1983).

Brady, A. et al., J.Chem.Soc., Perkin Trans., 1, 1997, pp. 3237–3253.

Cheng, J. et al., Nature/Biotechnology, 16, 6/98, pp. 541–546.

Chu, B.C.F. et al., "Ligation of oligonucleotides to nucleic acids or proteins via disulfide bonds", Nucleic Acids Research, vol. 16, No. 9, pp. 3671–3691, 1988.

Conner et al., "Detection of Sickle Cell [3]–Globin Allele by Hybridization With Synthetic Oligonucleotides," Proc. Natl. Acad. Sci. USA, 80:278–282 (1983).

Drmanac et al., "DNA Sequence Determination by Hybridization: A Strategy for Efficeint Large–Scale Sequencing," Science, 260: 1649–1652 (1993).

Drmanac et al., "Sequencing of Megabase Plus DNA by Hybridization: Theory of the Method," Genomics, 4:114–128 (1989).

Edman C.F. et al., Nucleic Acids Research, 25, 1997, 4907–4914.

Fodor et al., "Light–Directed, Spatially Addressable Parallel Chemical Synthesis," Science, 251:767–773 (1992).

Fodor et al., "Multiplexed Biochemical Assays With Biological Chips," Nature, 364:555–556 (1993).

Fredericks P.M., et al., Materials Characterization Using FT–IR Spectra. Part 2: Mathematical & Statistical Considerations, Applied Spectroscopy, 39, 2, 1989, p. 311.

Ghadiri, M. R. et al., Nature, 366, 1993, pp. 324–327.

Goodwin, J.T. et al., "Template–Directed Synthesis: Use of a Reversible Reaction", J. Am. Chem. Soc., vol. 114, pp. 9197–9198, 1992.

Guo Z. et al., Nucleic Acids Res, vol. 22, No. 24, 1994, pp. 5456–5464, Direct Fluorescence Analysis Of Genetic Polymorphism By Hybridization With Olognucleotide Arrays.

Hayakawa Y. et al, J.Am.Chem.Soc. 112, 1990, 1691.

Heller, M.J., IEEE Engineering in Medicine & Biology, Mar./Apr. 1996, 100–104 An Active Microelectronics Device For Multiplex DNA Analysis.

Huc, I., Lehn, J.M., Proc.Nat.Acad.Sci.USA, 94, 1997, pp. 2106–2110.

Kozal M.J. et al., Nature Medicine, vol. 2, No. 7, 1996, 753–759.

Lehn J.M., J.Chem.Soc. Chem. Commun., 49, 1990.

Malinowski E.R. et al, Factor Analysis In Chemistry, John Wiley & Sons, New York, 1980.

Marshall, A. et al, Nature Biotechnolgy, vol. 16, 1998, pp. 27–31.

Miculka, C. et al, European BioPharmaceutical Review, 6/98, pp. 52–57.

Ramsay, G., Nature Biotechnology, vol. 16, 1998, pp. 40–44.

Ranki et al., "Sandwich Hybridization as a Convenient Method for the Detection of Nucleic Acids in Crude Samples," *Gene,* 21:77–85 (1983).

Schlonvogt, I. et al., "188. Pyranosyl–RNA ('p–RNA'): NMR and Molecular–Dynamics Study of the Duplex Formed by Self–pairing of Ribopyranosyl–(C–G–A–A–T–T–C–G)" *Helv. Chim. Acta,* vol. 79, pp. 2316–2345, 1996.

Sosnowski R. et al., Proc. Natl.Acad.Sci, 94, 1997, 1119–1123.

Southern et al., "Analyzing and Comparing Nucleic Acid Sequences by Hybridization to Arrays of Oligonucleotides Evaluation Using Experimental Models," *Genomics,* 13:1008–1017 (1992).

Strezoska et al., "DNA Sequencing by Hybridization: 100 Bases Read by a Non–Gel Based Method", *Proc. Natl. Acad. Sci. USA,* 88:10089–93 (1991).

Taylor P. et al, Principles Of Drug Action–The Basis Of Pharmacology, edited by W.B. Pratt, P. Taylor, Third Edition, Churchill Livingston, 1990, pp. 1–74.

Wallace et al., "Hybridiation of Synthetic Oligodexribonucleotides to X174 DNA: The Effect of Single Base Pair Mismatch," *Nucleic Acid Res.,* 6:3543–3557 (1979).

Westin, L.. et al., "Antimicrobial Resistance and Bacterial Identification Utilizing a Microelectronic Chip Array", *J. Clinical Microbiol.,* vol. 39, No. 3, pp. 1097–1104, 2001.

Zhang, Y. et al, J.Am.Chem.Soc., 116, 1994, pp. 1661–1669.

Miculka et al., *European BioPharmaceutical Review,* pp. 52–54 and 57 pp. 55–56 missing pp. 58→end of the Article Missing (Jun. 1998).

* cited by examiner helical planar

A:

SAU

B:

E

Selective binding of SBS on SPR

Selective Binding of SBU and SAU on chip arrays

Immobilization of conjugates on SPR chips

Immobilization of conjugates on SPR chips and hybridization with complementary DNA

A

B

Addressing of SBU to SAU
SDA Primers on same or different SBU

Addressing of SBU to SAU
Both SDA primers on the same SBU

Phase 1: Initiation

A. Copying of target onto SBU anchored SDA primer

B. Displacement of genomic DNA by extension from bumper primer 1.

Phase 1: Initiation (continued)

C. Restriction site is activated in Primer 1.

D. Generate displaced S1 strands with target sequence

Phase 2: Linear Amplification via capture

A. One-for-one increase in anchored amplicon for every Phase 1 displaced strand captured B. Generation of single stranded anchored amplicons

Phase 3: Exponential Amplification via bridging and capture

A. Activate restriction site in both anchored Amplicon 1 and anchored Amplicon 2

B. Generate S1 and S2 displaced strands with restriction site on both ends

Phase 3: Exponential Amplification via bridging and capture (cont'd)

C. Establishes a link between displaced strand capture and activation of restriction site for
   nicking and strand displacement synthesis cycle

SEQUENCE LISTING

```
<160> NUMBER OF SEQ ID NOS: 184

<210> SEQ ID NO 1
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 1 aatgccta                                                              8

<210> SEQ ID NO 2
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 2 taggcatt                                                              8

<210> SEQ ID NO 3
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 3 aatcgcta                                                              8

<210> SEQ ID NO 4
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 4 tagcgatt                                                              8

<210> SEQ ID NO 5
<211> LENGTH: 8
<212> TYPE: DNA
<213> ORGANISM: Artificial sequence
```

```
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 5 aagtccta                                                                      8

<210> SEQ ID NO 6
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 6 taggactt                                                                      8

<210> SEQ ID NO 7
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 7 aatgtcca                                                                      8

<210> SEQ ID NO 8
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 8 tggacatt                                                                      8

<210> SEQ ID NO 9
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 9 aatccgta                                                                      8

<210> SEQ ID NO 10
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
```

```
<223> OTHER INFORMATION: pyranosyl RNA

<400> SEQUENCE: 10 tacggatt                                                                   8

<210> SEQ ID NO 11
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 11 aattcgca                                                                   8

<210> SEQ ID NO 12
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 12 tgcgaatt                                                                   8

<210> SEQ ID NO 13
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 13 aacgttca                                                                   8

<210> SEQ ID NO 14
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 14 tgaacgtt                                                                   8

<210> SEQ ID NO 15
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 15
```

-continued agtactca                                         8

<210> SEQ ID NO 16
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 16 tgagtact                                         8

<210> SEQ ID NO 17
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 17 aatctcga                                         8

<210> SEQ ID NO 18
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 18 tcgagatt                                         8

<210> SEQ ID NO 19
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 19 aagctcta                                         8

<210> SEQ ID NO 20
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 20 tagagctt                                         8

<210> SEQ ID NO 21

```
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 21 actagcta                                                                 8

<210> SEQ ID NO 22
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 22 tagctagt                                                                 8

<210> SEQ ID NO 23
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 23 aagttcca                                                                 8

<210> SEQ ID NO 24
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 24 tggaactt                                                                 8

<210> SEQ ID NO 25
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 25 aagcctta                                                                 8

<210> SEQ ID NO 26
<211> LENGTH: 8
<212> TYPE: DNA
<213> ORGANISM: Artificial sequence
<220> FEATURE:
```

-continued

```
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 26 taaggctt                                                                 8

<210> SEQ ID NO 27
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 27 atgaccta                                                                 8

<210> SEQ ID NO 28
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 28 taggtcat                                                                 8

<210> SEQ ID NO 29
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 29 aacgctta                                                                 8

<210> SEQ ID NO 30
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 30 taagcgtt                                                                 8

<210> SEQ ID NO 31
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA
```

```
<400> SEQUENCE: 31 actgacta                                                              8

<210> SEQ ID NO 32
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 32 tagtcagt                                                              8

<210> SEQ ID NO 33
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 33 aattgcca                                                              8

<210> SEQ ID NO 34
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 34 tggcaatt                                                              8

<210> SEQ ID NO 35
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 35 aaccgtta                                                              8

<210> SEQ ID NO 36
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 36 taacggtt                                                              8
```

<210> SEQ ID NO 37
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 37 agtcacta                                                                 8

<210> SEQ ID NO 38
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 38 tagtgact                                                                 8

<210> SEQ ID NO 39
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 39 aactgcta                                                                 8

<210> SEQ ID NO 40
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 40 tagcagtt                                                                 8

<210> SEQ ID NO 41
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 41 ctggcata                                                                 8

<210> SEQ ID NO 42
<211> LENGTH: 8

-continued

```
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 42 tatgccag                                                                8

<210> SEQ ID NO 43
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 43 ccagtcta                                                                8

<210> SEQ ID NO 44
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 44 tagactgg                                                                8

<210> SEQ ID NO 45
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 45 aatgcgta                                                                8

<210> SEQ ID NO 46
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 46 tacgcatt                                                                8

<210> SEQ ID NO 47
<211> LENGTH: 8
<212> TYPE: DNA
<213> ORGANISM: Artificial sequence
<220> FEATURE:
<223> OTHER INFORMATION: Synthetic binding system
```

```
<221> NAME/KEY: modified_base
<222> LOCATION: (1)..(8)
<223> OTHER INFORMATION: pyranosyl RNA

<400> SEQUENCE: 47 aatcctag                                                                 8

<210> SEQ ID NO 48
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(8)
<223> OTHER INFORMATION: pyranosyl RNA

<400> SEQUENCE: 48 ctaggatt                                                                 8

<210> SEQ ID NO 49
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(10)
<223> OTHER INFORMATION: pyranosyl RNA

<400> SEQUENCE: 49
tcctgcattc                                                              10

<210> SEQ ID NO 50
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(10)
<223> OTHER INFORMATION: pyranosyl RNA

<400> SEQUENCE: 50
gaatgcagga                                                              10

<210> SEQ ID NO 51
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(10)
<223> OTHER INFORMATION: pyranosyl RNA

<400> SEQUENCE: 51
ctctacgtct                                                              10

<210> SEQ ID NO 52
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(10)
<223> OTHER INFORMATION: pyranosyl RNA
```

```
<400> SEQUENCE: 52
agacgtagag                                                              10

<210> SEQ ID NO 53
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(10)
<223> OTHER INFORMATION: pyranosyl RNA

<400> SEQUENCE: 53
cctcgtactt                                                              10

<210> SEQ ID NO 54
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(10)
<223> OTHER INFORMATION: pyranosyl RNA

<400> SEQUENCE: 54
aagtacgagg                                                              10

<210> SEQ ID NO 55
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(10)
<223> OTHER INFORMATION: pyranosyl RNA

<400> SEQUENCE: 55
ttctgtatcc                                                              10

<210> SEQ ID NO 56
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(10)
<223> OTHER INFORMATION: pyranosyl RNA

<400> SEQUENCE: 56
ggatacagaa                                                              10

<210> SEQ ID NO 57
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(10)
<223> OTHER INFORMATION: pyranosyl RNA

<400> SEQUENCE: 57
ctttatgcct                                                              10
```

```
<210> SEQ ID NO 58
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(10)
<223> OTHER INFORMATION: pyranosyl RNA

<400> SEQUENCE: 58
aggcataaag                                                              10

<210> SEQ ID NO 59
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(10)
<223> OTHER INFORMATION: pyranosyl RNA

<400> SEQUENCE: 59
cccacttgtt                                                              10

<210> SEQ ID NO 60
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(10)
<223> OTHER INFORMATION: pyranosyl RNA

<400> SEQUENCE: 60
aacaagtggg                                                              10

<210> SEQ ID NO 61
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(10)
<223> OTHER INFORMATION: pyranosyl RNA

<400> SEQUENCE: 61
tctgctcatc                                                              10

<210> SEQ ID NO 62
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(10)
<223> OTHER INFORMATION: pyranosyl RNA

<400> SEQUENCE: 62
gatgagcaga                                                              10

<210> SEQ ID NO 63
<211> LENGTH: 10
<212> TYPE: DNA
```

```
<213> ORGANISM: Artificial sequence
<220> FEATURE:
<223> OTHER INFORMATION: Synthetic binding system
<221> NAME/KEY: modified_base
<222> LOCATION: (1)..(10)
<223> OTHER INFORMATION: pyranosyl RNA

<400> SEQUENCE: 63
ctcacctatt                                                          10

<210> SEQ ID NO 64
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(10)
<223> OTHER INFORMATION: pyranosyl RNA

<400> SEQUENCE: 64
aataggtgag                                                          10

<210> SEQ ID NO 65
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(10)
<223> OTHER INFORMATION: pyranosyl RNA

<400> SEQUENCE: 65
ttctatactc                                                          10

<210> SEQ ID NO 66
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(10)
<223> OTHER INFORMATION: pyranosyl RNA

<400> SEQUENCE: 66
gagtatagaa                                                          10

<210> SEQ ID NO 67
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(10)
<223> OTHER INFORMATION: pyranosyl RNA

<400> SEQUENCE: 67
tgtttgggtg                                                          10

<210> SEQ ID NO 68
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
```

<222> LOCATION: (1)..(10)
<223> OTHER INFORMATION: pyranosyl RNA

<400> SEQUENCE: 68
cacccaaaca                                                                                  10

<210> SEQ ID NO 69
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(10)
<223> OTHER INFORMATION: pyranosyl RNA

<400> SEQUENCE: 69
tggtcggttg                                                                                  10

<210> SEQ ID NO 70
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(10)
<223> OTHER INFORMATION: pyranosyl RNA

<400> SEQUENCE: 70
caaccgacca                                                                                  10

<210> SEQ ID NO 71
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(10)
<223> OTHER INFORMATION: pyranosyl RNA

<400> SEQUENCE: 71
tggttatctg                                                                                  10

<210> SEQ ID NO 72
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(10)
<223> OTHER INFORMATION: pyranosyl RNA

<400> SEQUENCE: 72
cagataacca                                                                                  10

<210> SEQ ID NO 73
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(10)
<223> OTHER INFORMATION: pyranosyl RNA

<400> SEQUENCE: 73

-continued

```
cgtgtatgta                                                    10

<210> SEQ ID NO 74
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(10)
<223> OTHER INFORMATION: pyranosyl RNA

<400> SEQUENCE: 74
tacatacacg                                                    10

<210> SEQ ID NO 75
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(10)
<223> OTHER INFORMATION: pyranosyl RNA

<400> SEQUENCE: 75
ctccatgttc                                                    10

<210> SEQ ID NO 76
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(10)
<223> OTHER INFORMATION: pyranosyl RNA

<400> SEQUENCE: 76
gaacatggag                                                    10

<210> SEQ ID NO 77
<211> LENGTH: 31
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(10)
<223> OTHER INFORMATION: pyranosyl RNA

<400> SEQUENCE: 77
tcctgcattc gcatagaggc agaataacag g                            31

<210> SEQ ID NO 78
<211> LENGTH: 31
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(10)
<223> OTHER INFORMATION: pyranosyl RNA

<400> SEQUENCE: 78
ctctacgtct gcatagaggc agaataacag g                            31
```

```
<210> SEQ ID NO 79
<211> LENGTH: 31
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(10)
<223> OTHER INFORMATION: pyranosyl RNA

<400> SEQUENCE: 79
cctcgtactt gcatagaggc agaataacag g                              31

<210> SEQ ID NO 80
<211> LENGTH: 34
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(10)
<223> OTHER INFORMATION:

<400> SEQUENCE: 80
tcctgcattc agaaatctca catggacatc ttca                           34

<210> SEQ ID NO 81
<211> LENGTH: 32
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(10)
<223> OTHER INFORMATION: pyranosyl RNA

<400> SEQUENCE: 81
tcctgcattc cctgggcttt gcagcacttc tc                             32

<210> SEQ ID NO 82
<211> LENGTH: 22
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (13)..(22)
<223> OTHER INFORMATION: pyranosyl RNA

<400> SEQUENCE: 82
ccccagtgct ggtcctgcat tc                                        22

<210> SEQ ID NO 83
<211> LENGTH: 40
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (31)..(40)
<223> OTHER INFORMATION: pyranosyl RNA

<400> SEQUENCE: 83
atgctaaagg acgtcattgc acaatcttaa ctctacgtct                     40

<210> SEQ ID NO 84
<211> LENGTH: 33
<212> TYPE: DNA
<213> ORGANISM: Artificial sequence
```

```
<220> FEATURE:
<223> OTHER INFORMATION: Synthetic binding system
<221> NAME/KEY: modified_base
<222> LOCATION: (24)..(33)
<223> OTHER INFORMATION: pyranosyl RNA

<400> SEQUENCE: 84
ggagtttgta catgcggtgg agccctcgta ctt                                    33

<210> SEQ ID NO 85
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(1)
<223> OTHER INFORMATION: 2'-O-methyl RNA
<221> NAME/KEY: modified_base
<222> LOCATION: (2)..(8)
<223> OTHER INFORMATION: pyranosyl RNA

<400> SEQUENCE: 85 ctaggatt                                                                 8

<210> SEQ ID NO 86
<211> LENGTH: 31
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (22)..(31)
<223> OTHER INFORMATION: pyranosyl RNA

<400> SEQUENCE: 86
ggacaataag acggagatac gcctcgtact t                                      31

<210> SEQ ID NO 87
<211> LENGTH: 13
<212> TYPE: DNA
<213> ORGANISM: Artificial sequence
<220> FEATURE:
<223> OTHER INFORMATION: Test nucleic acid sequence
<221> NAME/KEY: modified_base
<222> LOCATION: (13)..(13)
<223> OTHER INFORMATION: RNA

<400> SEQUENCE: 87
ccccagtgct ggu                                                          13

<210> SEQ ID NO 88
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (8)..(8)
<223> OTHER INFORMATION: CY3 dye
<221> NAME/KEY: modified_base
<222> LOCATION: (1)..(8)
<223> OTHER INFORMATION: pyranosyl RNA
<221> NAME/KEY: modified_base
<222> LOCATION: (1)..(1)
<223> OTHER INFORMATION: Hydrazide functional group

<400> SEQUENCE: 88 ttacggat                                                                 8
```

```
<210> SEQ ID NO 89
<211> LENGTH: 12
<212> TYPE: DNA
<213> ORGANISM: Artificial sequence
<220> FEATURE:
<223> OTHER INFORMATION: Test nucleic acid sequence
<221> NAME/KEY: modified_base
<222> LOCATION: (12)..(12)
<223> OTHER INFORMATION: Glyceryl moiety

<400> SEQUENCE: 89
ccccagtgct gg                                                            12

<210> SEQ ID NO 90
<211> LENGTH: 8
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(1)
<223> OTHER INFORMATION: Hydrazide functional group
<221> NAME/KEY: modified_base
<222> LOCATION: (8)..(8)
<223> OTHER INFORMATION: Cy3 dye
<221> NAME/KEY: modified_base
<222> LOCATION: (1)..(8)
<223> OTHER INFORMATION: pyranosyl RNA

<400> SEQUENCE: 90 taggcatt                                                                  8

<210> SEQ ID NO 91
<211> LENGTH: 12
<212> TYPE: DNA
<213> ORGANISM: Artificial sequence
<220> FEATURE:
<223> OTHER INFORMATION: Test nucleic acid sequence

<400> SEQUENCE: 91
ccccagtgct gg                                                            12

<210> SEQ ID NO 92
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(1)
<223> OTHER INFORMATION: Biotin moiety
<221> NAME/KEY: modified_base
<222> LOCATION: (1)..(10)
<223> OTHER INFORMATION: pyranosyl RNA

<400> SEQUENCE: 92
gaatgcagga                                                               10

<210> SEQ ID NO 93
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(1)
<223> OTHER INFORMATION: Biotin moiety
<221> NAME/KEY: modified_base
<222> LOCATION: (1)..(10)
<223> OTHER INFORMATION: pyranosyl RNA
```

```
<400> SEQUENCE: 93
agacgtagag                                                              10

<210> SEQ ID NO 94
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(1)
<223> OTHER INFORMATION: Biotin moiety
<221> NAME/KEY: modified_base
<222> LOCATION: (1)..(8)
<223> OTHER INFORMATION: pyranosyl RNA

<400> SEQUENCE: 94
aagtacgagg                                                              10

<210> SEQ ID NO 95
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(1)
<223> OTHER INFORMATION: Tetra-hydrazide moiety
<221> NAME/KEY: modified_base
<222> LOCATION: (1)..(10)
<223> OTHER INFORMATION: pyranosyl RNA

<400> SEQUENCE: 95
gaatgcagga                                                              10

<210> SEQ ID NO 96
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(1)
<223> OTHER INFORMATION: Tetra-hydrazide moiety
<221> NAME/KEY: modified_base
<222> LOCATION: (1)..(10)
<223> OTHER INFORMATION: pyranosyl RNA

<400> SEQUENCE: 96
agacgtagag                                                              10

<210> SEQ ID NO 97
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(1)
<223> OTHER INFORMATION: Tetra-hydrazide moiety
<221> NAME/KEY: modified_base
<222> LOCATION: (1)..(10)
<223> OTHER INFORMATION: pyranosyl RNA

<400> SEQUENCE: 97
aagtacgagg                                                              10

<210> SEQ ID NO 98
```

-continued

```
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(1)
<223> OTHER INFORMATION: Biotin moiety
<221> NAME/KEY: modified_base
<222> LOCATION: (1)..(10)
<223> OTHER INFORMATION: pyranosyl RNA

<400> SEQUENCE: 98
gaatgcagga                                                          10

<210> SEQ ID NO 99
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(1)
<223> OTHER INFORMATION: Biotin moiety
<221> NAME/KEY: modified_base
<222> LOCATION: (1)..(10)
<223> OTHER INFORMATION: pyranosyl RNA

<400> SEQUENCE: 99
agacgtagag                                                          10

<210> SEQ ID NO 100
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(1)
<223> OTHER INFORMATION: Biotin moiety
<221> NAME/KEY: modified_base
<222> LOCATION: (1)..(10)
<223> OTHER INFORMATION: pyranosyl RNA

<400> SEQUENCE: 100
aagtacgagg                                                          10

<210> SEQ ID NO 101
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(1)
<223> OTHER INFORMATION: Biotin moiety
<221> NAME/KEY: modified_base
<222> LOCATION: (1)..(10)
<223> OTHER INFORMATION: pyranosyl RNA

<400> SEQUENCE: 101
aggcataaag                                                          10

<210> SEQ ID NO 102
<211> LENGTH: 10
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(1)
```

```
<223> OTHER INFORMATION: Biotin moiety
<221> NAME/KEY: modified_base
<222> LOCATION: (1)..(10)
<223> OTHER INFORMATION: pyranosyl RNA

<400> SEQUENCE: 102
aacaagtggg                                                           10

<210> SEQ ID NO 103
<211> LENGTH: 35
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (26)..(35)
<223> OTHER INFORMATION: pyranosyl RNA

<400> SEQUENCE: 103
ctcaactgac atatagcatt gggcatcctg cattc                               35

<210> SEQ ID NO 104
<211> LENGTH: 40
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (31)..(40)
<223> OTHER INFORMATION: pyranosyl RNA

<400> SEQUENCE: 104
accctcactt caagactaag attgaaggta ctctacgtct                          40

<210> SEQ ID NO 105
<211> LENGTH: 35
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (26)..(35)
<223> OTHER INFORMATION: pyranosyl RNA

<400> SEQUENCE: 105
acccggttgt agtagttgca ggcaccctcg tactt                               35

<210> SEQ ID NO 106
<211> LENGTH: 38
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (29)..(38)
<223> OTHER INFORMATION: pyranosyl RNA

<400> SEQUENCE: 106
acaacaattt gaagcttctg taattttgct ttatgcct                            38

<210> SEQ ID NO 107
<211> LENGTH: 35
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (26)..(35)
<223> OTHER INFORMATION: pyranosyl RNA
```

```
<400> SEQUENCE: 107
tgtcagcctt gctacttgaa ggtaccccac ttgtt                    35

<210> SEQ ID NO 108
<211> LENGTH: 35
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (26)..(35)
<223> OTHER INFORMATION: pyranosyl RNA

<400> SEQUENCE: 108
cccctgtagg ttgcttaaaa gggactctgc tcatc                    35

<210> SEQ ID NO 109
<211> LENGTH: 35
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (26)..(35)
<223> OTHER INFORMATION: pyranosyl RNA

<400> SEQUENCE: 109
gcatggatgg cagcattgtt ctgaattcta tactc                    35

<210> SEQ ID NO 110
<211> LENGTH: 37
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (28)..(37)
<223> OTHER INFORMATION: pyranosyl RNA

<400> SEQUENCE: 110
gaggttcaag cgtaaataag tatattttgg tcggttg                  37

<210> SEQ ID NO 111
<211> LENGTH: 38
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (29)..(38)
<223> OTHER INFORMATION: pyranosyl RNA

<400> SEQUENCE: 111
cttctttcag tgggagggaa ctattgagtg gttatctg                 38

<210> SEQ ID NO 112
<211> LENGTH: 42
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (33)..(42)
<223> OTHER INFORMATION: pyranosyl RNA

<400> SEQUENCE: 112
acatttatta ttattattat tattattatt tgctccatgt tc            42
```

<210> SEQ ID NO 113
<211> LENGTH: 35
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (35)..(35)
<223> OTHER INFORMATION: Cy3 dye
<221> NAME/KEY: modified_base
<222> LOCATION: (26)..(35)
<223> OTHER INFORMATION: pyranosyl RNA

<400> SEQUENCE: 113
ctcaactgac atatagcatt gggcatcctg cattc    35

<210> SEQ ID NO 114
<211> LENGTH: 40
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (40)..(40)
<223> OTHER INFORMATION: Cy3 dye
<221> NAME/KEY: modified_base
<222> LOCATION: (31)..(40)
<223> OTHER INFORMATION: pyranosyl RNA

<400> SEQUENCE: 114
accctcactt caagactaag attgaaggta ctctacgtct    40

<210> SEQ ID NO 115
<211> LENGTH: 35
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (35)..(35)
<223> OTHER INFORMATION: Cy3 dye
<221> NAME/KEY: modified_base
<222> LOCATION: (26)..(35)
<223> OTHER INFORMATION: pyranosyl RNA

<400> SEQUENCE: 115
acccggttgt agtagttgca ggcaccctcg tactt    35

<210> SEQ ID NO 116
<211> LENGTH: 38
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (38)..(38)
<223> OTHER INFORMATION: Cy3 dye
<221> NAME/KEY: modified_base
<222> LOCATION: (29)..(38)
<223> OTHER INFORMATION: pyranosyl RNA

<400> SEQUENCE: 116
acaacaattt gaagcttctg taattttgct ttatgcct    38

<210> SEQ ID NO 117
<211> LENGTH: 35
<212> TYPE: DNA
<213> ORGANISM: Artificial sequence
<220> FEATURE:

```
<223> OTHER INFORMATION: Synthetic binding system
<221> NAME/KEY: modified_base
<222> LOCATION: (35)..(35)
<223> OTHER INFORMATION: Cy3 dye
<221> NAME/KEY: modified_base
<222> LOCATION: (26)..(35)
<223> OTHER INFORMATION: pyranosyl RNA

<400> SEQUENCE: 117
tgtcagcctt gctacttgaa ggtaccccac ttgtt                                35

<210> SEQ ID NO 118
<211> LENGTH: 35
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (35)..(35)
<223> OTHER INFORMATION: Cy3 dye
<221> NAME/KEY: modified_base
<222> LOCATION: (26)..(35)
<223> OTHER INFORMATION: pyranosyl RNA

<400> SEQUENCE: 118
cccctgtagg ttgcttaaaa gggactctgc tcatc                                35

<210> SEQ ID NO 119
<211> LENGTH: 35
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (35)..(35)
<223> OTHER INFORMATION: Cy3 dye
<221> NAME/KEY: modified_base
<222> LOCATION: (26)..(35)
<223> OTHER INFORMATION: pyranosyl RNA

<400> SEQUENCE: 119
gcatggatgg cagcattgtt ctgaattcta tactc                                35

<210> SEQ ID NO 120
<211> LENGTH: 37
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (37)..(37)
<223> OTHER INFORMATION: Cy3 dye
<221> NAME/KEY: modified_base
<222> LOCATION: (28)..(37)
<223> OTHER INFORMATION: pyranosyl RNA

<400> SEQUENCE: 120
gaggttcaag cgtaaataag tatattttgg tcggttg                              37

<210> SEQ ID NO 121
<211> LENGTH: 38
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (38)..(38)
<223> OTHER INFORMATION: Cy3 dye
<221> NAME/KEY: modified_base
<222> LOCATION: (29)..(38)
<223> OTHER INFORMATION: pyranosyl RNA
```

-continued

<400> SEQUENCE: 121
cttctttcag tgggagggaa ctattgagtg gttatctg                                38

<210> SEQ ID NO 122
<211> LENGTH: 42
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (42)..(42)
<223> OTHER INFORMATION: Cy3 dye
<221> NAME/KEY: modified_base
<222> LOCATION: (33)..(42)
<223> OTHER INFORMATION: pyranosyl RNA

<400> SEQUENCE: 122
acatttatta ttattattat tattattatt tgctccatgt tc                           42

<210> SEQ ID NO 123
<211> LENGTH: 25
<212> TYPE: DNA
<213> ORGANISM: Artificial sequence
<220> FEATURE:
<223> OTHER INFORMATION: Test nucleic acid sequence
<221> NAME/KEY: modified_base
<222> LOCATION: (1)..(1)
<223> OTHER INFORMATION: Cy5 dye

<400> SEQUENCE: 123
tgcccaatgc tatatgtcag ttgag                                              25

<210> SEQ ID NO 124
<211> LENGTH: 30
<212> TYPE: DNA
<213> ORGANISM: Artificial sequence
<220> FEATURE:
<223> OTHER INFORMATION: Test nucleic acid sequence
<221> NAME/KEY: modified_base
<222> LOCATION: (1)..(1)
<223> OTHER INFORMATION: Cy5 dye

<400> SEQUENCE: 124
taccttcaat cttagtcttg aagtgagggt                                         30

<210> SEQ ID NO 125
<211> LENGTH: 25
<212> TYPE: DNA
<213> ORGANISM: Artificial sequence
<220> FEATURE:
<223> OTHER INFORMATION: Test nucleic acid sequence
<221> NAME/KEY: modified_base
<222> LOCATION: (1)..(1)
<223> OTHER INFORMATION: Cy5 dye

<400> SEQUENCE: 125
gtgcctgcaa ctactacaac cgggt                                              25

<210> SEQ ID NO 126
<211> LENGTH: 28
<212> TYPE: DNA
<213> ORGANISM: Artificial sequence
<220> FEATURE:
<223> OTHER INFORMATION: Test nucleic acid sequence
<221> NAME/KEY: modified_base
<222> LOCATION: (1)..(1)
<223> OTHER INFORMATION: Cy5 dye -continued

<400> SEQUENCE: 126
caaaattaca gaagcttcaa attgttgt                                            28

<210> SEQ ID NO 127
<211> LENGTH: 25
<212> TYPE: DNA
<213> ORGANISM: Artificial sequence
<220> FEATURE:
<223> OTHER INFORMATION: Test nucleic acid sequence
<221> NAME/KEY: modified_base
<222> LOCATION: (1)..(1)
<223> OTHER INFORMATION: Cy5 dye

<400> SEQUENCE: 127
gtaccttcaa gtagcaaggc tgaca                                               25

<210> SEQ ID NO 128
<211> LENGTH: 25
<212> TYPE: DNA
<213> ORGANISM: Artificial sequence
<220> FEATURE:
<223> OTHER INFORMATION: Test nucleic acid sequence
<221> NAME/KEY: modified_base
<222> LOCATION: (1)..(1)
<223> OTHER INFORMATION: Cy5 dye

<400> SEQUENCE: 128 gtcccttta agcaacctac agggg                                                25

<210> SEQ ID NO 129
<211> LENGTH: 25
<212> TYPE: DNA
<213> ORGANISM: Artificial sequence
<220> FEATURE:
<223> OTHER INFORMATION: Test nucleic acid sequence
<221> NAME/KEY: modified_base
<222> LOCATION: (1)..(1)
<223> OTHER INFORMATION: Cy5 dye

<400> SEQUENCE: 129
ttcagaacaa tgctgccatc catgc                                               25

<210> SEQ ID NO 130
<211> LENGTH: 27
<212> TYPE: DNA
<213> ORGANISM: Artificial sequence
<220> FEATURE:
<223> OTHER INFORMATION: Test nucleic acid sequence
<221> NAME/KEY: modified_base
<222> LOCATION: (1)..(1)
<223> OTHER INFORMATION: Cy5 dye

<400> SEQUENCE: 130
aaatatactt atttacgctt gaacctc                                             27

<210> SEQ ID NO 131
<211> LENGTH: 27
<212> TYPE: DNA
<213> ORGANISM: Artificial sequence
<220> FEATURE:
<223> OTHER INFORMATION: Test nucleic acid sequence
<221> NAME/KEY: modified_base
<222> LOCATION: (1)..(1)
<223> OTHER INFORMATION: Cy5 dye

<400> SEQUENCE: 131
ctcaatagtt ccctcccact gaaagaa                                             27

-continued

<210> SEQ ID NO 132
<211> LENGTH: 32
<212> TYPE: DNA
<213> ORGANISM: Artificial sequence
<220> FEATURE:
<223> OTHER INFORMATION: Test nucleic acid sequence
<221> NAME/KEY: modified_base
<222> LOCATION: (1)..(1)
<223> OTHER INFORMATION: Cy5 dye

<400> SEQUENCE: 132
caaataataa taataataat aataataaat gt                32

<210> SEQ ID NO 133
<211> LENGTH: 35
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (26)..(35)
<223> OTHER INFORMATION: pyranosyl RNA

<400> SEQUENCE: 133
ctcaactgac atatagcatt gggcatcctg cattc                35

<210> SEQ ID NO 134
<211> LENGTH: 40
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (31)..(40)
<223> OTHER INFORMATION: pyranosyl RNA

<400> SEQUENCE: 134
accctcactt caagactaag attgaaggta ctctacgtct                40

<210> SEQ ID NO 135
<211> LENGTH: 35
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (26)..(35)
<223> OTHER INFORMATION: pyranosyl RNA

<400> SEQUENCE: 135
acccggttgt agtagttgca ggcaccctcg tactt                35

<210> SEQ ID NO 136
<211> LENGTH: 38
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (29)..(38)
<223> OTHER INFORMATION: pyranosyl RNA

<400> SEQUENCE: 136
acaacaattt gaagcttctg taattttgct ttatgcct                38

<210> SEQ ID NO 137
<211> LENGTH: 35
<212> TYPE: DNA

```
<213> ORGANISM: Artificial sequence
<220> FEATURE:
<223> OTHER INFORMATION: Synthetic binding system
<221> NAME/KEY: modified_base
<222> LOCATION: (26)..(35)
<223> OTHER INFORMATION: pyranosyl RNA

<400> SEQUENCE: 137
tgtcagcctt gctacttgaa ggtacccac ttgtt                               35

<210> SEQ ID NO 138
<211> LENGTH: 35
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (26)..(35)
<223> OTHER INFORMATION: pyranosyl RNA

<400> SEQUENCE: 138
cccctgtagg ttgcttaaaa gggactctgc tcatc                              35

<210> SEQ ID NO 139
<211> LENGTH: 35
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (26)..(35)
<223> OTHER INFORMATION: pyranosyl RNA

<400> SEQUENCE: 139
gcatggatgg cagcattgtt ctgaattcta tactc                              35

<210> SEQ ID NO 140
<211> LENGTH: 37
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (28)..(37)
<223> OTHER INFORMATION: pyranosyl RNA

<400> SEQUENCE: 140
gaggttcaag cgtaaataag tatattttgg tcggttg                            37

<210> SEQ ID NO 141
<211> LENGTH: 38
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (29)..(38)
<223> OTHER INFORMATION: pyranosyl RNA

<400> SEQUENCE: 141
cttctttcag tgggagggaa ctattgagtg gttatctg                           38

<210> SEQ ID NO 142
<211> LENGTH: 42
<212> TYPE: DNA
<213> ORGANISM: Artificial sequence
<220> FEATURE:
<223> OTHER INFORMATION: Synthetic binding system
<221> NAME/KEY: modified_base
```

```
<222> LOCATION: (33)..(42)
<223> OTHER INFORMATION: pyranosyl RNA

<400> SEQUENCE: 142
acatttatta ttattattat tattattatt tgctccatgt tc                   42

<210> SEQ ID NO 143
<211> LENGTH: 25
<212> TYPE: DNA
<213> ORGANISM: Artificial sequence
<220> FEATURE:
<223> OTHER INFORMATION: Test nucleic acid sequence

<400> SEQUENCE: 143
tgcccaatgc tatatgtcag ttgag                                      25

<210> SEQ ID NO 144
<211> LENGTH: 30
<212> TYPE: DNA
<213> ORGANISM: Artificial sequence
<220> FEATURE:
<223> OTHER INFORMATION: Test nucleic acid sequence

<400> SEQUENCE: 144
taccttcaat cttagtcttg aagtgagggt                                 30

<210> SEQ ID NO 145
<211> LENGTH: 25
<212> TYPE: DNA
<213> ORGANISM: Artificial sequence
<220> FEATURE:
<223> OTHER INFORMATION: Test nucleic acid sequence

<400> SEQUENCE: 145
gtgcctgcaa ctactacaac cgggt                                      25

<210> SEQ ID NO 146
<211> LENGTH: 28
<212> TYPE: DNA
<213> ORGANISM: Artificial sequence
<220> FEATURE:
<223> OTHER INFORMATION: Test nucleic acid sequence

<400> SEQUENCE: 146
caaaattaca gaagcttcaa attgttgt                                   28

<210> SEQ ID NO 147
<211> LENGTH: 25
<212> TYPE: DNA
<213> ORGANISM: Artificial sequence
<220> FEATURE:
<223> OTHER INFORMATION: Test nucleic acid sequence

<400> SEQUENCE: 147
gtaccttcaa gtagcaaggc tgaca                                      25

<210> SEQ ID NO 148
<211> LENGTH: 25
<212> TYPE: DNA
<213> ORGANISM: Artificial sequence
<220> FEATURE:
<223> OTHER INFORMATION: Test nucleic acid sequence

<400> SEQUENCE: 148
gtccctttta agcaacctac agggg                                      25
```

```
<210> SEQ ID NO 149
<211> LENGTH: 25
<212> TYPE: DNA
<213> ORGANISM: Artificial sequence
<220> FEATURE:
<223> OTHER INFORMATION: Test nucleic acid sequence

<400> SEQUENCE: 149
ttcagaacaa tgctgccatc catgc                                              25

<210> SEQ ID NO 150
<211> LENGTH: 27
<212> TYPE: DNA
<213> ORGANISM: Artificial sequence
<220> FEATURE:
<223> OTHER INFORMATION: Test nucleic acid sequence

<400> SEQUENCE: 150
aaatatactt atttacgctt gaacctc                                            27

<210> SEQ ID NO 151
<211> LENGTH: 28
<212> TYPE: DNA
<213> ORGANISM: Artificial sequence
<220> FEATURE:
<223> OTHER INFORMATION: Test nucleic acid sequence

<400> SEQUENCE: 151
ctcaatagtt ccctcccact gaaagaag                                           28

<210> SEQ ID NO 152
<211> LENGTH: 32
<212> TYPE: DNA
<213> ORGANISM: Artificial sequence
<220> FEATURE:
<223> OTHER INFORMATION: Test nucleic acid sequence

<400> SEQUENCE: 152
caaataataa taataataat aataataaat gt                                      32

<210> SEQ ID NO 153
<211> LENGTH: 25
<212> TYPE: DNA
<213> ORGANISM: Artificial sequence
<220> FEATURE:
<223> OTHER INFORMATION: Test nucleic acid sequence
<221> NAME/KEY: modified_base
<222> LOCATION: (25)..(25)
<223> OTHER INFORMATION: Cy3 dye

<400> SEQUENCE: 153
tgcccaatgc tatatgtcag ttgag                                              25

<210> SEQ ID NO 154
<211> LENGTH: 30
<212> TYPE: DNA
<213> ORGANISM: Artificial sequence
<220> FEATURE:
<223> OTHER INFORMATION: Test nucleic acid sequence
<221> NAME/KEY: modified_base
<222> LOCATION: (30)..(30)
<223> OTHER INFORMATION: Cy3 dye

<400> SEQUENCE: 154
taccttcaat cttagtcttg aagtgagggt                                         30
```

<210> SEQ ID NO 155
<211> LENGTH: 25
<212> TYPE: DNA
<213> ORGANISM: Artificial sequence
<220> FEATURE:
<223> OTHER INFORMATION: Test nucleic acid sequence
<221> NAME/KEY: modified_base
<222> LOCATION: (25)..(25)
<223> OTHER INFORMATION: Cy3 dye

<400> SEQUENCE: 155
gtgcctgcaa ctactacaac cgggt                    25

<210> SEQ ID NO 156
<211> LENGTH: 28
<212> TYPE: DNA
<213> ORGANISM: Artificial sequence
<220> FEATURE:
<223> OTHER INFORMATION: Test nucleic acid sequence
<221> NAME/KEY: modified_base
<222> LOCATION: (28)..(28)
<223> OTHER INFORMATION: Cy3 dye

<400> SEQUENCE: 156
caaaattaca gaagcttcaa attgttgt                 28

<210> SEQ ID NO 157
<211> LENGTH: 25
<212> TYPE: DNA
<213> ORGANISM: Artificial sequence
<220> FEATURE:
<223> OTHER INFORMATION: Test nucleic acid sequence
<221> NAME/KEY: modified_base
<222> LOCATION: (25)..(25)
<223> OTHER INFORMATION: Cy3 dye

<400> SEQUENCE: 157
gtaccttcaa gtagcaaggc tgaca                    25

<210> SEQ ID NO 158
<211> LENGTH: 25
<212> TYPE: DNA
<213> ORGANISM: Artificial sequence
<220> FEATURE:
<223> OTHER INFORMATION: Test nucleic acid sequence
<221> NAME/KEY: modified_base
<222> LOCATION: (25)..(25)
<223> OTHER INFORMATION: Cy3 dye

<400> SEQUENCE: 158 gtcccttta agcaacctac agggg                     25

<210> SEQ ID NO 159
<211> LENGTH: 25
<212> TYPE: DNA
<213> ORGANISM: Artificial sequence
<220> FEATURE:
<223> OTHER INFORMATION: Test nucleic acid sequence
<221> NAME/KEY: modified_base
<222> LOCATION: (25)..(25)
<223> OTHER INFORMATION: Cy3 dye

<400> SEQUENCE: 159
ttcagaacaa tgctgccatc catgc                    25

<210> SEQ ID NO 160
<211> LENGTH: 27
<212> TYPE: DNA
<213> ORGANISM: Artificial sequence

```
<220> FEATURE:
<223> OTHER INFORMATION: Test nucleic acid sequence
<221> NAME/KEY: modified_base
<222> LOCATION: (27)..(27)
<223> OTHER INFORMATION: Cy3 dye

<400> SEQUENCE: 160
aaatatactt atttacgctt gaacctc                                          27

<210> SEQ ID NO 161
<211> LENGTH: 28
<212> TYPE: DNA
<213> ORGANISM: Artificial sequence
<220> FEATURE:
<223> OTHER INFORMATION: Test nucleic acid sequence
<221> NAME/KEY: modified_base
<222> LOCATION: (28)..(28)
<223> OTHER INFORMATION: Cy3 dye

<400> SEQUENCE: 161
ctcaatagtt ccctcccact gaaagaag                                         28

<210> SEQ ID NO 162
<211> LENGTH: 32
<212> TYPE: DNA
<213> ORGANISM: Artificial sequence
<220> FEATURE:
<223> OTHER INFORMATION: Test nucleic acid sequence
<221> NAME/KEY: modified_base
<222> LOCATION: (32)..(32)
<223> OTHER INFORMATION: Cy3 dye

<400> SEQUENCE: 162
caaataataa taataataat aataataaat gt                                    32

<210> SEQ ID NO 163
<211> LENGTH: 25
<212> TYPE: DNA
<213> ORGANISM: Artificial sequence
<220> FEATURE:
<223> OTHER INFORMATION: Test nucleic acid sequence
<221> NAME/KEY: modified_base
<222> LOCATION: (1)..(1)
<223> OTHER INFORMATION: Cy5 dye

<400> SEQUENCE: 163
tgcccaatgc tatatgtcag ttgag                                            25

<210> SEQ ID NO 164
<211> LENGTH: 30
<212> TYPE: DNA
<213> ORGANISM: Artificial sequence
<220> FEATURE:
<223> OTHER INFORMATION: Test nucleic acid sequence
<221> NAME/KEY: modified_base
<222> LOCATION: (1)..(1)
<223> OTHER INFORMATION: Cy5 dye

<400> SEQUENCE: 164
taccttcaat cttagtcttg aagtgagggt                                       30

<210> SEQ ID NO 165
<211> LENGTH: 25
<212> TYPE: DNA
<213> ORGANISM: Artificial sequence
<220> FEATURE:
<223> OTHER INFORMATION: Test nucleic acid sequence

<400> SEQUENCE: 165
```

```
gtgcctgcaa ctactacaac cgggt                                          25

<210> SEQ ID NO 166
<211> LENGTH: 28
<212> TYPE: DNA
<213> ORGANISM: Artificial sequence
<220> FEATURE:
<223> OTHER INFORMATION: Test nucleic acid sequence
<221> NAME/KEY: modified_base
<222> LOCATION: (1)..(1)
<223> OTHER INFORMATION: Cy5 dye

<400> SEQUENCE: 166
caaaattaca gaagcttcaa attgttgt                                       28

<210> SEQ ID NO 167
<211> LENGTH: 25
<212> TYPE: DNA
<213> ORGANISM: Artificial sequence
<220> FEATURE:
<223> OTHER INFORMATION: Test nucleic acid sequence
<221> NAME/KEY: modified_base
<222> LOCATION: (1)..(1)
<223> OTHER INFORMATION: Cy5 dye

<400> SEQUENCE: 167
gtaccttcaa gtagcaaggc tgaca                                          25

<210> SEQ ID NO 168
<211> LENGTH: 25
<212> TYPE: DNA
<213> ORGANISM: Artificial sequence
<220> FEATURE:
<223> OTHER INFORMATION: Test nucleic acid sequence
<221> NAME/KEY: modified_base
<222> LOCATION: (1)..(1)
<223> OTHER INFORMATION: Cy5 dye

<400> SEQUENCE: 168
gtccctttta agcaacctac agggg                                          25

<210> SEQ ID NO 169
<211> LENGTH: 25
<212> TYPE: DNA
<213> ORGANISM: Artificial sequence
<220> FEATURE:
<223> OTHER INFORMATION: Test nucleic acid sequence
<221> NAME/KEY: modified_base
<222> LOCATION: (1)..(1)
<223> OTHER INFORMATION: Cy5 dye

<400> SEQUENCE: 169
ttcagaacaa tgctgccatc catgc                                          25

<210> SEQ ID NO 170
<211> LENGTH: 27
<212> TYPE: DNA
<213> ORGANISM: Artificial sequence
<220> FEATURE:
<223> OTHER INFORMATION: Test nucleic acid sequence
<221> NAME/KEY: modified_base
<222> LOCATION: (1)..(1)
<223> OTHER INFORMATION: Cy5 dye

<400> SEQUENCE: 170
aaatatactt atttacgctt gaacctc                                        27
```

<210> SEQ ID NO 171
<211> LENGTH: 28
<212> TYPE: DNA
<213> ORGANISM: Artificial sequence
<220> FEATURE:
<223> OTHER INFORMATION: Test nucleic acid sequence
<221> NAME/KEY: modified_base
<222> LOCATION: (1)..(1)
<223> OTHER INFORMATION: Cy5 dye

<400> SEQUENCE: 171
ctcaatagtt ccctcccact gaaagaag                                            28

<210> SEQ ID NO 172
<211> LENGTH: 34
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(10)
<223> OTHER INFORMATION: pyranosyl RNA

<400> SEQUENCE: 172
tcctgcattc agaaatctca catggacatc ttca                                     34

<210> SEQ ID NO 173
<211> LENGTH: 25
<212> TYPE: DNA
<213> ORGANISM: Artificial sequence
<220> FEATURE:
<223> OTHER INFORMATION: Test nucleic acid sequence

<400> SEQUENCE: 173
gtctgtttca cagaagaggg tccaa                                               25

<210> SEQ ID NO 174
<211> LENGTH: 32
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (1)..(10)
<223> OTHER INFORMATION: pyranosyl RNA

<400> SEQUENCE: 174
tcctgcattc cctgggcttt gcagcacttc tc                                       32

<210> SEQ ID NO 175
<211> LENGTH: 25
<212> TYPE: DNA
<213> ORGANISM: Artificial sequence
<220> FEATURE:
<223> OTHER INFORMATION: Test nucleic acid sequence

<400> SEQUENCE: 175
gatctgtgcc aagctcaggg caaag                                               25

<210> SEQ ID NO 176
<211> LENGTH: 2009
<212> TYPE: DNA
<213> ORGANISM: Mus musculus
<220> FEATURE:
<221> NAME/KEY: gene
<222> LOCATION: (1)..(2009)
<223> OTHER INFORMATION: Alpha-fetoprotein

<400> SEQUENCE: 176

-continued

```
tcccacttcc agcactgcct gcggtgaagg aacaagcagc catgaagtgg atcacacccg    60
cttccctcat cctcctgcta catttcgctg cgtccaaagc attgcacgaa aatgagtttg   120
ggatagcttc cacgttagat tcctcccagt gcgtgacgga aagaatgtg cttagcatag    180
ctaccatcac ctttacccag tttgttccgg aagccaccga ggaggaagtg aacaaaatga   240
ctagcgatgt gttggctgca atgaagaaaa actctggcga tgggtgttta gaaagccagc   300
tatctgtgtt tctggatgaa atttgccatg agacggaact ctctaacaag tatggactct   360
caggctgctg cagccaaagt ggagtggaaa gacatcagtg tctgctgcca cgcaagaaga   420
ctgctccggc ctctgtccca cccttccagt ttccagaacc tgccgagagt tgcaaagcac   480
atgaagaaaa cagggcagtg ttcatgaaca ggttcatcta tgaagtgtca aggaggaacc   540
ccttcatgta tgccccagcc attctgtcct ggctgctcca gtacgacaag gtcgttctgg   600
catgctgcaa agctgacaac aaggaggagt gcttccagac aaagagagca tccattgcaa   660
aggaattaag agaaggaagc atgttaaatg agcatgtatg ttcagtgata gaaaatttg    720
gatcccgaaa cctccaggca caaccatta ttaagctaag tcaaaagtta actgaagcaa    780
attttactga gattcagaag ctggccctgg atgtggctca catccacgag gagtgttgcc   840
aaggaaactc gctggagtgt ctgcaggatg gggaaaaagt catgacatat atatgttctc   900
aacaaaatat tctgtcaagc aaaatagcag agtgctgcaa attacccatg atccaactag   960
gcttctgcat aattcacgca gagaatggcg tcaaacctga aggcttatct ctaaatccaa  1020
gccagttttt gggagacaga aattttgccc aattttcttc agaggaaaaa atcatgttca  1080
tggcaagctt tcttcatgaa tactcaagaa ctcaccccaa ccttcctgtc tcagtcattc  1140
taagaattgc taaaacgtac caggaaatat tggagaagtg ttcccagtct ggaaatctac  1200
ctggatgtca ggacaatctg gaagaagaat tgcagaaaca catcgaggag agccaggcac  1260
tgtccaagca aagctgcgct ctctaccaga ccttaggaga ctacaaatta caaatctgt    1320
tccttattgg ttacacgagg aaagcccctc agctgacctc agcagagctg atcgacctca  1380
ccgggaagat ggtgagcatt gcctccacgt gctgccagct cagcgaggag aaatggtccg  1440
gctgtggtga gggaatggcc gacatttca ttggacattt gtgtataagg aatgaagcaa    1500
gccctgtgaa ctctggtatc agccactgct gcaactcttc gtattccaac aggaggctat  1560
gcatcaccag ttttctgagg gatgaaacct atgcccctcc ccattctct gaggataaat    1620
tcatcttcca caaggatctg tgccaagctc agggcaaagc cctacagacc atgaaacaag  1680
agcttctcat taacctggtg aagcaaaagc ctgaactgac agaggagcag ctggcggctg  1740
tcactgcaga tttctcgggc cttttggaga agtgctgcaa agcccaggac caggaagtct  1800
gtttcacaga agagggtcca aagttgattt ccaaaactcg tgatgctttg ggcgttaaa    1860
catctccaga aggaagagtg gacaaaaaaa tgtgttgacg ctttggtgtg agccttttgg  1920
cttaactgta actgctagta cttttaaccac atggtgaaga tgtccatgtg agatttctat  1980
accttaggaa taaaaactt tcaactatt                                      2009
```

<210> SEQ ID NO 177
<211> LENGTH: 20
<212> TYPE: DNA
<213> ORGANISM: Artificial sequence
<220> FEATURE:
<223> OTHER INFORMATION: Test nucleic acid sequence

<400> SEQUENCE: 177

-continued

```
taatacgact cactataggg                                              20

<210> SEQ ID NO 178
<211> LENGTH: 18
<212> TYPE: DNA
<213> ORGANISM: Artificial sequence
<220> FEATURE:
<223> OTHER INFORMATION: Test nucleic acid sequence

<400> SEQUENCE: 178
tggggctaag cgggatcg                                                18

<210> SEQ ID NO 179
<211> LENGTH: 113
<212> TYPE: DNA
<213> ORGANISM: Artificial sequence
<220> FEATURE:
<223> OTHER INFORMATION: Test nucleic acid sequence

<400> SEQUENCE: 179
gctgcagtaa tacgactcac tagggggct atagctcagc tgggagagcg cttgcctggg   60
aagcaagagg tcagcggttc gatcccgctt agccccaccg cggcgtccat cca         113

<210> SEQ ID NO 180
<211> LENGTH: 67
<212> TYPE: DNA
<213> ORGANISM: Artificial sequence
<220> FEATURE:
<223> OTHER INFORMATION: Test WT nucleic acid sequence

<400> SEQUENCE: 180
ggcgttttgc aaacatacct tcaatcttag tcttgaagtg agggtgtctg ttgagaatct   60
ccacctg                                                            67

<210> SEQ ID NO 181
<211> LENGTH: 67
<212> TYPE: DNA
<213> ORGANISM: Artificial sequence
<220> FEATURE:
<223> OTHER INFORMATION: Test mutant nucleic acid sequence

<400> SEQUENCE: 181
ggcgttttgc aaacatacct tcaatcttag tcttgaagtg agggtatctg ttgagaatct   60
ccacctg                                                            67

<210> SEQ ID NO 182
<211> LENGTH: 40
<212> TYPE: DNA
<213> ORGANISM: Artificial sequence
<220> FEATURE:
<223> OTHER INFORMATION: Synthetic binding system
<221> NAME/KEY: modified_base
<222> LOCATION: (31)..(40)
<223> OTHER INFORMATION: pyranosyl RNA

<400> SEQUENCE: 182
accctcactt caagactaag attgaaggta tcctgcattc                        40

<210> SEQ ID NO 183
<211> LENGTH: 11
<212> TYPE: DNA
<213> ORGANISM: Artificial sequence
<220> FEATURE:
<223> OTHER INFORMATION: Test WT rept. nucleic acid sequence
<221> NAME/KEY: modified_base
```

-continued

```
<222> LOCATION: (1)..(1)
<223> OTHER INFORMATION: Cy3 dye

<400> SEQUENCE: 183
tctcaacaga c                                                           11

<210> SEQ ID NO 184
<211> LENGTH: 11
<212> TYPE: DNA
<213> ORGANISM: Artificial sequence
<220> FEATURE:
<223> OTHER INFORMATION: Test mut. rept. nucleic acid sequence
<221> NAME/KEY: modified_base
<222> LOCATION: (1)..(1)
<223> OTHER INFORMATION: Cy5 dye

<400> SEQUENCE: 184
tctcaacaga t                                                           11
```

ENZYMATIC MODIFICATION OF A NUCLEIC ACID-SYNTHETIC BINDING UNIT CONJUGATE

FIELD OF INVENTION

The present invention relates to conjugates of synthetic binding units and nucleic acids. The present invention also relates to methods for sorting and immobilizing nucleic acids on support materials using such conjugates by specific molecular addressing of the nucleic acids mediated by the synthetic binding systems. Particularly, the present invention also relates to novel methods of utilizing conjugates of synthetic binding units and nucleic acids to in active electronic array systems to produce novel array constructs from the conjugates, and the use of such constructs in various nucleic acid assay formats. In addition, the present invention relates to various novel forms of such conjugates, improved methods of making solid phase synthesized conjugates, and improved methods of conjugating pre-synthesized synthetic binding units and nucleic acids. The present invention also relates to the use of conjugates of synthetic binding units and nucleic acids as substrates for various enzymatic reactions, including nucleic acid amplification reactions.

BACKGROUND OF THE INVENTION

Nucleic acid chemistries and analyses have risen to a place of prominence in such diverse areas as biological research, medicine, agriculture, and even forensic science. A key need in the use of nucleic acids in all of these areas is the ability to manipulate them on a macroscopic scale by localizing particular nucleic acid species (or groups of species) at a known location, such as in an array on a substrate. In order to immobilize nucleic acids on support materials, a wide range of methods have been devised, which can be loosely classified by the stability of the bond. A covalent immobilization, i.e. an immobilization in which the nucleic acid is linked to molecular structures of the support material by covalent bonds, is typically irreversible without risking the degradation of the immobilized nucleic acid. In contrast, complexing reactions, or reactions between two partners of a binding system which specifically recognize each other, may be used. These reactions may be reversible or, for practical purposes, irreversible over the timescale of a particular experiment. Whether a binding system for immobilizing nucleic acids is to be denoted reversible or irreversible depends ultimately on the position of the equilibrium between bound and free nucleic acids. An example of a binding system to be regarded as practically irreversible is the complexing of biotin by avidin (or streptavidin, or their various engineered equivalent proteins,) with a binding constant of $K_a \sim 2.5 \times 10^{13}$ ($M^{-1}$) (Chilkoti, A.; Stayton, P. A.; J. Am. Chem. Soc. 117, 10622–10628 (1995); Greene M.; Advances in Protein Chemistry; 85–132 (1975)). This system has been widely used for immobilizing nucleic acids and other biomolecules on support materials.

WO 86/07387 describes a different example of reversible binding of nucleic acids to surfaces. As described here, nucleic acid binding sequences are immobilized on support materials by means of complexing agents, for example with the aid of antibody/antigen pairs.

Another example of a reversible pairing system which has been used are sets of natural-nucleotide oligomers, which specifically hybridize to provide duplexing "tags" for immobilization. In contrast to biotin-streptavidin, nucleic acid oligomers have an informatic dimensionality in pair formation: there are a multiplicity of specific binding sets which may be devised, characterized by the sequence of monomers (nucleotides) which specifically pair only with complementary sequences. Unlike multi-hapten-lectin systems, or multi-antibody-antigen systems, such sets of nucleic acid tags have fairly uniform chemical and thermodynamic characteristics, which facilitates their use in multiplex reactions.

EP 0 305 145 describes, for example, the use of homopolynucleotide tails and their specific pairing with complementary homopolynucleotide oligomers for immobilizing target-specific oligonucleotides. On the other hand, JP 03 151 900 describes the use of specific nucleic acid sequences for immobilizing target-specific nucleic acids. It is characteristic of such systems that the oligonucleotide to be immobilized is composed of two parts: one oligomeric part complementary to the oligonucleotide immobilized on the surface of the support, and a second oligomeric part specific for interaction with components of the sample (e.g., complementary to a sample nucleic acid.) Similar systems are also described in WO 93/13225, WO 93/13223, WO 93/25563, U.S. Pat. No. 5,763,175, WO 97/32999, WO 00/58516 and in WO 00/60124.

The disadvantage of the methods described above is that the sequence used for the immobilization can potentially hybridize with the sequence to be immobilized, forming intramolecular secondary structures, may hybridize with another sequence to be immobilized, forming intermolecular secondary structures, or may hybridize with nucleic acids from the sample. The risk of such an unwanted or interfering interaction increases with the length of the nucleic acid(s) to be immobilized, as well as with the complexity of a sample (e.g., the possibility of contaminating nucleic acids from unknown organisms.)

Another disadvantage of the use of natural nucleic acids for immobilization is that the stability of duplexes of natural nucleic acids does not increase linearly in proportion to length (number of nucleotides in the sequence) over a large range, but rather approaches a limit which depends only on the relative percentage of CG to AT base pairs ("CG content"). Binding systems having a duplex stability exceeding the natural limit cannot be prepared using natural nucleic acids. This limitation is also problematic when applying various stringency conditions to the nucleic acid at its immobilized location: the immobilizing nucleic acid tags will also be subjected to the same stringency conditions (i.e., chaotropic agents, thermal conditions, or electrostatic forces), and may dissociate. See G. Michael Blackburn and Michael J. Gait, eds. *Nucleic Acids in Chemistry and Biology*, 2nd ed., 1996, Oxford University Press, New York.

Achieving a fine differentiation in stringency differentiation between immobilization tag interactions (which must remain hybridized) and the target-specific interactions (which are often discriminated at the single base pair mismatch level) is often difficult, especially under clinical-type conditions when the method must be particularly robust and consistent.

Another significant economic and time disadvantage of using natural nucleic acids as immobilization agents is that a certain minimum sequence length is required to reach a practical level of stability and selectivity of the immobilization. It is to typical to use 20-mers in order to achieve sufficient binding specificity. This results in the entire nucleic acid strand (composed of the sequence for recognizing the sample and the sequence for immobilization)

becoming relatively long. The use very long sequences can be disadvantageous for several reasons. First, the use of long nucleic acid sequences increases the likelihood of secondary structure formation intramolecularly, and also increases the likelihood of transient or stable hybridization between multiple strands in solution.

Active electronic array devices have been described for the electrophoretic transport and manipulation of nucleic acids, see U.S. Pat. Nos. 6,245,508; 6,225,059; 6,051,380; and 6,017,696, the text of each of which is hereby incorporated by reference in their entirety. When manipulating nucleic acids on active electronic arrays, the use of shorter sequences is preferred. Electro-kinetic addressing and movement on the electronic chip array work particularly well with relatively short nucleic acids because of the better electrophoretic mobility of the smaller molecules. Thus, shorter sequences for use as immobilization complexing agents have increased utility in the context of active electronic arrays.

Another disadvantage of using natural systems for the immobilization of nucleic acids is that such systems can be easily degraded or destroyed during their use. In particular, degradation by enzymatic components of the sample, or even contaminating DNAses and RNAses from laboratory workers' fingertips, is a concern. Degradation or fragmentation by hydrolysis of the nucleic acids used for immobilization, in particular by enzymes such as, restriction enzymes, exonucleases or endonucleases, in not uncommon when a nucleic acid oligomer is allowed to sit at room temperature for a few days. Thus, the use of complexing agents for immobilization which are not subject to degradation or modification by naturally occurring enzymes is desirable.

In the course of the last few decades, a plurality of technologies have been developed to take advantage of the diverse natural variety of enzymes to modify nucleic acids. Restriction endonuclease reactions specifically cleave nucleic acids at defined sequence sites, and nucleases or other enzymes can be utilized to degrade or modify nucleic acids at either termini. In addition, polymerases and terminal transferases can be utilized to build nucleic acid oligomers from nucleotides. Ligase enzymes may also be utilized to connect, or ligate, different nucleic acid strands with one another, in single-strand template dependant, blunt-end double-stranded, or single-strand template independent manners. These enzymatic tools have become a mainstay of analytical biochemistry, and are necessary for almost any molecular biology research at some point. For instance, polymerases are commonly used for carrying out nucleic acid amplification reactions and sequencing reactions, which are both necessary components of the production of proteins of interest in research.

In most cases, purification steps or physical separation steps are required for handling at each stage of the enzymatic manipulations of nucleic acids. Nucleic acids are usually purified by precipitation, electrophoretic separation, or chromatographic steps. For isolation and immobilization purposes, nucleic acids are often modified with an affinity tag, like biotin. These biotin-modified nucleic acids can be bound stably and irreversibly to solid phases via macromolecular biotin-streptavidin complexes (e.g. DE 40 011 54 and EP 0 063 879). The very large complex obtained can be separated again only by rather harsh chemical conditions. Although a commonly used complex, this provides only one immobilization interaction tool: multiplex reactions with specific localization of the products cannot be done with a biotin-streptavidin affinity system alone. Alternatively, A is possible to elaborately incorporate polyhistidine modifications, or steroids or haptens, such as digoxigenin, into a nucleic acid in order to make separation possible by fixing to binding partners corresponding to the modifications. However, these systems only allow separation under diverse conditions (nickel chromatography, vs antibody binding,) and thus do not overcome the limitations of the biotin-avidin interaction for multiplex reactions.

Chemical conjugation of one nucleic acid to another nucleic acid in solution requires that one nucleic acid is provided with a modification which can react with the modification of the other nucleic acid by forming a stable bond. Often, finished, pre-synthesized nucleic acids are conjugated with other nucleic acids and analogs by utilizing the ability of nucleic acids to form complementary pairs with themselves, or by the pairing of the nucleic acids with a nucleic acid template for ligation. The pairing leads to an association or pre-organization of the parts to be conjugated, which supports or else makes thermodynamically favorable the subsequent conjugation reaction. For example, Nucleic Acids Research 16(9), 3671–3691 (1988) describes the conjugation of thiol-modified nucleic acids. This option allows, when treated with atmospheric oxygen, the formation of both homodimers and heterodimers, and is therefore only provisionally suitable for linking together two different nucleic acids. The template-supported conjugation of aldehyde-modified nucleic acids with amine-modified nucleic acids is described in J. Am. Chem. Soc. 114, 9197–9198, (1992). Another template-supported photochemical conjugation is described in Nucleic Acids Research 26(13), 3300–3304, (1998). One of the few reactions described without support by self-binding or template binding is the reaction of phosphorothioates with α-haloacetylene (Gryaznov S M, J. Am. Chem. Soc. 115, 3808–3809, (1993)). WO 01/07657 describes the linkage of RNA building blocks at the 3' end of an RNA oligonucleotide by oxidation with periodate to give the dialdehyde and subsequent reaction with a nitrogen nucleophile to give a cyclic product. The nitrogen nucleophiles used may be amines, hydrazines, hydrazides, semicarbazides or thiosemicarbazides. The product formed initially can be stabilized by reduction with $NaCNBH_3$.

Since synthetic binding systems, such as pyranosyl-RNA (pRNA) or pyranosyl-DNA (pDNA) binding systems, are, by design, not sterically capable of pairing with nucleic acids, these previously described methods are not applicable to conjugating to nucleic acids with synthetic binding units. However, the solid-phase tandem synthesis of synthetic binding unit/nucleic acid conjugates by phosphoramidite chemistry is not desirable for circumstances in which a nucleic acid is readily available for conjugation (e.g., a bacterial plasmid preparation.) Likewise, if the nucleic acid to be conjugated is longer than about 20 nucleotides, the size of the conjugate (nucleic acid +6–15 pRNA residues) approaches and eventually surpasses the efficient synthesis limit of the solid-phase chemistry. There is therefore a need to find methods and conditions which make it possible to conjugate finished, pre-synthesized nucleic acids with synthetic binding systems.

SUMMARY OF THE INVENTION

In a first aspect, the invention provides novel methods for the active construction of arrays of immobilized nucleic acids utilizing active array devices. In the invention, an array of immobilized nucleic acids is produced on an active location array device comprising a plurality of activatable locations on a support material, by:

a) activating a first set $L_1$ of locations on the active array device, wherein at least some of the activated locations comprise, or have attached thereto, a predetermined synthetic addressing unit (SAU) or set of synthetic addressing units attached at the locations, and wherein the activation of the locations creates a condition favorable to the binding of the SAUs to SBUs;

b) contacting the activated set of locations with a first set $C_1$ of synthetic binding unit (SBU)—nucleic acid (NA) conjugates, wherein at least some of the SBUs in the set of conjugates are capable of specifically binding to at least some of the SAUs attached at the activated locations;

c) removing the unbound conjugates; and d) repeating steps (a) through (c) M number of times, activating set $L_{M+1}$ of locations, and contacting them with set $C_{M+1}$ of conjugates, wherein $M \geq 1$.

In embodiments of the first aspect, it is preferred that at least to locations of the active device, the same SAU is attached. Preferred embodiments also utilize rectangularly arrayed locations. Particularly preferred embodiments may use active electronic array devices, optionally with electronic washing. The various specific SAUs and SBUs described throughout the specification are useful in this first aspect, as are the various specific conjugate structures. Likewise, the various libraries described throughout the specification may be used as sets C in this aspect of the invention. In various embodiments of the first aspect of the invention, the SAUs may be attached to the locations of the array by active addressing means, or passively by more traditional spotting means.

In various embodiments of the first aspect of the invention, at least 10, at least 100, at least 1000, or even 10,000 or more distinct nucleic acids may be immobilized on the active location array. Likewise, in the invention, various numbers of conjugates in each set C may be immobilized at each cycle M, such as groups of at least 5, at least 10, at least 20, or even 100 conjugates at each cycle. This may be carried out for several cycles, preferably where M is between 1 and 100, preferably between 1 and 20, or also preferably between 1 and 10, depending on the size of the active location array, and the desired number of conjugates in each set C.

In additional embodiments of this first aspect, the conjugates for immobilization on the array are first contacted with a sample, preferably a biological sample, before being contacted with the solid support. In preferred embodiments, the conjugates may be utilized in an amplification reaction while contacted with the sample. In other additional embodiments, the constructed array is later contacted with a sample, preferably a biological sample. Optionally, the array may be subjected to a detection step, in which the immobilized conjugates, or target nucleic acids hybridized to the immobilized conjugates, are detected.

In additional embodiments of the first aspect of the invention, the array may be subjected to a further step in which the conjugates are removed from the array by disrupting the SBU/SAU interaction, thus regenerating the support with attached SAUs for further use.

A second aspect of the invention are novel array constructs, which are produced using the active array construction methods. These novel supermolecular constructs comprise:

a) at least one synthetic address unit (SAU) (either a single SAU or a mixture of SAUs) attached to a support material comprising an array of discreet locations, wherein the same SAU is attached to at least two predetermined locations on the support material, and b) at least two conjugates comprising a synthetic binding unit (SBU) and a nucleic acid (NA), wherein at least two of the conjugates have the same SBU and different NAs;

c) wherein the SBU of the conjugates form a synthetic binding system unit (SBS) with the SAU at the two predetermined locations, and immobilize each of the two different NAs at a different location.

The SAUs and SBU conjugates described throughout the application may be utilized in various embodiments of the second aspect of the invention. In addition, various types of support materials described below may be utilized. A preferred embodiment of the second aspect utilizes an active electronic array as the support for the supermolecular construct. The supermolecular constructs may comprise at least 5, at least 10, or 100 or more different conjugates immobilized by the same synthetic binding system. The constructs may also comprise at least 10, at least 100, at least 1000, or even 10,000 or more different immobilized nucleic acids in preferred embodiments of the second aspect, the supermolecular construct comprises two or ran more different SAUs attached to different locations on the support material, where the SAUs are orthogonal.

In a third aspect, the invention provides several novel conjugates which can be used to sort and immobilize nucleic acids on a support materials. The conjugates of this aspect of the invention have the general formula (NA)(SBU) wherein:

NA is a nucleic acid,

SBU is a synthetic binding unit, wherein each NA is linked to at least one SBU by a linker X, wherein X is selected from the group consisting of:

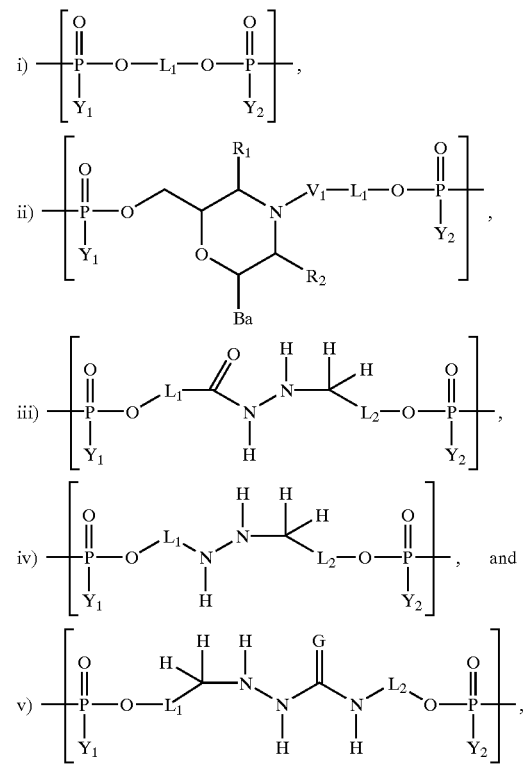

wherein $Y_1, Y_2$ are independently of one another OH; SH, $NH_2$ or $CH_3$

G is O or S,

L₁, L₂ are independently linkers selected from the group consisting of: a covalent bond; and a linker chain moiety comprising a saturated or unsaturated, branched or unbranched, substituted or unsubstituted, chain of 1–60 carbon atoms and 0–40 heteroatoms selected from the group consisting of N, O, and S;

V₁, V₂ are independently selected from the group consisting of —[—CH₂—]—, and

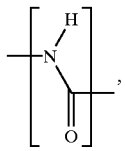

R₁, R₂ are independently of one another H or OH, and wherein

Ba is a nitrogen heterocycle moiety.

In various embodiments of this aspect of the invention, the linker X may have any of the general formulae (i)–(v), and may be oriented in either direction. In various embodiments of the invention, L may be linkers including:

—[—(CH₂)ₙ—]—
or —[—CH₂—CH₂—(O—CH₂—CH₂)ₘ]—
or —[—CH₂—CH₂—CH₂—(O—CH₂CH₂—CH₂)_z—]—
or —[—(CH₂)ₙ—C(O)NH—(CH₂)_z—]—
or —[—(CH₂)ᵥ—NHC(O)—(CH₂)_z—]— with n, m, q, v, z in each case independently of one another being an integer between 1 and 20, and more preferably, n is between 2 and 12, m is between 1 and 5, q is a between 1 and 4, and v and z are independently between 2 and 6.

In a fourth aspect, the invention provides novel branched or linear conjugates, with the general formula (NA)ₙ(SBU)ₘ, wherein:

NA is a nucleic acid,
SBU is a synthetic binding unit, wherein each NA is linked to at least one SBU, n is an integer from 1 to 6, m is an integer from 1 to 6, and wherein n+m>2. In preferred embodiments of the fourth aspect of the invention, the conjugates have a structure with a general formula selected from the group consisting of (I), (II), or (III):

(NA)—X₁—(SBU)—X₂—(NA)  (formula (I))

(SBU)—Y—X₁—(NA)—X₂—(SBU)  (formula (II))

(NA)—W—(—(SBU))ᵤ  (formula (III)), where u is an integer between 2 and 6.

In various embodiments of the fourth aspect of the invention, NA is covalently linked to at least one SBU via a linker moiety X or a branching moiety W, wherein X, independently for each linker unit, is selected from the group consisting of:

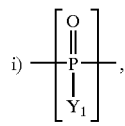

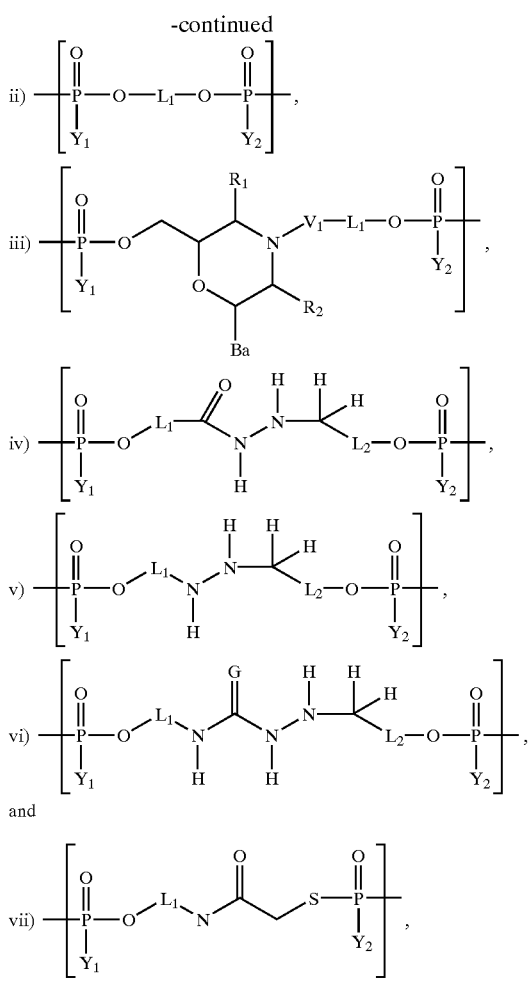

wherein

Y₁, Y₂ are independently of one another OH, SH, NH₂ or CH₃

G is O or S,

L₁, L₂ are independently linkers selected from the group consisting of:

a covalent bond; and a linker chain moiety comprising a saturated or unsaturated, branched or unbranched, substituted or unsubstituted, chain of 1–60 carbon atoms and 0–40 heteroatoms selected from the group consisting of N, O, and S;

V₁, V₂ are independently selected from the group consisting of

—[—CH₂—]—, and

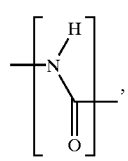

R₁, R₂ are independently of one another H or OH, and
Ba is a nitrogen heterocycle moiety;

and wherein W has the general formula:

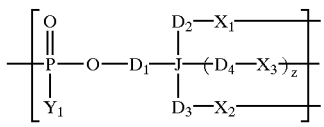

wherein $Y_1$ is OH, SH, $NH_2$ or $CH_3$;

wherein $D_1$, $D_2$, $D_3$, and $D_4$, are, independently, a covalent bond or a linker chain moiety comprising a saturated or unsaturated, branched or unbranched, substituted or unsubstituted, chain of 1 to 10 carbon atoms and 0 to 4 heteroatoms selected from the group consisting of O, S, and N;

wherein J is carbon or nitrogen;

wherein z is 0 or 1, further wherein z is 0 if J is nitrogen; and wherein $X_1$, $X_2$, and $X_3$, are independently X as described above.

In preferred embodiments of the fourth aspect of the invention, W has one of the following general structures:

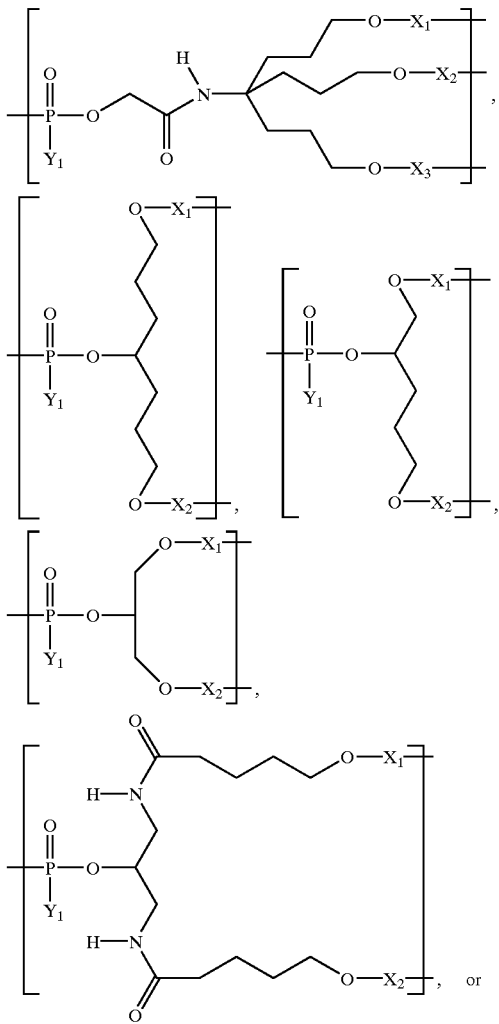

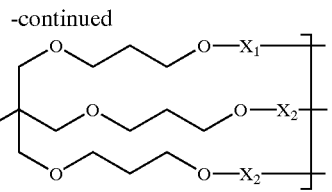

The SBUs and NAs for use in the third and fourth aspects of the invention may be any of those described herein. Preferred SBUs include pRNA, pDNA, and cyclohexyl nucleic acid (CNA). Preferred NAs include DNA, RNA, and their chemically modified derivatives. Labeled embodiments are also preferred.

In a fifth aspect, the present invention provides unit of a synthetic binding system selected from the group consisting of a synthetic binding unit (SBU) and a synthetic addressing unit (SAU), comprising an oligomer of monomeric units, wherein the monomeric units have the general formula

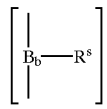

wherein $B_b$ is a backbone moiety which connects the monomeric unit to the oligomer, and wherein $R^s$ is a specific recognition moiety comprising a nitrogen heterocycle moiety, wherein the monomeric units linearly arranged according to the formulae (IX) or (X), $$B_{s1}-(J)-B_{s2} \quad \text{(formula (IX))}$$

$$B_{s1}-(J)-B_{s2}-(J')-B_{s3} \quad \text{formula (X))}$$

wherein s1, s2 and s3 are, independently, an integer between 0 and 10, and B is any monomeric building block as is used for synthesizing the synthetic binding units (SBU), and J is a sequence of recognition moieties ($R^5$), wherein J may be the same or different than J', and wherein the sequences J and J' are, independently, selected from group A consisting of SEQ. ID Nos. 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, and 75, or are selected from the group B consisting of SEQ. ID Nos. 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, and 76, provided that sequences J and J' are selected from the same group.

In preferred embodiments of the fifth aspect of the invention, J and J' are, independently, selected from group A' consisting of SEQ. ID Nos. 3, 5, 7, 9, 11, 13, 15, 17, 19, 21, 23, 25, 27, 29, 31, 33, 35, 37, 39, 41, 43, 45, and 47, or are selected from the group B' consisting of sequences SEQ. ID Nos. 4, 6, 8, 10, 12, 14, 16, 18, 20, 22, 24, 26, 28, 30, 32, 34, 36, 38, 40, 42, 44, 46, and 48, provided that sequences J and J' are selected from the same group. In additional preferred embodiments of the fifth aspect of the invention, J and J' are, independently, selected from group A' consisting of SEQ. ID Nos. 49, 51, 53, 55, 57, 59, 61, 63, 65, 67, 69, 71, 73, and 75, or are selected from the group B' consisting of sequences SEQ. ID Nos. 50, 52, 54, 56, 58, 60, 62, 64, 66, 68, 70, 72, 74, and 76, provided that sequences J and J' are selected from the same group. In more preferred embodiments of the fifth aspect of the invention, J and J' are, independently, selected from group A''' consisting of SEQ. ID Nos. 49, 51, 53, 57, 59, 61, 65, 69, 71, and 75, or are selected from the group B'" consisting of sequences SEQ. ID Nos. 50, 52, 54, 58, 60, 62, 66, 70, 72, and 76, provided that sequences J and J' are selected from the same group.

In preferred embodiments, the SAUs or SBUs are pRNA, pDNA, or CNA. In various embodiments, the fifth aspect of the invention may be sets, libraries, or kits comprising SAUs or SBUs with the disclosed sequences, preferably where the SAUs or SBUs in the sets, libraries, or kits are orthogonal to each other. For instance, kit embodiments may comprise two or more, more preferably at least 5, or at least 10, or at least 20, of the SAUs which are either unmodified or are adapted with functional groups for attachment to a support material. Furthermore, an SAU kit embodiment may comprise the SAUs pre-attached to a support material. In these embodiments preferably between 1 and 100, or between 2 and 20, or between 2 and 10 SAUs are attached to the support at known locations. Or, kit embodiments may comprise two or more, more preferably at least five, or at least 10, or at least 20 of the SBUs which are either unmodified or adapted with functional groups for attachment to NAs. In addition, the SBUs of the fifth aspect of the invention may be utilized in any of the conjugate structures disclosed herein.

In various embodiments of the third, fourth aspects, and conjugate fifth aspects of the invention, libraries may be constructed from several conjugates. The SBU members of the libraries are preferably orthogonal. Libraries comprise at least two, preferably at least five, at least ten, at least twenty, or at least 100 conjugates, depending on the purpose of the library (e.g., a library of conjugate primers for amplifying a set of genetic loci may have 20 conjugates, while a library for the production of a SNP or STR assay array may have over 100 conjugates). In the libraries, each NA may be conjugated to a specific SBU, each SBU may be conjugated to a specific NA, or both. Alternatively, each NA may be conjugated to a set of SBUs, or each SBU may be conjugated to a set of NAs.

In various embodiments of the third, fourth aspects, and conjugate fifth aspects of the invention, supermolecular constructs of immobilized nucleic acids in an array may be constructed from one or more conjugates. These may use any of the SAUs described herein on any of the support materials described herein. Preferred embodiments use an active electronic array as a support. Preferred supermolecular constructs comprise at least five, more preferably at least ten, more preferably at least 100 or at least 1000 conjugates.

In further embodiments of these aspects of the invention, the conjugates are contacted with attached SAUs to form supermolecular constructs on support materials. These methods may be carried out passively or actively (e.g., by electronic addressing on an active electronic array device in preferred embodiments.) In these method-embodiments, the conjugates may be contacted with a sample, preferably a biological sample, either prior to or after contacted with the attached SAUs.

In a sixth aspect of the invention, kits are provided for producing the conjugates of the third and fourth aspect of the invention. These kits comprise one or more SBUs, more preferably at least 5, or at least 10, or at least 20, which have been modified with functional groups for reaction with modified or unmodified nucleic acids to produce the conjugates of the third or fourth aspect of the invention.

In a seventh aspect, the invention provides improved methods for the solid-phase synthesis of phosphate or phosphoramidite moiety linked conjugates. These methods comprise:

a) synthesizing the conjugates on a solid support phase using monomer or oligomer units, wherein the units are p-cyanoethyl-protected on a terminal phosphorus of the units, b) treating the support with a solution of an alkylamine in an inert solvent, c) treating the support with hydrazine to cleave off and deprotect the conjugate.

In preferred embodiments, the alkylamine is a secondary alkylamine, more preferably selected from the group consisting of dimethylamine, diethylamine, dipropylamine, dibutylamine, dipentylamine, dihexylamine, di-N-octylamine, di-N-decylamine, didodecylamine, N-ethylmethylamine, N-methyl-N-propylamine, N-methylbutylamine, N-methylpentylamine, N-methylhexylamine, N-ethylpropylamine, N-(N-butyl)-N-propylamine, N-amyl-N-butylamine, N,N'-di-N-butyl-1,6-hexanediamine, N,N'-dimethyl-1,3-propanediamine, N,N'-dimethyl-1,6-hexanediamine. Most preferred for use is diethylamine.

In an eighth aspect, the present invention provides methods for utilizing the nucleic acid portion of a SBU-NA conjugate, as any of the structures disclosed herein, as a substrate in an enzymatic reaction. In one group of embodiments, the nucleic acid portion of the conjugates is enzymatically modified. In general, these methods comprise:

a) contacting the conjugate with at least one enzyme which utilizes naturally occurring nucleic acids as a substrate, and with other reagents necessary for the action of the enzyme; and b) incubating the mixture obtained in a) under conditions suitable for the functioning of the enzyme for a period of time sufficient to effect the modification of the conjugate.

In various embodiments, various reagents may be utilized in step a), including nucleoside triphosphates (e.g., plain, labeled, chemically modified) and/or template or art target nucleic acids (e.g., plain, labeled, chemically modified). In various embodiments, % more than one enzyme may be employed in step a). In one preferred embodiment, the enzyme is a ligase enzyme, and the nucleic acid portion of the conjugate is ligated to a target nucleic acid. In another preferred embodiment, the enzyme is at least one polymerase, and a template nucleic acid sequence is amplified using the conjugate as a primer. In a particularly preferred version of this embodiment, the amplification is a linear or exponential thermal cycling amplification. In another preferred embodiment, the enzyme is a mixture of enzymes comprising a restriction endonuclease activity and a polymerase activity, and a template nucleic acid sequence is amplified isothermally utilizing a conjugate as a primer. In particularly preferred versions of this embodiment, the conjugate is immobilized, and the amplification is an anchored SDA reaction.

In other embodiments of the eight aspect of the invention, the conjugate is utilized as a substrate hybridized to a target nucleic acid, wherein the nucleic acid hybridized to the conjugate is modified by the enzyme. Preferred embodiments include the degradation of an target RNA strand by RNAse H while hybridized to a conjugate, and the cleavage of a target nucleic acid strand by a restriction endonuclease while hybridized to a conjugate.

BRIEF DESCRIPTION OF THE FIGURES

FIG. 1A shows the linkage of a nucleic acid via its 3' end to the end of the SBU which points away from the support when paired with the SAU. FIG. 1B shows the linkage of a nucleic acid via its 5' end to the end of the SBU which points away from the support. FIG. 1C shows the linkage of a nucleic acid via its 5' end to the end of the binding unit which points towards the support. FIG. 1D shows the linkage of a nucleic acid via its 5' end to a position in the center of the binding unit. An example of this type of linkage would be a the conjugation of a tryptamine base linker in a pRNA with an aldehyde on the end of a nucleic acid.

FIG. 3A shows the helical form of nucleic acid duplexes on the basis of a B-DNA helix. FIG. 3B shows the non-helical nature of synthetic binding systems such as pRNA, pDNA, and CNA. FIG. 3C shows the example of a binding unit (SBU) 102a and address unit (SAU) 102b. NA=nucleic acid; SM=support material; in this example, the address 102b is immobilized and 102a is conjugated with the nucleic acid (NA) via a linker. The inter-strand base stacking interactions (stacks) are shown using the example of purine—purine base stacking interactions (Pu—Pu stack) and of purine-pyrimidine base stacking interactions (Pu-Py stack). 0 stack means the absence of such a base stacking interaction. The pyrimidine-purine stacks possible in principle are not present in this specific example.

FIG. 7A illustrates the immobilization of nucleic acids (NA) which are linked via a branching site (BS) to a plurality of identical binding units for the immobilization on support materials (SM). FIG. 7B shows the use of two different synthetic binding systems (SAU1 and SBU1 and also SAU2 and SBU2) for the immobilization of a nucleic acid through a branching structure. An advantage of these structures in the increased, additive binding energy immobilizing the nucleic acid.

FIG. 11B shows that for immobilizing a nucleic acid (NA) on a support material (SM) SBU (here pRNA) and SAU (here CNA) need not belong to one molecular class. Any sterically compatible molecules which form a stable and selective immobilization upon recognition are suitable for use in these formats.

In the preferred embodiment, mixtures of N different conjugates (or SBU-encoded groups of conjugates) are addressed to N array positions, and this addressing can be carried out sequentially or parallel to all N positions. These sets may contain N different nucleic acids (v, w, x, y, . . . N) all of which are conjugated with an individual synthetic binding unit (a', b', c', . . . N). The specific recognition of the fixed synthetic address unit by the binding units leads to only that type of nucleic acid, which has been conjugated with the corresponding synthetic binding unit complementary to the fixed binding unit, being immobilized on each array position. In other words, the set of conjugates is sorted to specific locations. Thus, in a single process step N different conjugates (a'-v1, b'-w1, c'-x1, d'-y1, . . . N) are immobilized. Although a row/column addressing scheme is shown here, other geometries are possible. After the binding of each set of conjugates to each activated set of locations, the unbound conjugates are removed. This procedure can then be repeated using a new second set of conjugates (a'-v2, b'-w2, c'-x2, d'-y2, . . . N). In each repetition, again up to N conjugates are immobilized in parallel. Thus, after M repetitions, W different conjugates are immobilized on the array, with W=N×M.

Figure 13:
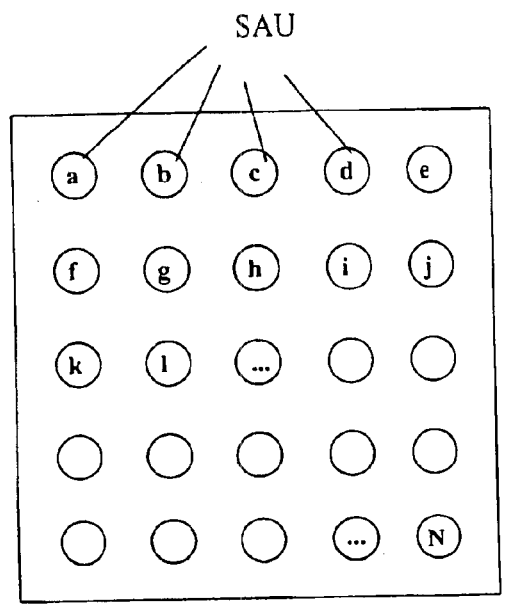
Figure 13:
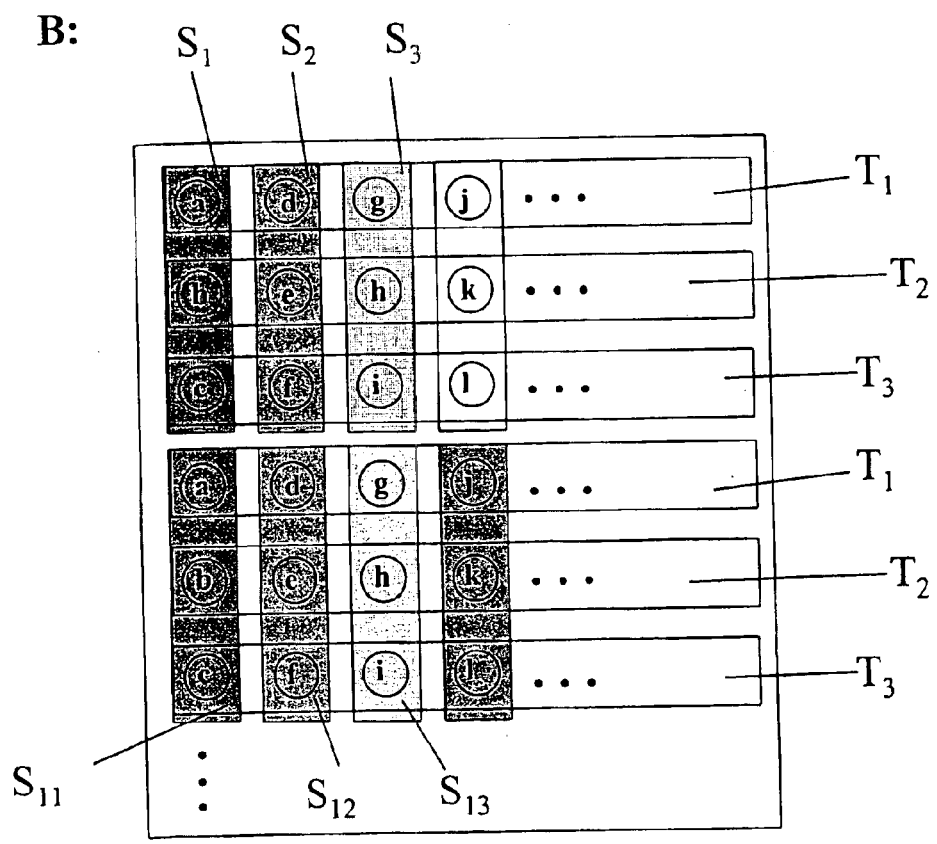

FIG. 13: shows further embodiments for using synthetic binding systems for the immobilization of nucleic acids on support material. FIG. 13A shows an example of an array of N different address units. In additional embodiments, one may wish to attach individual address units two or more times to different array positions for duplicate addressing at those positions. This embodiment is typical for passive arrays, although it may be utilized in active location array systems as well. FIG. 13B shows, by way of example, an embodiment for using synthetic binding systems for generating arrays of nucleic acids for the analyses of different samples of nucleic acids, as can be applied to gene expression studies. Here, different times, stages or populations of nucleic acids, for example particular gene probe sequences which have been hybridized to different samples, are compared with one another on an array. Here, by way of example, the immobilization of three times T1, T2, T3 of various nucleic acid sequences (genes; S1, S2, S3, . . . ) is depicted. Initially, an array of fixed synthetic address units is prepared. Times to be compared may thereafter by differentiated by particular sets of SBU's conjugated with the set of nucleic acid sequences to be monitored. The times to be compared of may be allowed to associate with the SAU's either simultaneously or sequentially. The specific recognition of synthetic address units by the synthetic binding units immobilizes on each array position only the conjugate specifically belonging to the position, thus locating the sample nucleic acids hybridized according to the SBU utilized. An advantage to simultaneous addressing of several samples at one once is that variability in hybridization conditions caused by the individual incubation of the samples with the array may be avoided, allowing for more rigorous and quantitative comparison of the results. In addition, the ability to assay multiple samples in one cycle saves time compared with individual addressing, or hybridization with separate arrays.

Figure 14:
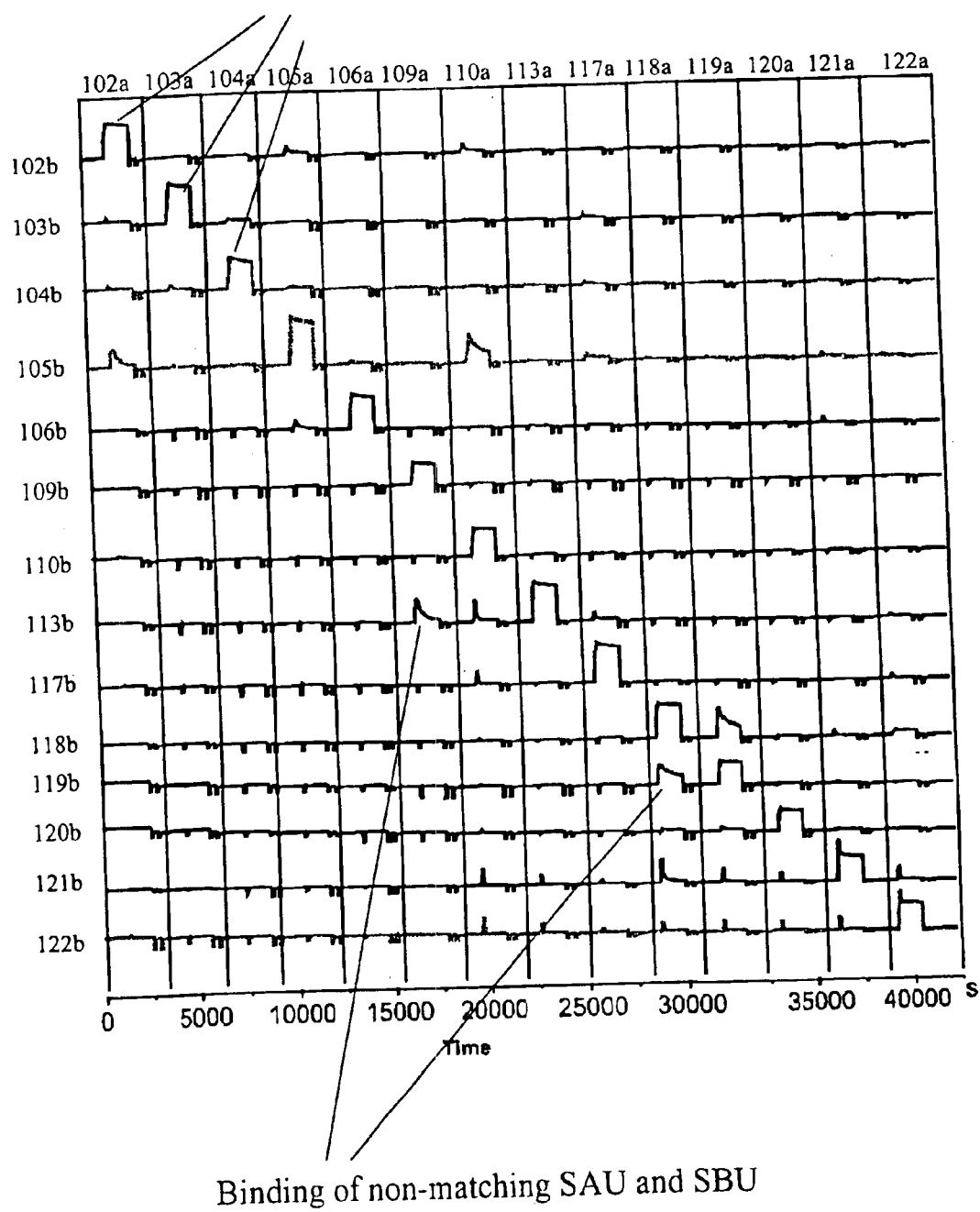

FIG. 14: A graph of the result of a surface plasmon resonance experiment (SPR) in which 14 synthetic address units are contacted with 14 synthetic binding units.

The signal increasing from the baseline upward indicates binding. As expected, all address units bind to the in each case corresponding specific binding unit (e.g. 102a to 102b). Some address units and binding units, however, show some degree of cross-association with units which are not exactly complementary (e.g. 105b with 110a). Sets of binding units in which such cross-association reactions are substantially reduced are said to be "orthogonal". Although suitable for some uses, non-orthogonal units should not be used together in one set of synthetic binding systems when strict sorting according to the addressing units is desired.

Figure 15:
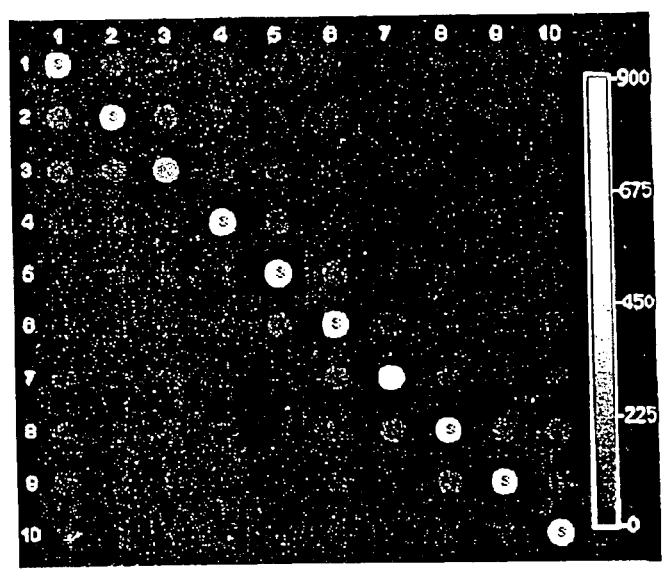

FIG. 15: A photograph and chart of the specific association of fluorescently labeled binding units to synthetic address units attached to the surface of an active electronic array. The strongest fluorescence signals are all on a diagonal with the specific SBU-SAU pairs, as expected.

Figure 16:
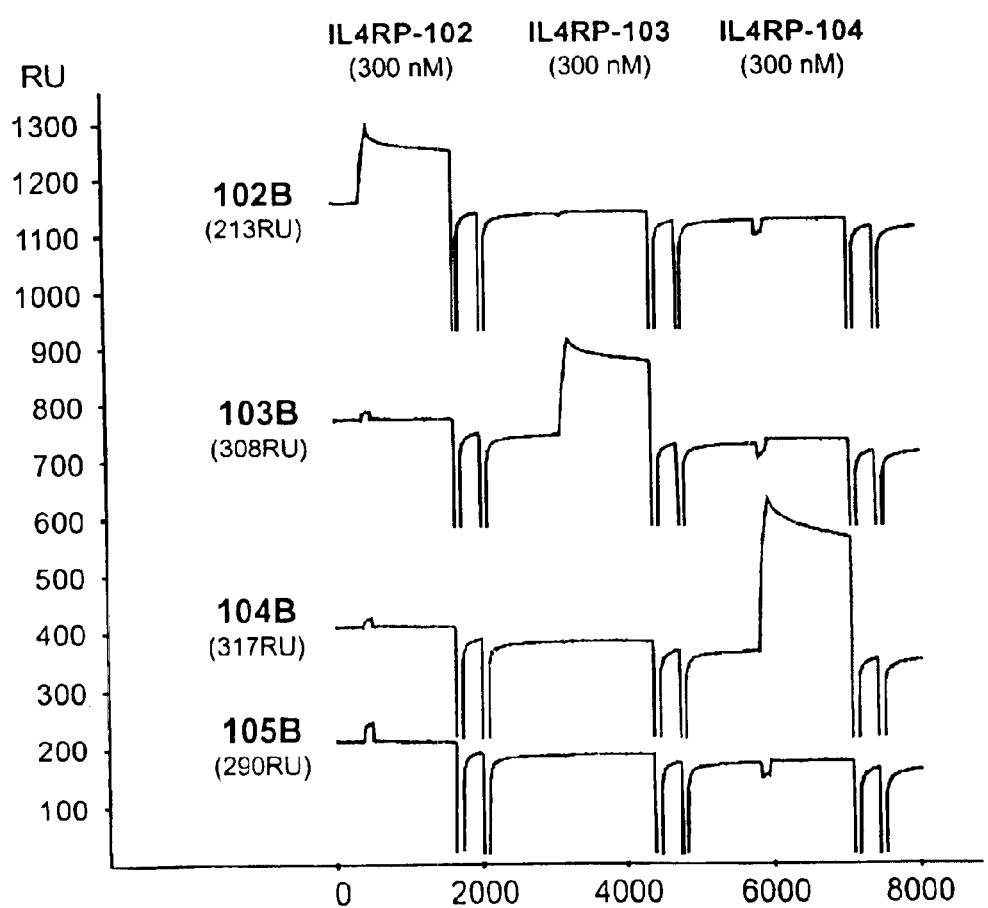

FIG. 16: A chart of the association of conjugates of nucleic acids (C) and pRNA/SBUs with pRNA/SAU's attached to the surface of the SPR chip, also demonstrating specific binding between the coordinating pairs. 4' biotinylated 102b, 103b, 104b, and 105b, prepared as in Example 2.1, were immobilized on the Sensor Chip channels as described in Example 8. Conjugates IL4RP102a, IL4RP103a, and IL4RP104a, prepared as in Example 1.1, were then sequentially assayed for binding to the SAUs in the channels.

Figure 17:
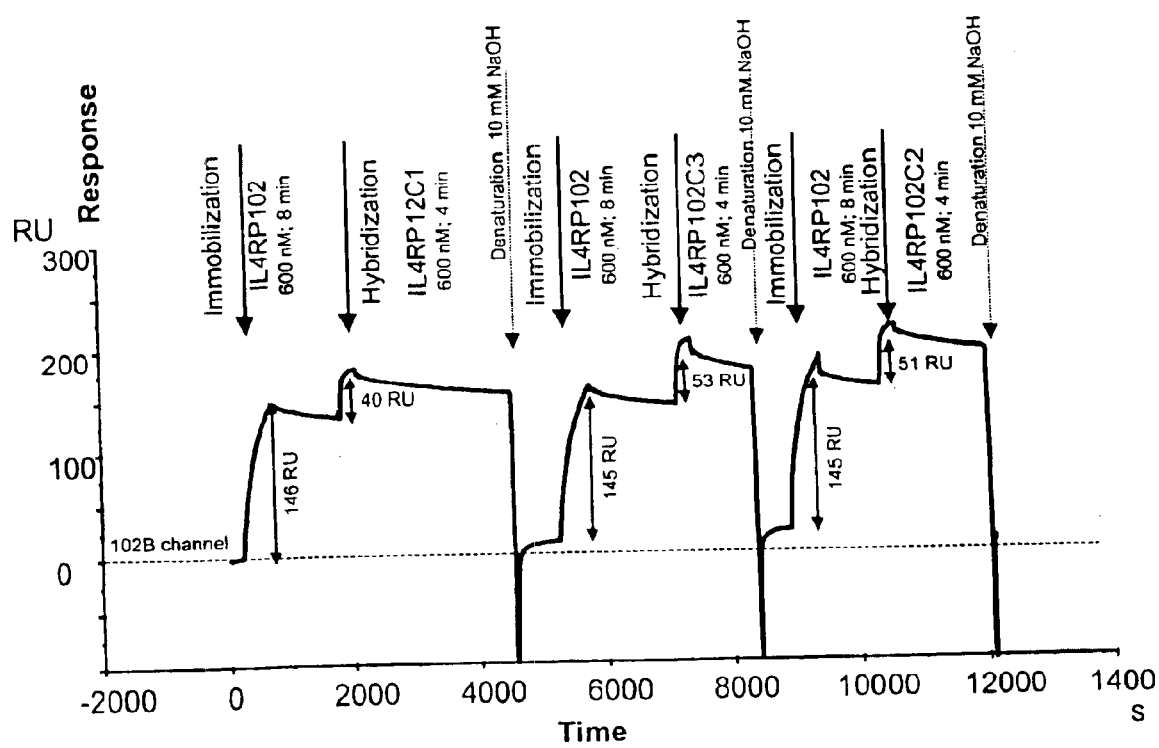

FIG. 17: A chart of the immobilization of a conjugate IL4RP102a (Example 1.1) by biotinylated synthetic address unit 102b (Example 2.1) on an SPR chip and subsequent hybridization of the nucleic acid part of the conjugate with three complementary DNA fragments. IL4RP102C1 was a complementary sequence to all but the 5' three nucleotides of the NA portion of IL4RP102a, IL4RP102C2 was a full complementary sequence, and IL4RP102C3 was a full complementary sequence plus three nucleotides. This experiment also illustrates the ability of the attached SAUs to be utilized repeatedly by simply stripping of the bound SBU conjugates with a mild base solution (e.g. 10 mM NaOH).

Figure 18:
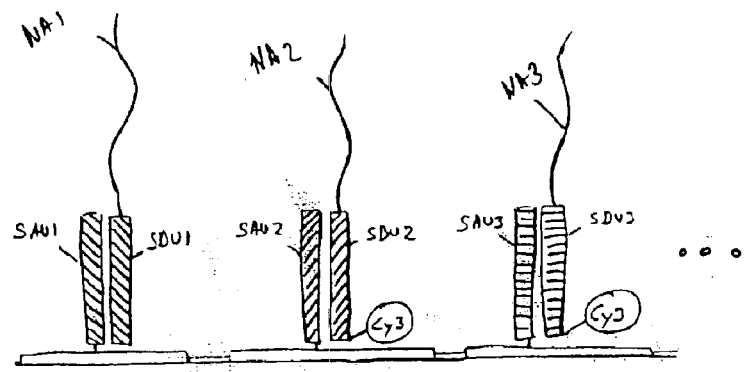
Figure 18:
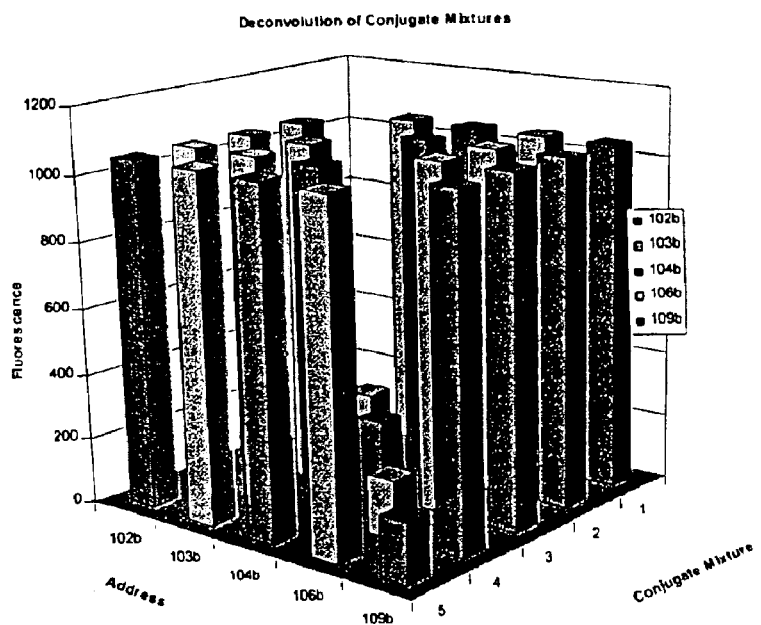

FIG. 18: A diagram of the setup and negative photographs of the results of the Example 5.2. Mixtures of cy3 labeled and one unlabeled synthetic binding unit-nucleic acid conjugates (SBU-NA) are addressed on an active electronic array. Each conjugate is immobilized to the position with the matching synthetic address unit (SAU). The fluorescence measured is displayed as a diagram and a chip image.

Figure 19:
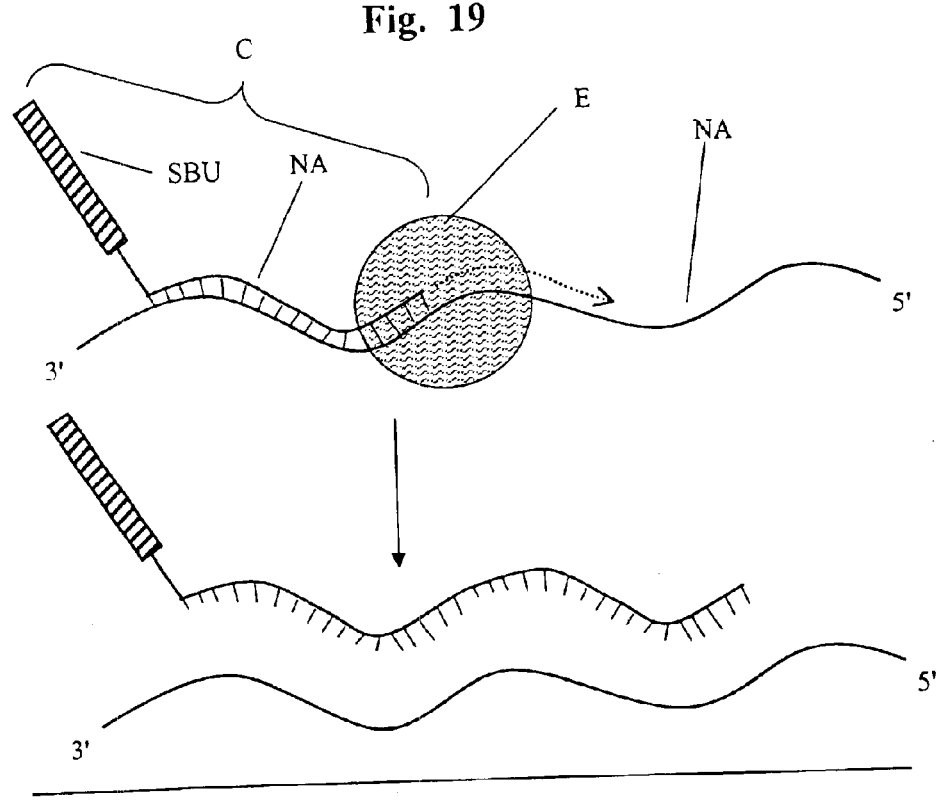
Figure 19:
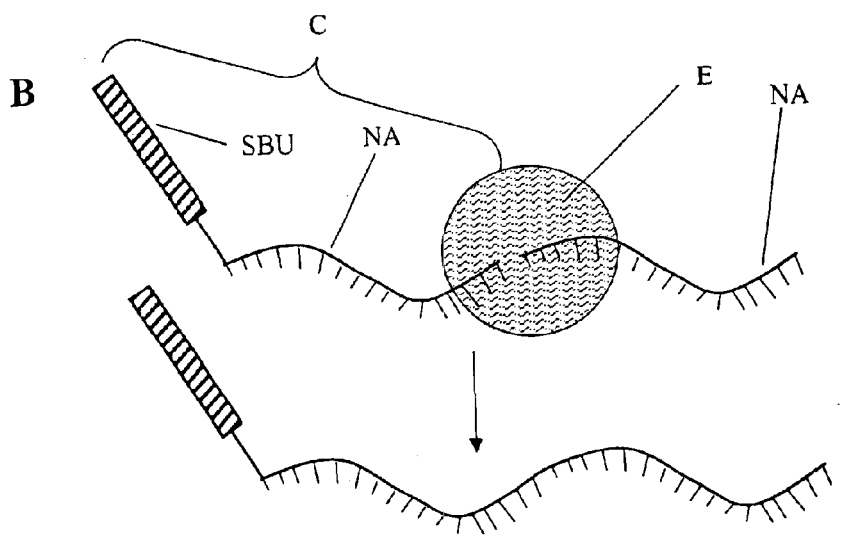

FIG. 19: 19A: a diagram of the use of a conjugate (C) of a synthetic binding unit (SBU) and a nucleic acid section (NA) as the substrate (primer) for a polymerase (E) which carries out a nucleic acid template-dependent synthesis, a first step in amplification reactions. 19B: a diagram of the use of a conjugate (C) of a synthetic binding unit (SBU) and a nucleic acid section (NA) as the substrate of a single-strand ligase (E) which links the conjugate to a nucleic acid. Although shown with a relatively long NA section on the conjugate, ligase reactions may utilize conjugates with just a single nucleic acid residue.

Figure 20A:
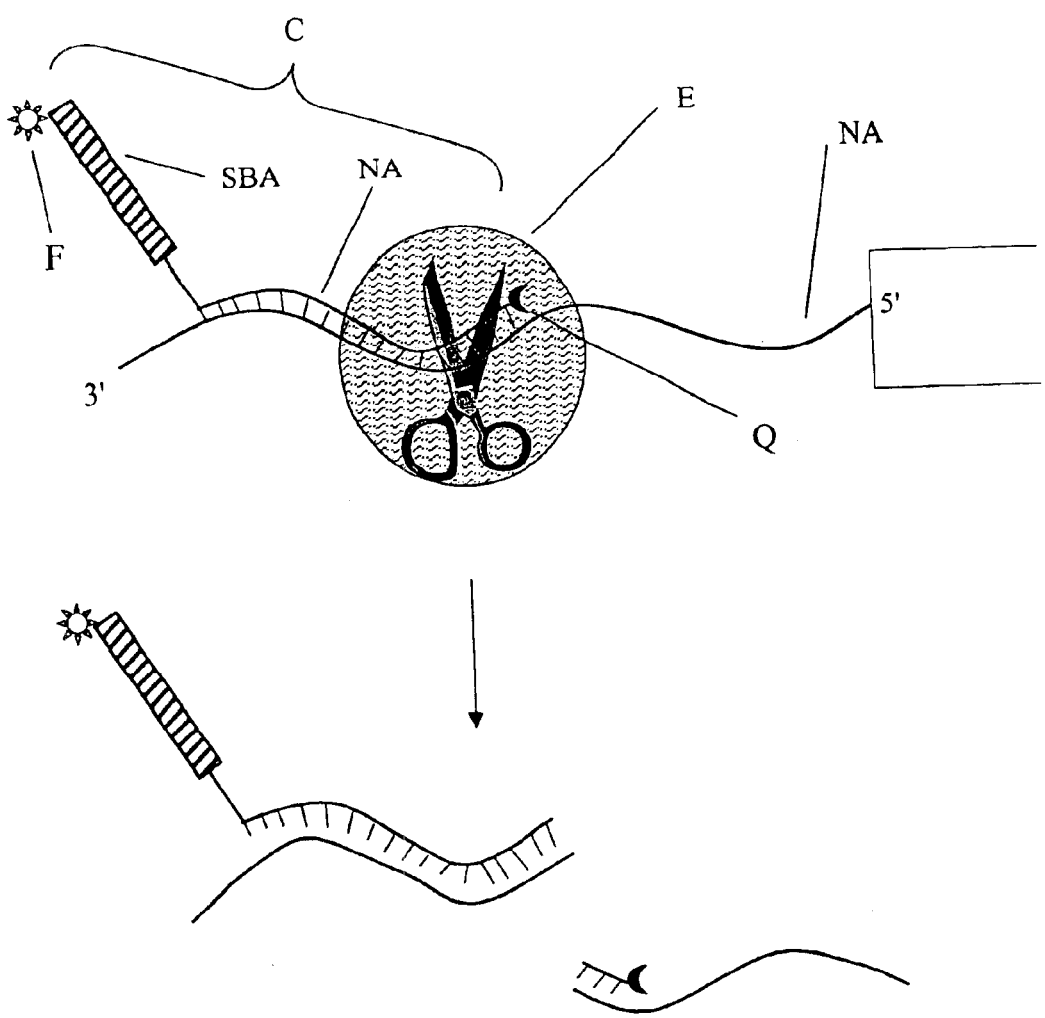

FIGS. 20A & B: Diagrams of the use of a conjugate (C) of a synthetic binding unit (SBU) and a nucleic acid section (NA) as substrates for nuclease reactions. A: The conjugate and a target nucleic acid are cleaved in a restriction endonuclease (E) reaction. This reaction can be especially useful when coupled with fluorescent energy transfer labeling, as shown here. The emissions of a fluorophore moiety (F) may be masked by placing a quencher moiety (O) on the same conjugate. After cleavage, emissions of the fluorophore are no longer absorbed by the quencher, and become visible. The progress of this reaction may be quantified dynamically (real time), or after completion, in order to quantify the amount of the target in the sample. B: The target nucleic acid is selectively degraded by an endonuclease (E) when hybridized to the conjugate nucleic acid portion. This can be especially useful for degrading RNA target nucleic acids with double-stranded specific RNAses, such as RNAse H.

Figure 21:
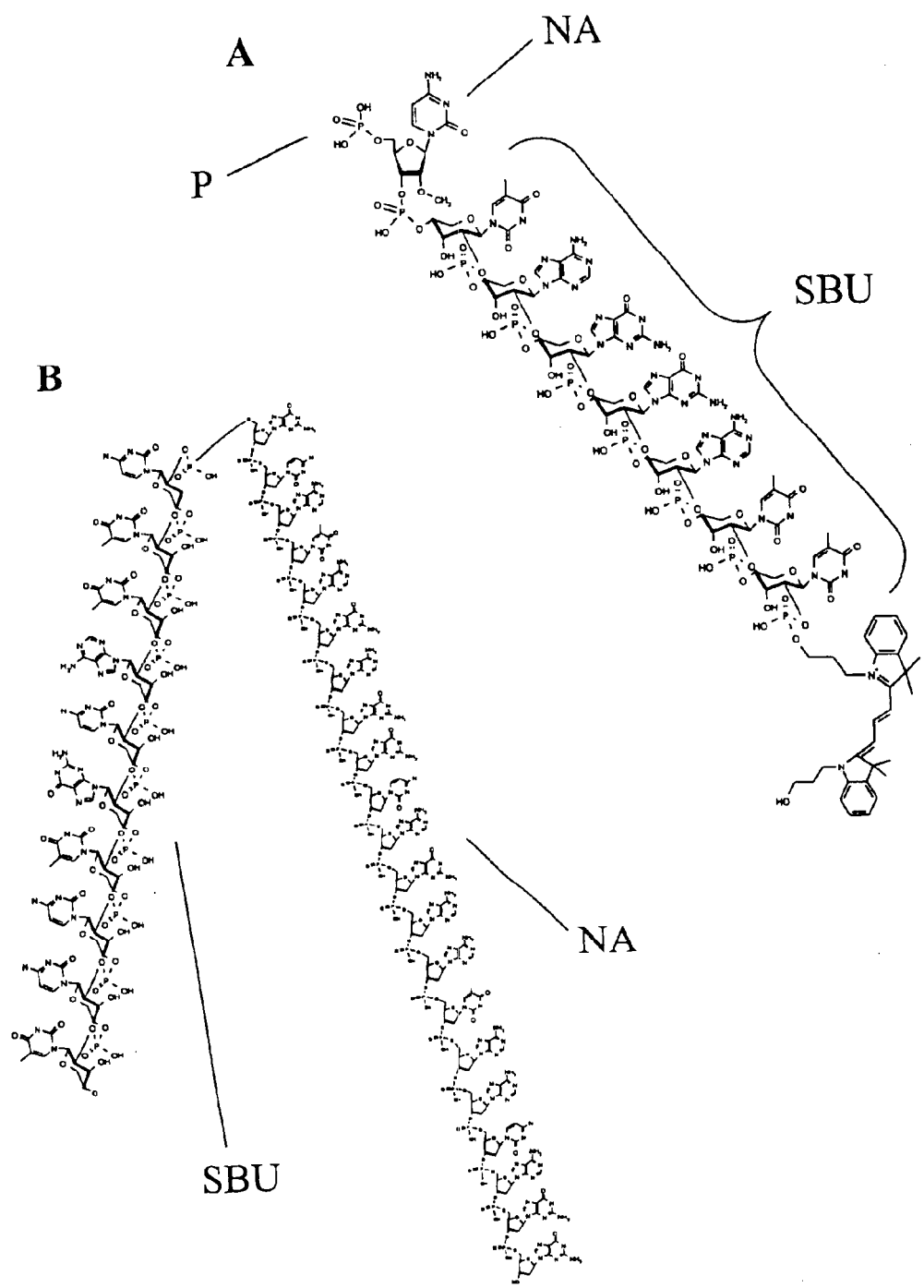

FIG. 21: An illustration of representative pRNA-DNA conjugates. A: a NA/SBU conjugate of a pRNA (SBU) with 2'-OMe-RNA (NA) and 5' phosphate (P) (a suitable substrate for a ligase reaction); the conjugate additionally carries a fluorescence dye at its 3' end. B: a NA/SBU conjugate of a pRNA unit (SBU) and a DNA (NA) with free 3' end (a suitable substrate for a polymerase or restriction endonuclease reaction.)

Figure 22:
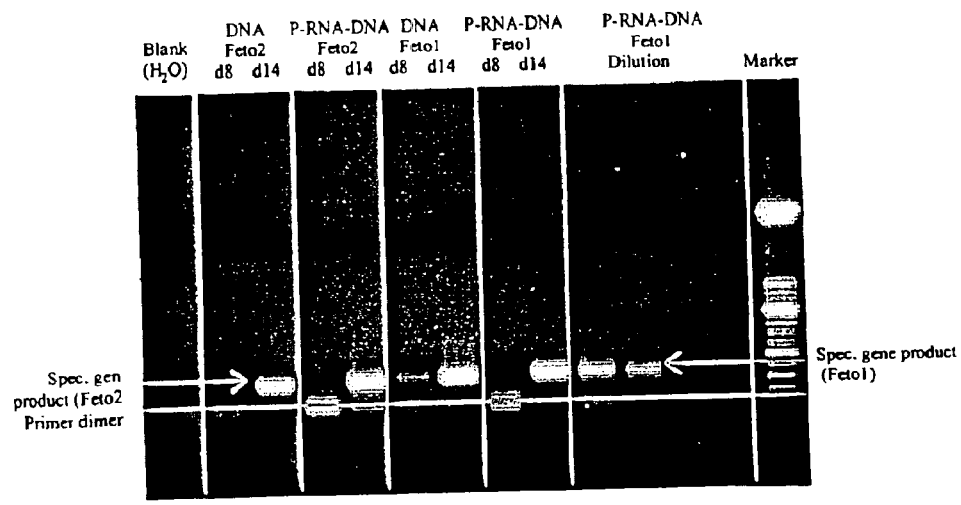
Figure 22:
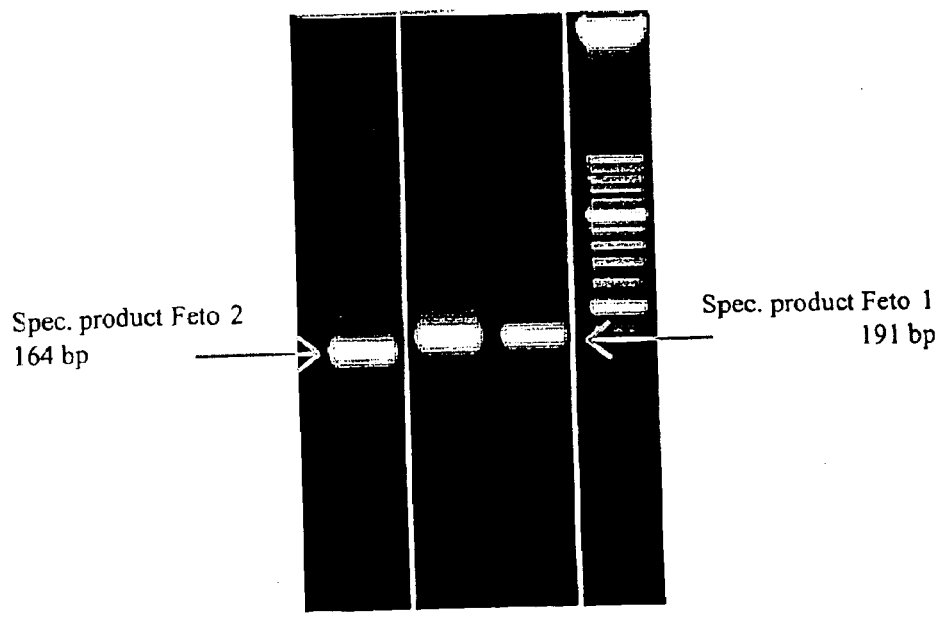

FIG. 22: A: a photograph of an agarose gel showing the formation of specific of amplification products in a PCR reaction using pRNA-DNA conjugates as primers. For comparison, mixtures using standard DNA primers were also applied (see Example 2). B: another photograph of an agarose gel showing the result of a large-scale PCR reaction using NA/SBU conjugates as primers (see Example 3).

Figure 23:
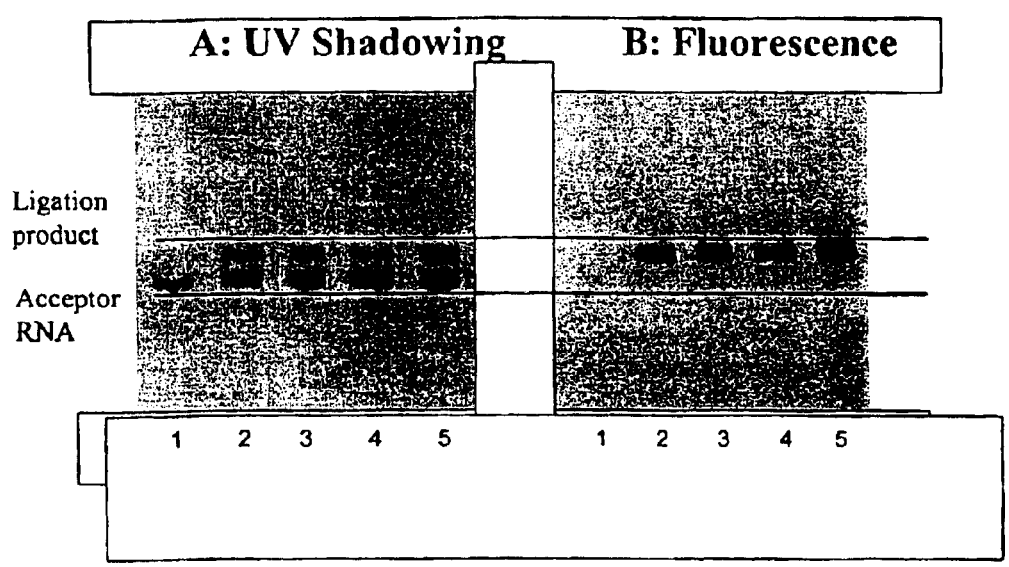
Figure 24:
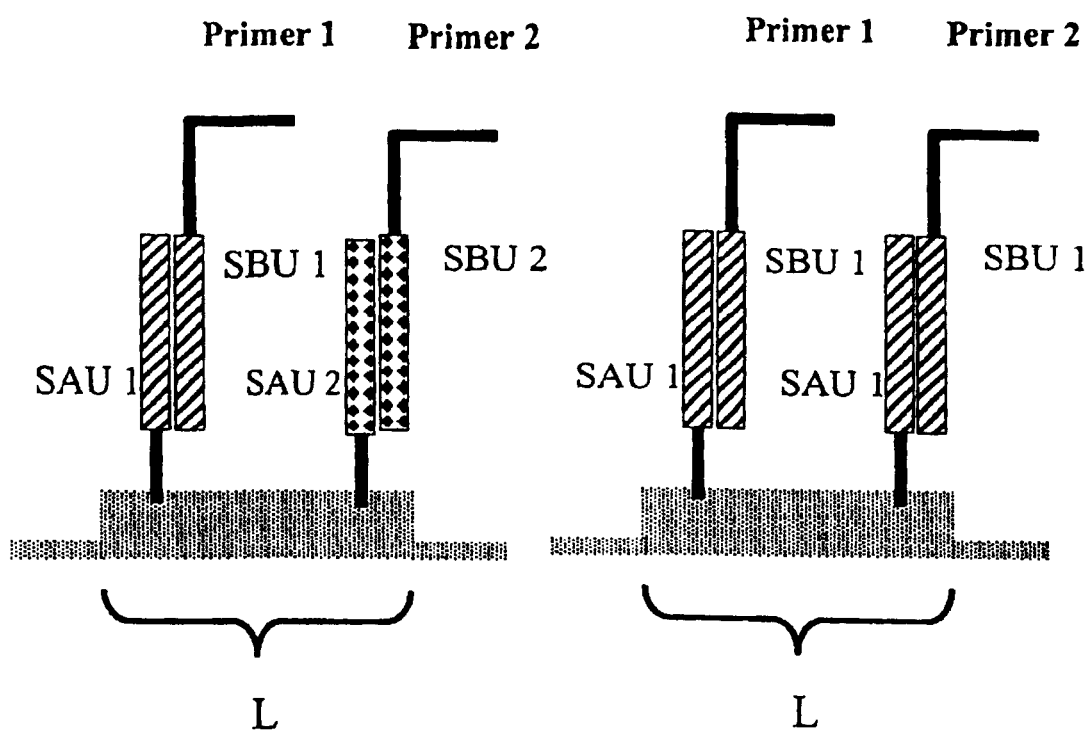

FIG. 23: A photograph of a 10% polyacrylamide gel showing the products of ligation of a fluorescence-labeled conjugate of pRNA and 2'-OMe-RNA with a target RNA, under both UV shadowing and fluorescence imaging. Due to its short length, the free unligated NA/SBU conjugate is not displayed on the gel (see Example 4). The Lanes of the gels are as follows:

Lane 1: Acceptor RNA (negative control)
Lane 2: Ligation mixture with 100 pmol of acceptor RNA and 300 pmol of pRNA hybrid
Lane 3: Ligation mixture with 100 pmol of acceptor RNA and 1000 pmol of pRNA hybrid
Lane 4: Ligation mixture with 100 pmol of acceptor RNA and 300 pmol of pRNA hybrid
Lane 5: Ligation mixture with 100 pmol of acceptor RNA and 1000 pmol of pRNA hybrid FIG. 24 An illustration showing, schematically, an array of SAU on locations (L) to which a series of distinct SDA primers have been addressed via the interaction between the SAU and SAU.

Figure 25:
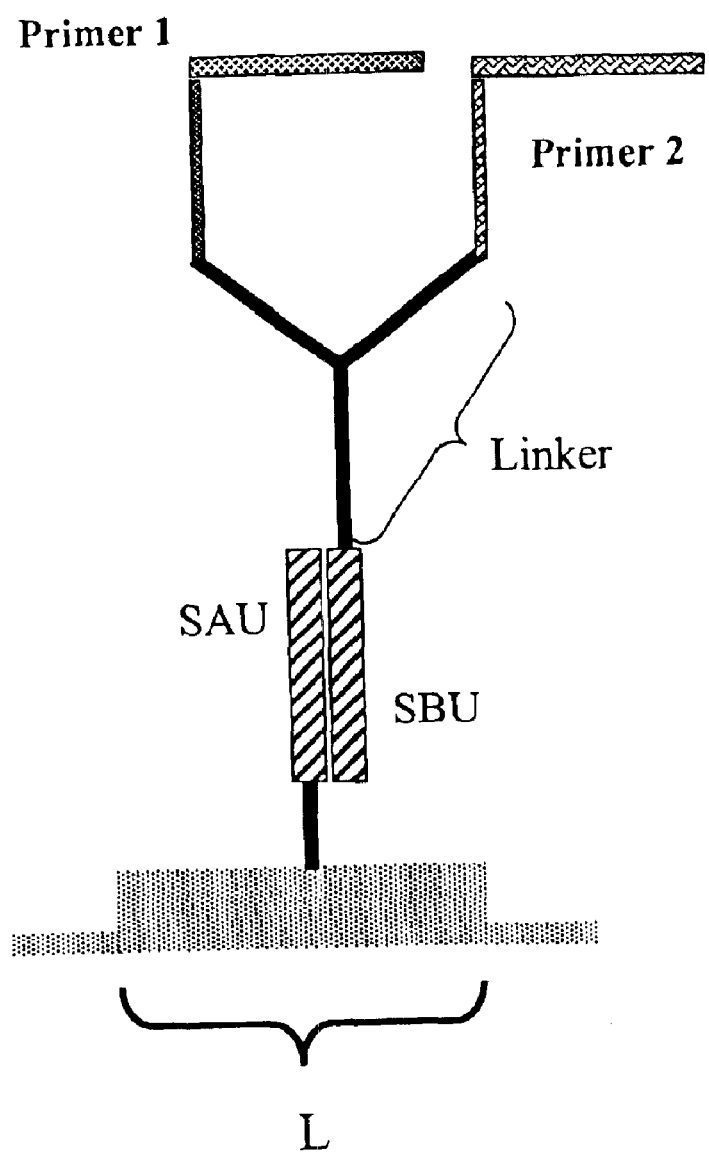

FIG. 25: An illustration showing that that two different primers can be addressed using a single SBS by using a branched linker to attach the primers to one SBU.

Figure 26:
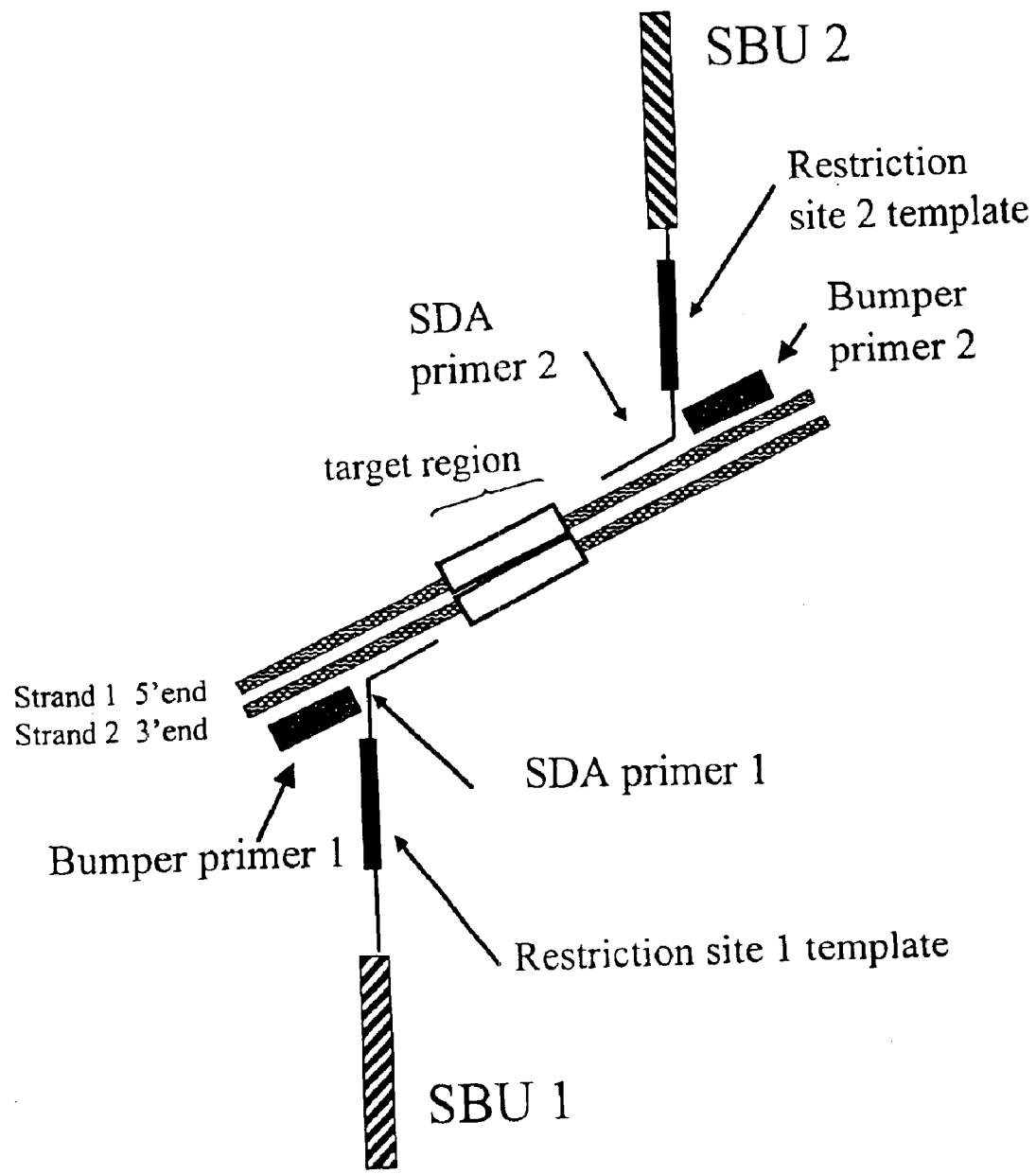

FIG. 26: An illustration showing that shows the general architecture of the SBU anchored SDA construct. The SDA primers contain a restriction site template and a region complementary to the target DNA. The bumper primers are sequences complementary to a region of the target DNA upstream of where the SDA primer binds. The bumper primers form the initiation sites for the polymerase and lead to the initial strand displacement of the target nucleic acid from the extended primer.

Figure 27A:
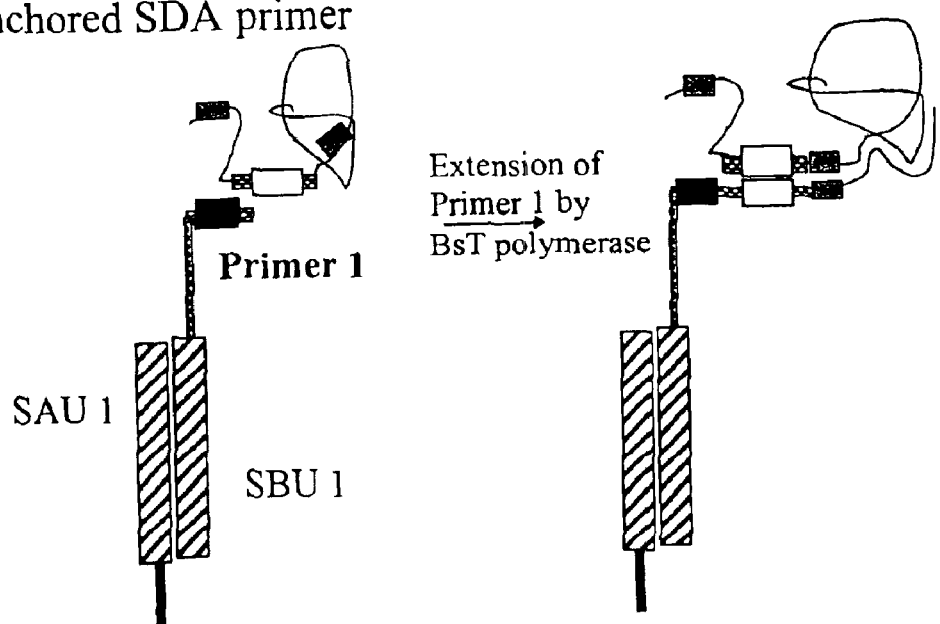
Figure 27A:
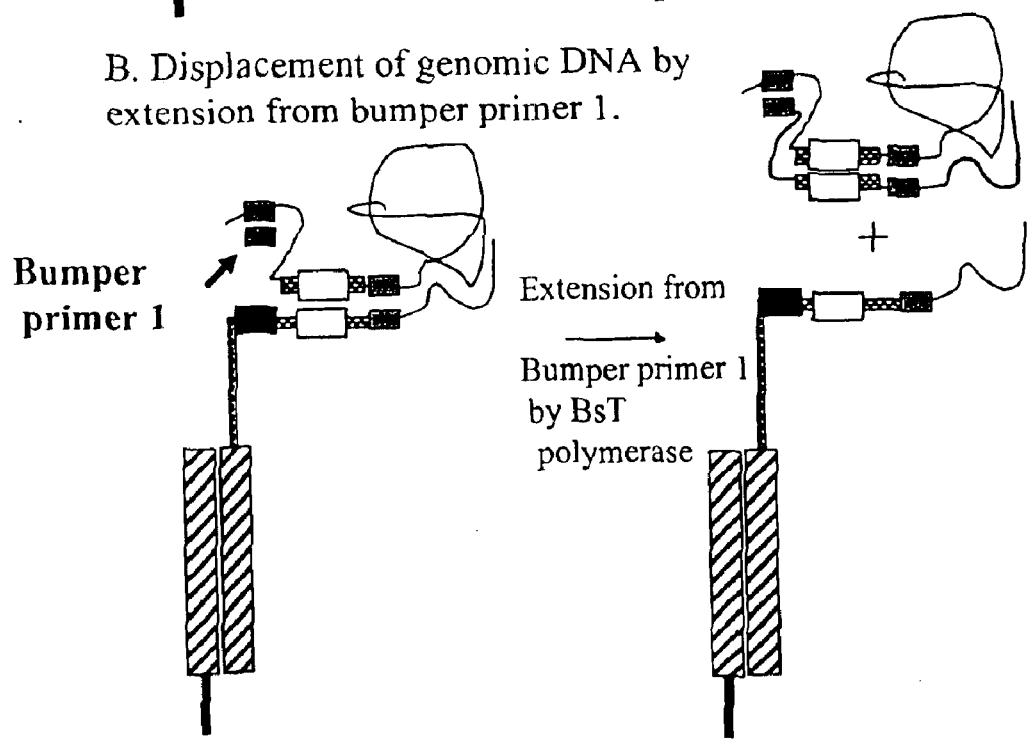
Figure 27B:
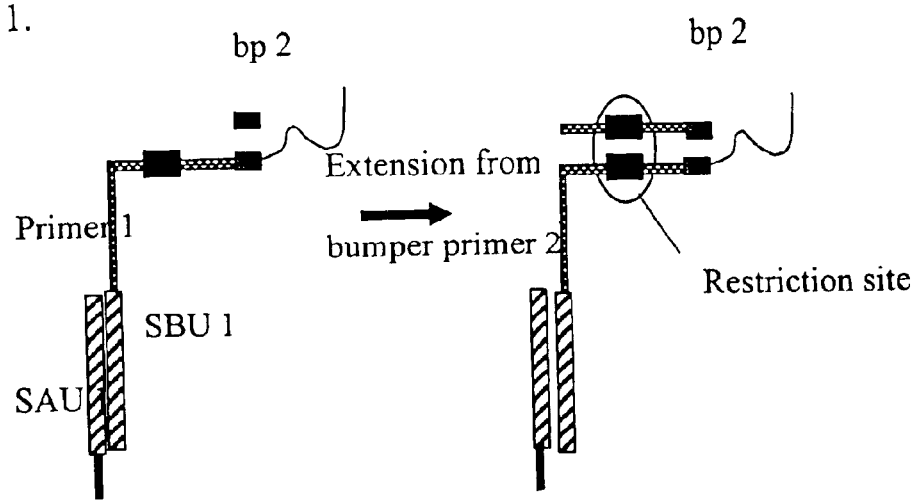
Figure 27B:
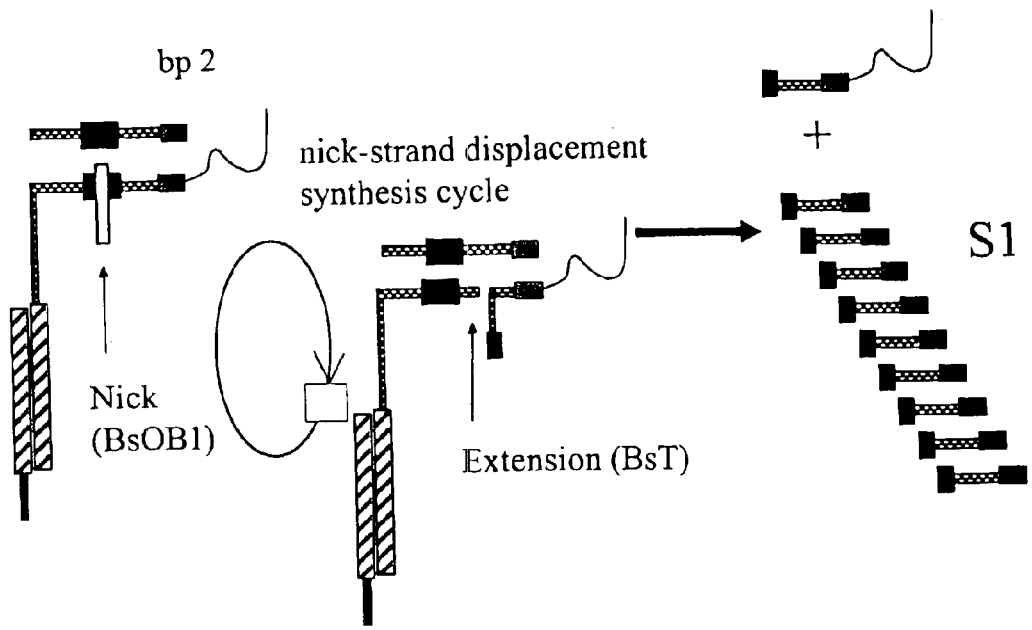

FIGS. 27A and 27B: An illustration of the initiation steps for SBU-anchored SDA (phase 1): Copying of the target sequence onto the SBU-anchored SDA primer, Displacement of the genomic DNA by extension from bumper primer 1, Activation of the restriction site, and Generation of displaced S1 strands.

Figure 27C:
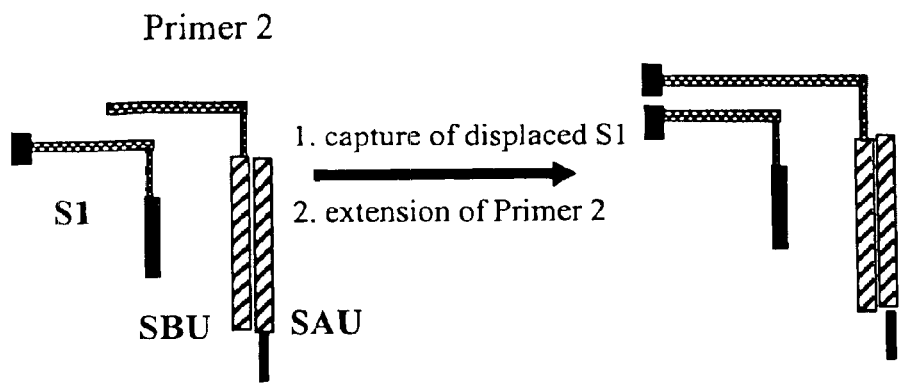
Figure 27C:
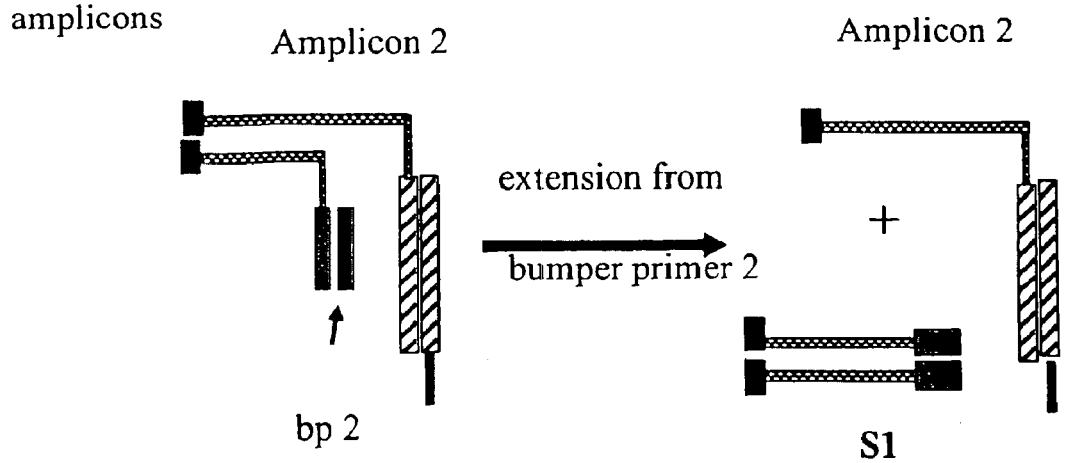

FIG. 27C: An illustration of the linear amplification reactions of SBU anchored SDA (phase 2): The generation of a single stranded anchored amplicon for every Phase 1 displaced strand captured.

Figure 27D:
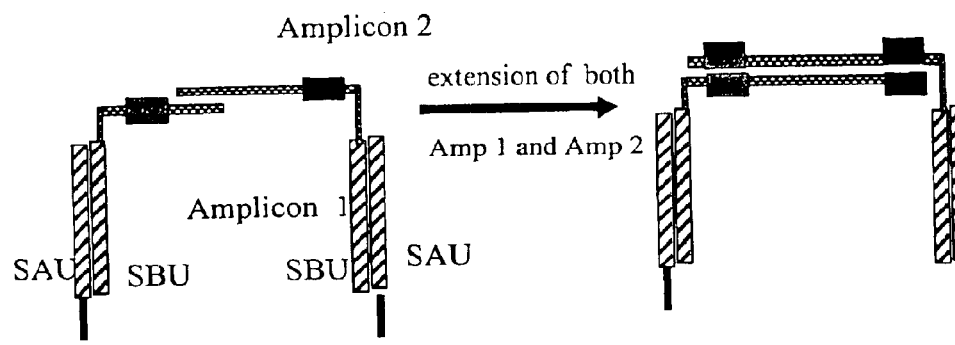
Figure 27D:
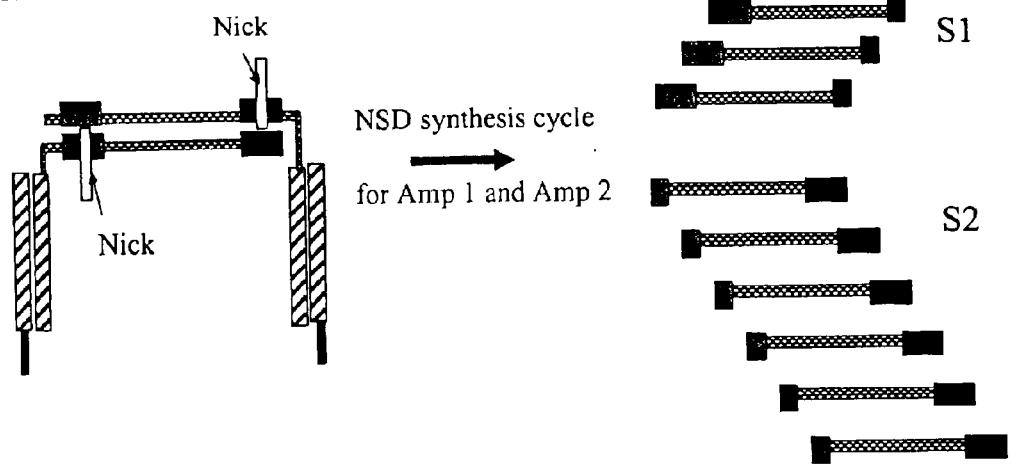
Figure 27E:
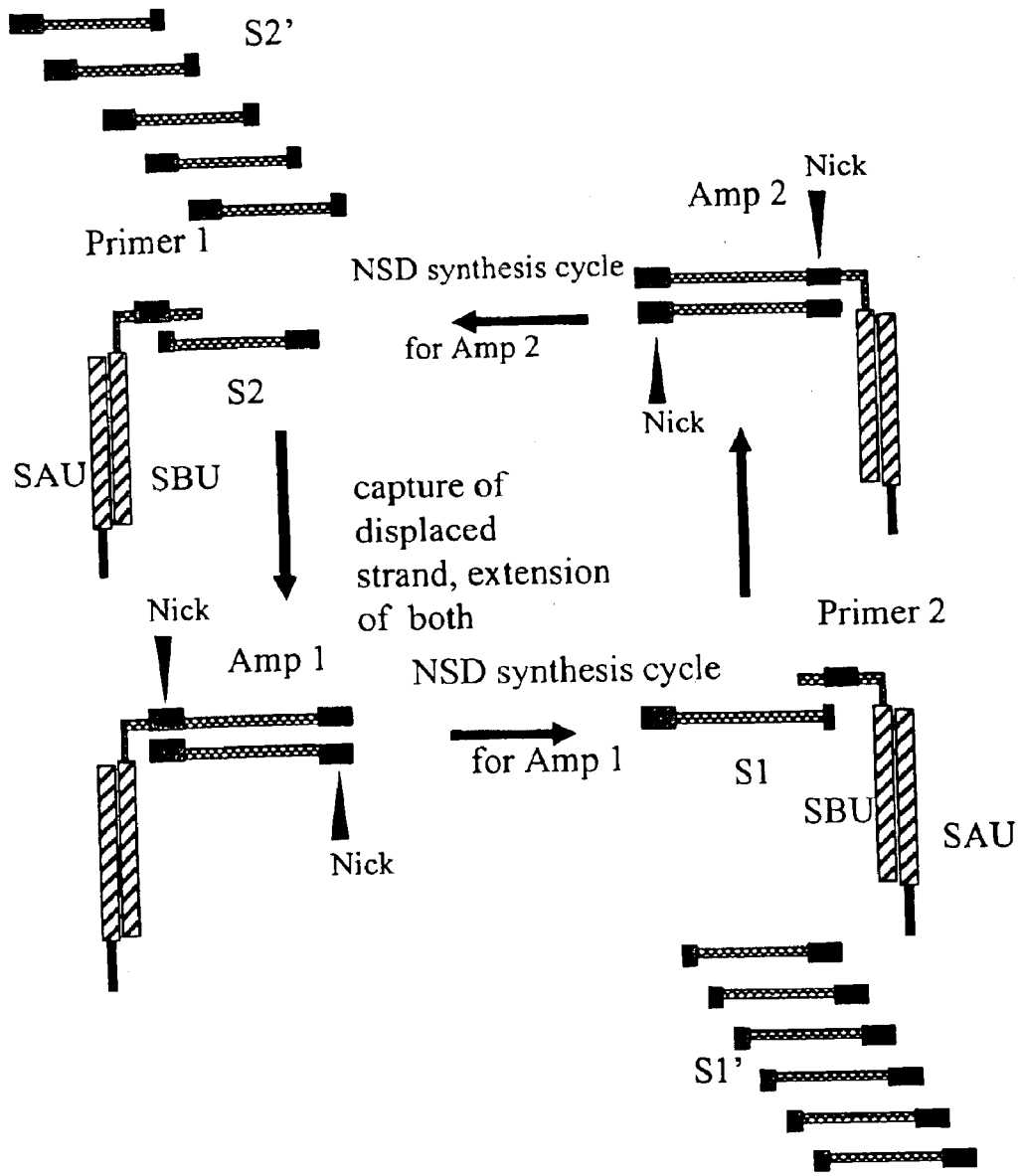

FIGS. 27D and 27E: An illustration of the exponential amplification reactions of SBU anchored SDA (phase 3): Activation of restriction sites in both anchored amplicons, Generation of displaced S1 and S2 strands, and exponential amplification via bridging and capture.

Figure 28:
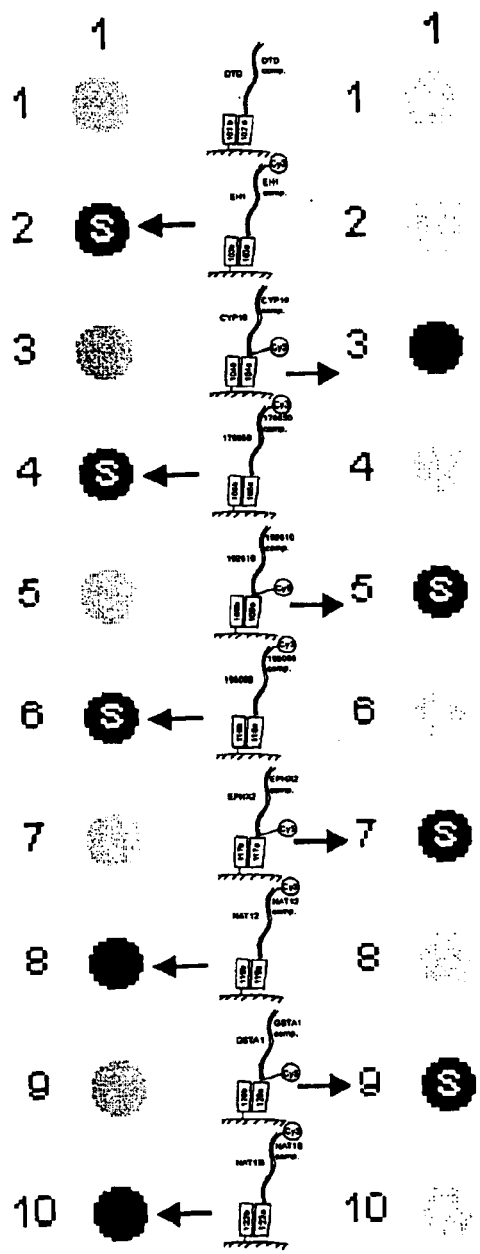
Figure 28:
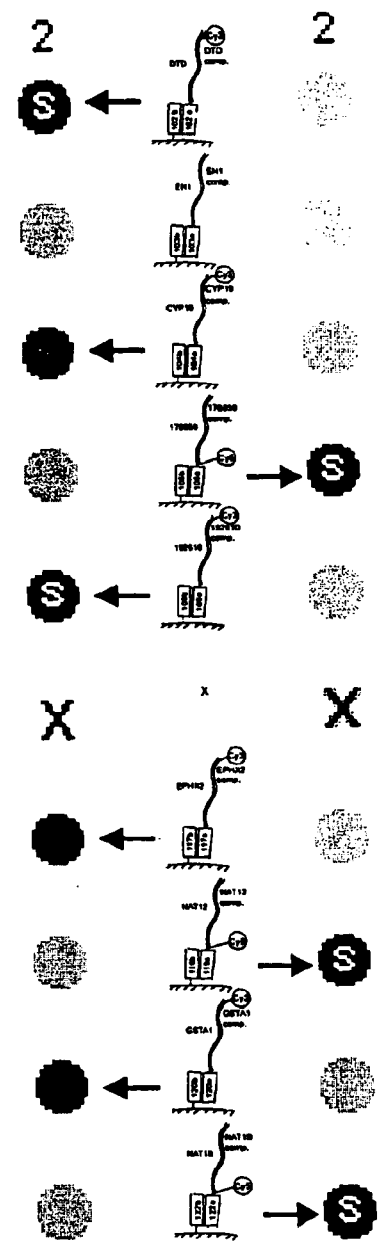

FIG. 28: An illustration of the specific addressing experiment described in Example 5.3. The first two columns of addressed, immobilized nucleic acid/SBU conjugates and hybridized labeled nucleic acids are illustrated by the small figures under the headings "Column 1" and "Column 2". The green fluorescent signal is shown to the left, and the red fluorescent signal is shown to the right, for each of the two columns. Note that this experiment demonstrates that there is no significant hybridization of the complementary sequences to non-activated locations within the array, allowing one to effectively isolate hybridization reactions using the same sequences from different samples at different locations.

DETAILED DESCRIPTION OF THE INVENTION

Applicants have demonstrated a number of improvements in the production and use conjugates comprising at least one nucleic acid (NA) and at least one synthetic binding unit (SBU), wherein the synthetic binding unit is able to specifically recognize a synthetic molecular address unit (SAU) attached to a surface. The specific recognition of SBUs by SAUs can lead to constructs which include a synthetic binding system (SBS) composed of a synthetic binding unit and a synthetic address unit. From this basic idea for a nucleic acid immobilization system, many variations of immobilized nucleic acid arrays may be realized. These include both passively and actively assembled arrays of immobilized nucleic acids which differ in terms of sequence, origin (e.g., from different samples), type (RNA, DNA, etc.), or in other ways. By utilizing the disclosed synthetic binding systems, relatively complex mixtures of nucleic acids can efficiently and specifically be sorted to predetermined locations on a support for facile analysis or further use in nucleic acid based biological assays.

Conjugates for Use in the Present Invention

Thus the basis of present invention are conjugates comprising at least one nucleic acid (NA) and at least one synthetic binding unit (SBU), generally described by the formula $(NA)_n(SBU)_m$, wherein $n \geq 1$, and $m \geq 1$. Thus, the conjugates of the invention, and for use in the methods of the invention, may vary by the number and arrangement of nucleic acid and synthetic binding unit components, by the choice of their nucleic acid components, and by their choice of their synthetic binding unit components. Thus it is possible, for example, to link nucleic acids, oligonucleotides or polynucleotides, other supramolecular complexes or polymers to one or more pRNA, pDNA and/or CNA components so that the molecules form a stable unit, a conjugate, under the conditions required for their use. In this connection, the conjugation need not necessarily be covalent but may also be carried out via supramolecular forces such as van der Waals interactions, dipole interactions, in particular hydrogen bonds, complex-type bonds or ionic interactions.

The term "nucleic acids", as used herein, includes nucleic acids, oligonucleotides and polynucleotides and other molecules which are capable of specifically hybridizing to their complement (or partial complement), and which are composed of natural or modified nucleotides. Molecules regarded as nucleic acids, oligonucleotides or polynucleotides are all oligomers and polymers which occur naturally or else can be prepared synthetically and which have the ability to hybridize with oligomers of naturally occurring nucleic acids. It should be noted that, as used herein, "nucleic acids" may be differentiable by sequence of bases, by chemical composition (e.g., DNA vs RNA), or simply by natural or arbitrarily designated origin (e.g., an amplified sequence from two samples.) For example, $NA_1$ and $NA_2$ may be distinct because they are two aliquots which have been separately dispensed from the same PCR amplification of the same gene from the same sample cells. Usually, however, nucleic acids will be considered distinct based on sequence or origin from a separate sample.

Nucleic acids have a somewhat chemically repetitive structure made up from monomeric recognition nitrogen heterocyclic base units linked through a backbone, usually furanosyl sugar with phosphodiester bridges in naturally occurring nucleic acids. Nucleic acids, oligonucleotides and polynucleotides normally have a linear polymeric structure, but branched nucleic acid structures have been devised using chemical modifications and various branching moieties during chemical synthesis. Examples of naturally occurring nucleic acids are DNA and RNA, in which the nucleoside monomers comprising 2-deoxy-D-ribose and D-ribose, respectively. In DNA and RNA, the sugars are both in furanose form, are via phosphodiester bonds to form the backbone of the polymer. The N-glycosidically linked nitrogen heterocyclic bases form the specific recognition structure which allows DNA and RNA to specifically pair based on the sequence of the bases.

Examples of non-natural oligonucleotides and polynucleotides are the chemically modified derivatives of DNA, and RNA such as, for example their phosphorothioates, phosphorodithioates, methylphosphonates, 2'-O-methyl RNA, 2'-fluoro RNA. In addition, more structurally different molecules which can pair with DNA and RNA are also included within the definition of nucleic acids, like locked nucleic acids (LNA) or peptide nucleic acids (PNA) (Sanghivi, Y. S., Cook, D. P., Carbohydrate Modification in Antisense Research, American Chemical Society, Washington 1994; Uhlmann; Peyman; Chemical Abstracts 90(4), 543–584 (1990)). A key characteristic of all nucleic acids, oligonucleotides and polynucleotides, as defined herein, is their ability to pair with or bind to the naturally occurring nucleic acids.

A special category of nucleic acids, as defined herein, are aptamers or aptazymes. These molecules, which are composed of nucleotides, which are functionally (if not structurally) distinguishable by their specific affinity, or binding to target molecules. The molecular recognition of aptamers and aptazymes is based on binding which is mediated via the spatial structure and dynamics and the spatial presentation of parts of the molecule, similar to the antibody-antigen recognition principle. The polar nitrogen base moieties of the nucleic acid aptamers, arranged by the sequence of the nucleotides, are thus able to form a spatially arranged "hand" to grab the target molecule. In addition to their specific recognition properties, aptazymes possess a catalytic function. For example by brings a pair of reactant target molecules into proximity in the proper spatial relationship, the aptazyme can produce a favorable thermodynamic environment to promote the reaction.

Nucleic acids in accordance with this definition also include those molecules which contain in addition to the nucleic acid sequence required for pairing or molecular recognition of potential target molecules further parts which serve other purposes such as, for example, detection, conjugation with other molecular units, spacing or branching. The molecules include in particular the covalent or stable noncovalent conjugates of nucleic acids, oligonucleotides and polynucleotides with fluorescent dyes, peptides, proteins, antibodies, aptamers, organic and inorganic molecules.

Figure 5:
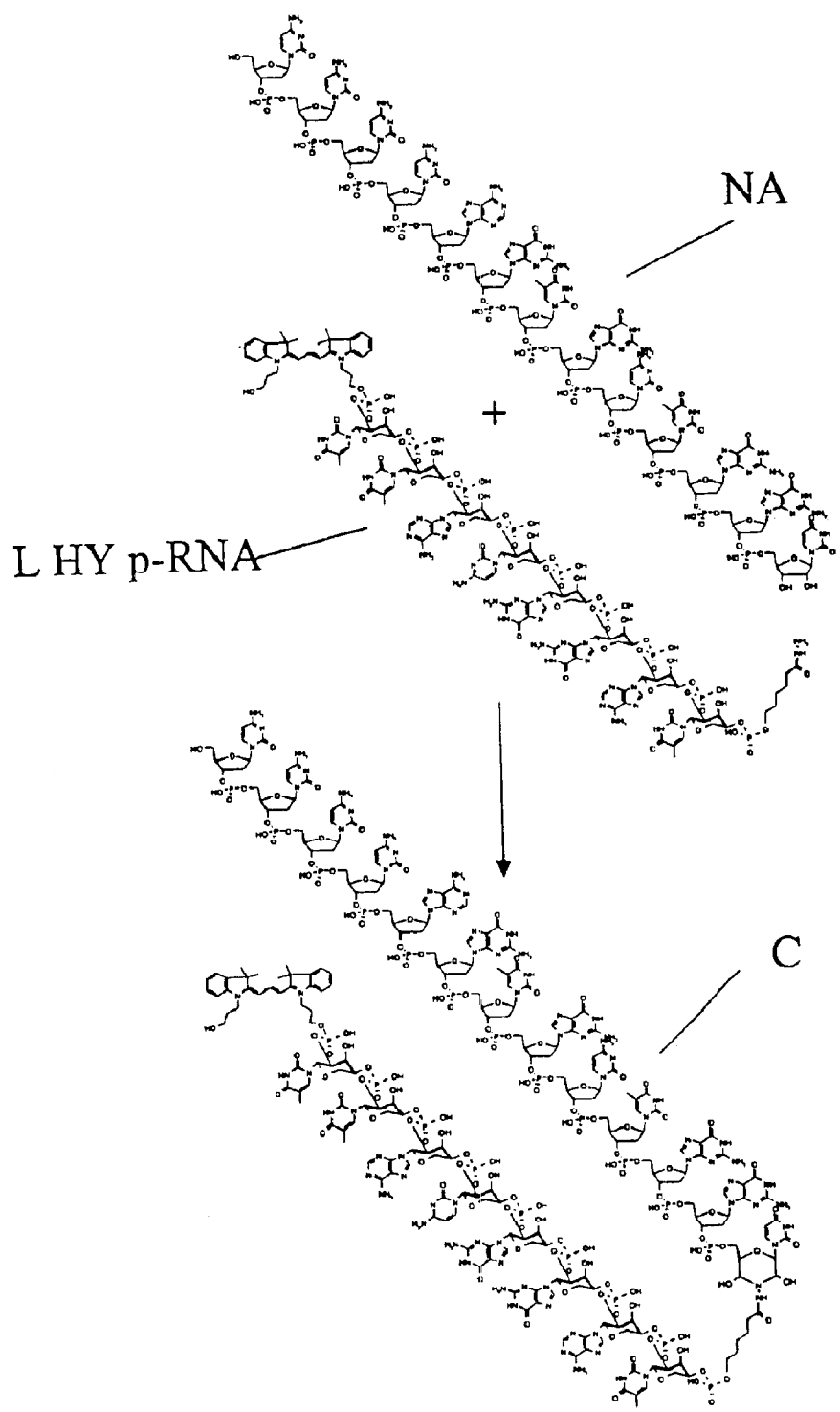
FIG. 5: An illustration of the conjugation of a DNA having a 3' terminal ribonucleotide (NA) with a vicinal diol, and a 2' Cy3-labeled and 4' monohydrazide-modified pRNA (L HY pRNA) to give a conjugate (C) as described in Example 1.4.
Figure 20B:
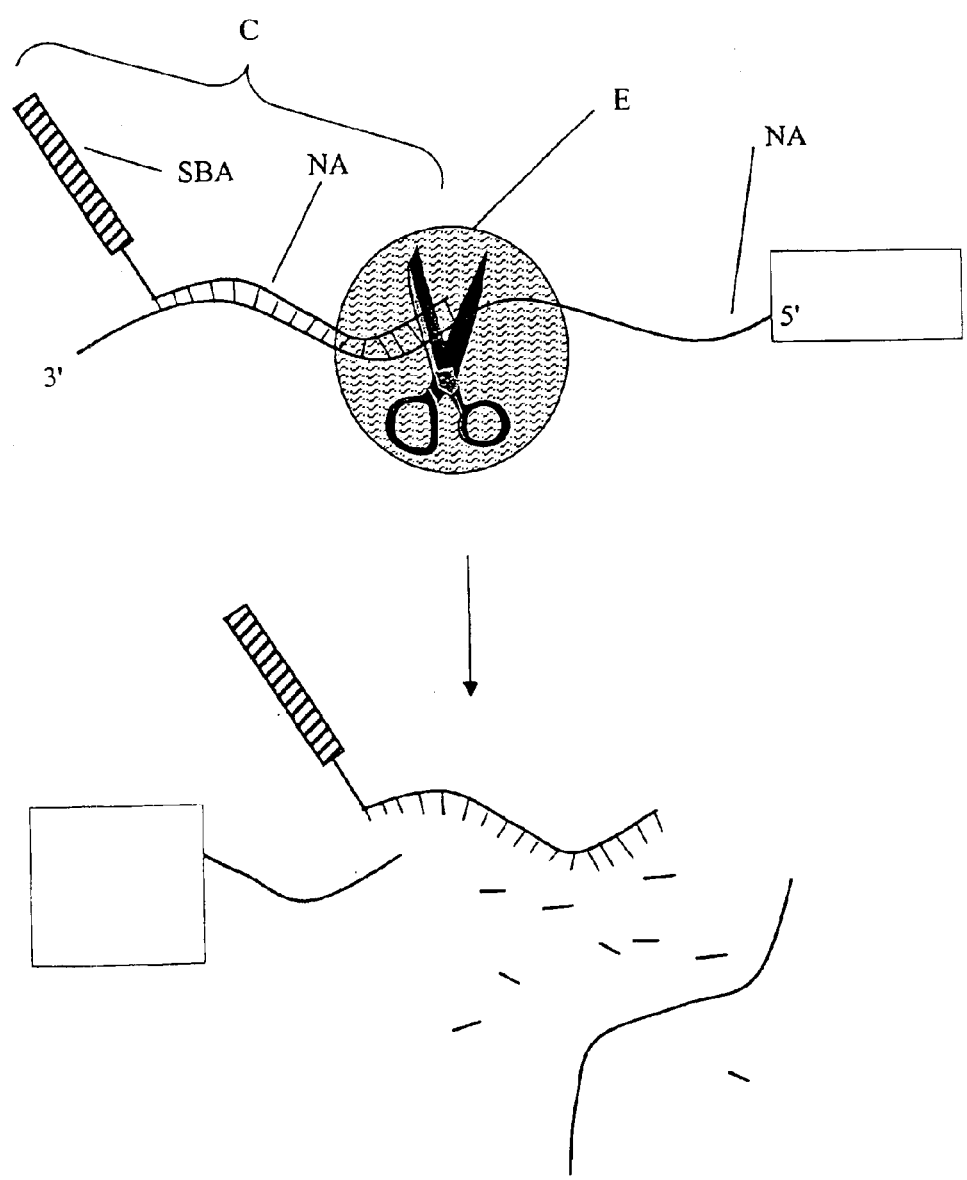

In particular, one may desire to label the nucleic acid, or the SBU, of a conjugate with a detectable labeling moiety. Often, the labeling moiety is attached to the conjugate at the end of the NA or SBU which is opposite the site of conjugation, as illustrated in FIG. 5. Labels are useful for several purposes in the systems of the invention, including ensuring that a nucleic acid has been immobilized at a particular location by the SBS, and quantifying an enzymatically modified conjugate that has, e.g., incorporated a labeled base, or had a quencher cleaved off, as in FIG. 20. Preferred labeling moieties for use in the present invention include fluorescent moieties, quencher moieties, visible dye moieties, radioactive moieties, chemiluminescent moieties, biotin moieties, hapten moieties, micro-particle (e.g., visible colloidal gold microspheres, fluorescent microspheres, etc.) moieties, (para)magnetic micro-particles, and enzymatic labeling moieties. In particular, fluorescent moieties are preferred because of their easy handling and safety. Suitable fluorescent moieties for use in the present invention include BODIPY™ dyes, cyanine dyes, Alexa™ dyes, fluorescein dyes, rhodamine dyes, phycoerythrin dyes, coumarin dyes, Texas Red dyes, Lissamine™, FAM, HEX, TET, TAMRA, ROX, EDANA, 4-Acetamido-4'-isothiocyanato-stilbene-2, 2'-disulfonic acid, 4,4'-& Diisothiocyanatostilbene-2,2'-disulfonic acid, Succinimidyl pyrene butyrate, Acridine isothiocyanate, Cascade Blue, Oregon Green, Lucifer Yellow vinyl sulfone, and IR1446 (Kodak™ Laser Dye). In addition to fluorescent moieties, one may wish to use a quencher moiety to absorb particular wavelength of light. Suitable quencher moieties for use in the present invention include Black Hole Quencher™ moieties, DABCYL, Reactive Red 4 (Cibacron Brilliant Red 3B-A), Malachite Green, 4-Dimethylaminophenylazophenyl-4'-isothiocyanate (DABITC), and 4,4'-Diisothiocyanaitodihydro-stilbene-2,2'-disulfonic acid moieites.

The partners of a binding system binding specifically to one another are denoted by binding unit and address unit. The part of the binding system which is fixed to the support materials is referred to as synthetic address unit (SAU), while the nucleic acid-conjugated part contains the complementary synthetic binding unit (SBU). Thus, the nucleic acids in the conjugates used in the present invention are linked to synthetic binding units which are able to specifically recognize a complementary synthetic address unit fixed to a support material. Synthetic binding units (SBUs) and synthetic address units (SAUs) useful in this invention are molecular units which are capable of a specific molecular pairing. When the SBU and SAU recognize and pair, the two form a stable and specific supramolecular complex, or a synthetic binding system (SBS.) Although the SBU/SAUs which may be used in the invention are not limited to a particular molecular species (e.g., pRNA, pDNA, or CNA), they may be described in terms of their key functions and characteristics.

A characteristic of the binding systems is that binding of the components of the binding system is normally reversible and that the position of the equilibrium between free and complexed components of the binding system is may be influenced by temperature, pH, concentration and other solution conditions, in order to promote the binding event, or to strip off the associated SBUs from their corresponding SAUs. Another primary characteristics of synthetic binding systems in accordance with this invention are that they are of non-natural origin, and do not mimic the spatial relationship of nucleic-acid-hybridizing structures. Thus, the SBU/SAUs used in the present invention have been prepared synthetically, and have the advantage of not interacting with natural nucleic acids. Another advantage is the ability to form more stable complexes than nucleic acids of natural origin, in particular with respect to enzymatic degradation processes. Since synthetic binding systems do not pair with, or hybridize or bind to nucleic acids, oligonucleotides or polynucleotides, the use of such systems for sorting and immobilizing nucleic acids does not lead to unwanted interaction or interference by the immobilization component with the nucleic acids (NA), other biomolecules or other components of the sample.

Preferred synthetic binding systems are nonhelical pairing systems which have an elongate linear polymer structure. In general, such structures are polymers with monomers with the general formula:

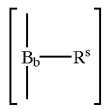

wherein $B_b$ is a backbone moiety which connects the monomeric unit to the oligomer, and wherein $R^s$ is a specific recognition moiety which provides the molecular interaction which allows the SBU to specifically interact with the corresponding synthetic addressing unit. The specific molecular interaction provided by $R^s$ may be through any non-covalent interaction, such as hydrogen bonding, Van der Walls forces, ionic interactions, etc. Such polymeric structures have the benefit of incorporating an informatic component into the SBS, in that many different combinations of a few basic monomer units may be created which specifically pair with each other. For instance, if the basic nucleotide bases (A, C, T, G) are used as the $R^s$ moieties, $4^4=256$ combinations of a four monomer sequence may be made. Although nitrogen containing heterocycles which specifically interact through hydrogen bonding are preferred $R^s$'s for use in the invention, other specific recognition moieties could be devised by one of skill in the art. In general, preferred nitrogen containing heterocycles are the naturally occurring purine and pyrimidine bases, as they may be readily obtained in quantity from natural nucleic acid sources. However, the use of synthetic or modified nitrogen heterocycles, such as tryptamine, is not uncommon in SBUs or SAUs, and is also contemplated in the invention.

In general, backbone components for use as Bb may be any readily linked monomeric component which is capable of holding the $R^s$ in position for interaction with its complement, but which also ensures that the spatial relationship of the $R^s$ moieties does not allow them to interact with naturally occurring nucleic acids. Applicants have found that six-membered ring structures, preferably those containing carbon, and optionally containing heteroatoms such as O, N, or S, are effective for this purpose. In particular, pyranosyl sugar ring structures have been useful, as they allow chemical reactions and processing which are largely analogous to traditional nucleic acid chemistries. However, cyclohexyl rings have also been employed as backbone moieties. Also, other types of molecules, such as crown ethers, azo-crown ethers, polycyclic carbon structures, or other molecular structures could be used.

Particularly preferred monomeric units which can be utilized for the synthesis of synthetic binding systems in accordance with this invention are, for example, pRNAs, pDNAs or CNAs. Such building blocks are described, for example, in WO 98/25943, Helv. Chim. Acta 1993, 76, 2161–2183, Helv. Chim. Acta 1995, 78, 1621–1635, Helv. Chim. Acta 1996, 79, 2316–2345, Helv. Chim. Acta, 1997, 80, 1901–1951, WO 99/15539 ("pRNA"), WO 99/15509 (cyclohexyl nucleic acid or "CNA") and by Beier, M.; et al.; Science 283, 699–703 (1999). The useful characteristics of these molecules are also generally applicable to largely analogous structures having, e.g., a different linkage moiety besides phosphate between the sugar residues of the backbone, or other minor alterations. It is interesting to note that SBUs and SAUs using these types of monomeric units may be made up of different classes of monomers, so long as the specific recognition is maintained. Heterologous binding systems which are preferred here are pRNA/pDNA, pRNA/CNA or pDNA/CNA. However, it is still more preferred that the SBU and SAU utilize the same class of monomers.

pRNA, pDNA or CNA form synthetic binding systems (SBS) which pair in a selective and stable way. The stability of pair formation depends on the number, composition and sequence of monomeric building blocks in the oligomeric binding system and on the number of base stacking interactions between the strands (inter-strand base stacking). Unlike naturally occurring nucleic acids, the strength of the SBS interaction for pRNA, pDNA, and CNA is initially stronger than for a nucleic acid utilizing the same sequence, and the strength of the interaction increases over a larger dynamic range the length of the paring sequence increases. Thus, SBSs may be easily devised with pRNA, pDNA, and CNA which have an increased binding strength greater than that of natural nucleic acids, and that will remain bound under conditions which are stringent for the nucleic acid sequence portions of the conjugates. The SBU region or the SAU region producing a specific recognition preferably comprises from 3 to 15, more preferably from 6 to 10, monomers. Specifically useful sequences for use in libraries or sets of conjugates are described below.

The synthetic binding systems (SBS) or components thereof (SBU and SAU) on their own cannot be synthesized, amplified, modified, processed, ligated, fragmented or hydrolyzed by enzymes which are known from nucleic acid technology, such as polymerases, ligases, nucleases, restriction enzymes, etc., for example. This property is particularly advantageous when using conjugates of synthetic binding units and nucleic acids, since the part of the associate, which relates to the synthetic binding system, is not modified, blocked, removed or processed by the enzymatic steps normally necessary for processing the sample or the nucleic acid, such as a preceding amplification, for example. The property is also advantageous, because the synthetic binding system (SBS) or its components (SAU/SBU) are not subject to degradation by enzymes which may be contained in the sample.

As mentioned above, the synthetic binding systems (SBS) and/or the synthetic binding units (SBU) and/or the synthetic address units (SAU) may contain additional molecular groups which are used for detection, conjugation with other molecular units, spacing or branching. The molecular groups include in particular the covalent or stable noncovalent conjugates of pRNA, pDNA or CNA with labeling moieties as described above.

Specific examples of such conjugates utilizing pRNA, pDNA, and CNA for the SBU component have been described previously in WO99/15893 (U.S. Ser. No. 09/509,051, filed Mar. 20, 2000), WO99/15542 (U.S. Ser. No. 09/509,011, filed march 20, 2000), WO99/15541 (U.S. Ser. No. 09/509,039, filed: Mar. 20, 2000), and WO99/15509 (U.S. Ser. No. 09/509,040, filed: Mar. 20, 2000), incorporated herein by reference in their entirety. In addition to the newly developed conjugates described herein, these are also useful in the novel array construction methods, supermolecular structures, biological assays, and enzyme modification methods of the invention.

Particular Conjugates Structures for Use and Their Production

Where both n and m are 1, the conjugate comprises a single SBU conjugated to a single NA. These are the most basic types of conjugates for use in the invention. These conjugates have the general formula:

(NA)—X—(SBU)

in which (NA) is a nucleic acid, preferably a DNA, RNA, modified DNA, or modified RNA, as further described below. The nucleic acid is preferably linked covalently to X via the 3' or 5' oxygen of one of the terminal nucleotides. See FIG. 1

(SBU) is a synthetic binding unit as described above, preferably a pRNA, pDNA or CNA or a modified form thereof. Preferably, and the synthetic binding unit is linked to X preferably via a 2' or 4' carbon (or the equivalent carbon of the cyclohexyl CAN moiety) of one of the terminal monomers. However, linkage through a nitrogen heterocyle moietiy, such as through a tryptamine linker, is also within the present invention. See FIG. 1.

X is a linking group suitable for conjugating the nucleic acid with the synthetic binding unit. Although several such groups could be devised by one of ordinary skill in the art; preference is given to linker groups having the one of the following structures (oriented in either direction):

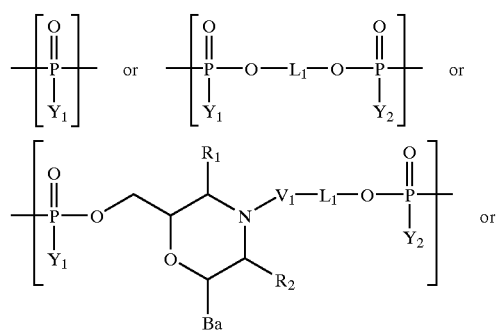

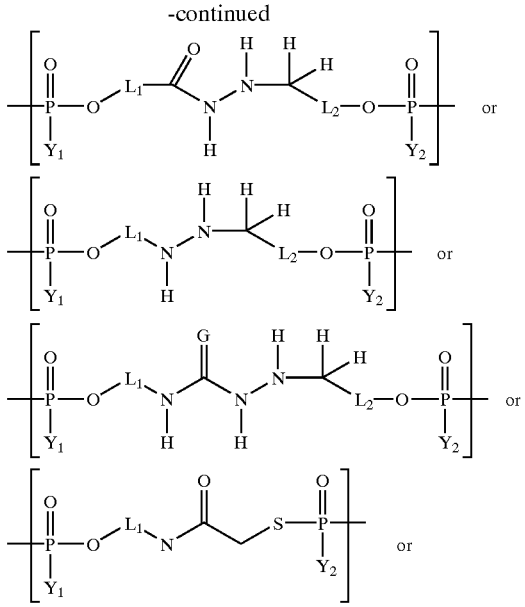

and where $Y_1, Y_2$ are independently of one another OH; SH, $NH_2$ or $CH_3$ and where G is O or S and where $L_1, L_2$ are, independently of one another, linkers selected from the group consisting of:

a covalent bond; and a linker chain moiety comprising a saturated or unsaturated, branched or unbranched, substituted or unsubstituted, chain of 1–60 carbon atoms and 0–40 heteroatoms selected from the group consisting of N, O, and S. Exemplary non-covalent bond linkers preferred linkers include —[—$(CH_2)_n$—]— or —[—$CH_2$—$CH_2$—(O—$CH_2$—$CH_2)_m$]— or —[—$CH_2$—$CH_2$—$CH_2$—(O—$CH_2CH_2$—$CH_2)_q$]— or —[$(CH_2)_v$—C(O)NH—$(CH_2)_z$—]— or —[$CH_2)_v$—NHC(O)—$(CH_2)_z$—]— with n, m, q, v, z in each case independently of one another being an integer between 1 and 20, and more preferably, n is between 2 and 12, m is between 1 and 5, q is between 1 and 4, and v and z are independently between 2 and 6; and where $V_1, V_2$ are independently of one another a group selected from

—[—$CH_2$—]— and

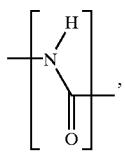

and where $R_1, R_2$ are independently of one another H or OH, and where

Ba is a nitrogen heterocycle moiety, such as, e.g., an indole linker or a base of the kind that is normally utilized in naturally occurring or man-made nucleic acids (adenosine, cytosine, guanine, thymidine, idenosine, etc.) and synthetic binding systems.

Figure 2:
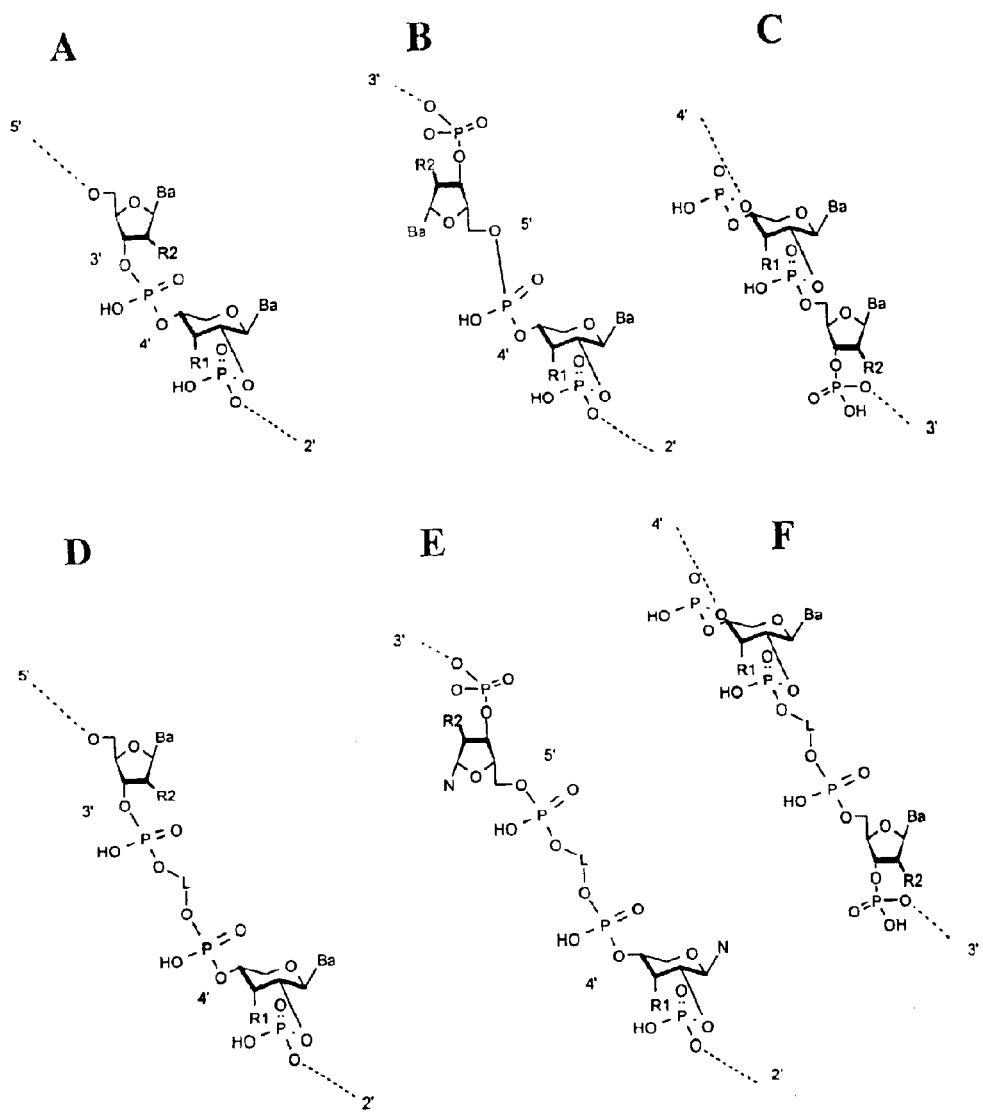
FIG. 2: An illustration of some preferred linkage arrangements and spacers for use with nucleic acids and pRNA synthetic binding units. R1=H, OH, OMe, Me; R2=H, OH, OMe; L=$(CH_2)_n$; $CH_2$—$CH_2$—(—$OCH_2$—$CH_2$—$)_n$—O—$CH_2$—$CH_2$ $CH_2$—$CH_2$—$CH_2$—(—O—$CH_2$—$CH_2$—$CH_2$—$)_q$—O —$CH_2$—$CH_2$—$CH_2$; Ba=heterocyclic base (C, T, U, G, A, etc.)A: Linkage of the 4' end of a pyranosyl building block of a SBU to the 3' end of a nucleic acid directly through a phosphate. B: Linkage of the 4' end of a pyranosyl building block of an SBU to the 5' end of a nucleic acid directly through a phosphate. C: Linkage of the 2' end of a pyranosyl building block of an SBU to the 5' end of a nucleic acid directly through a phosphate. D: Linkage of the 4' end of a pyranosyl building block of an SBU to the 3' end of a nucleic acid via a linker (L). E: Linkage of the 4' end of a pyranosyl building block of an SBU to the 5' end of a nucleic acid via a linker (L). F: Linkage of the 2' end of a pyranosyl building block of an SBU to the 5' end of a nucleic acid via a linker (L).

Conjugates using X structures:

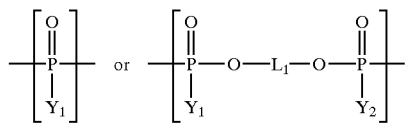

are particularly preferred for use in the invention, as pRNA and pDNA embodiments may be readily synthesized utilizing solid phase phosphoramidite synthesis methods. To make the novel L linker conjugates of the invention, a number of "spacer" phosphoramidite reagents with a wide variety of L moieties care available from commercial sources such as Glen Research (Sterling, Va.). These include polyethylene glycol chains, alkyl chains, a-basic ribose, etc. In addition, the organic chemist of ordinary skill may synthesize suitable linker phosphoramidites from suitable polyether, polyester, polyamide, or other spacer moieties. Various linkage arrangements are illustrated in FIG. 2.

An option for preparing conjugates with a free 3' end in the nucleic acid portion is to start the synthesis of the binding system on the CPG support, and then assemble the nucleic acid after the SBU. If reverse building blocks are used for this purpose, it is possible to synthesize the nucleic acid in the 5'→3' direction. The result is a linkage as depicted in FIG. 1B and FIGS. 2B/2E. As long as no free 3' end is required in the nucleic acid part, the nucleic acid synthesis may be carried out with standard building blocks on the binding unit. The result is a linkage as depicted in FIG. 1A and in FIG. 2A/D (cf.: DE19741715 or WO99/15539: "Pentopyranosylnucleosid, seine Herstellung und Verwendung").

Applicants have recently devised improved methods for the direct solid phase synthesis of pRNA, pDNA, or other phosphate-backbone conjugates. It was surprising for applicants to find that it is possible to prepare conjugates of synthetic binding systems and nucleic acids particularly easily in a chemical solid phase synthesis, if a particular protective group strategy is applied. The allyl protective group used previously, and its deprotection on the pRNA phosphoester using palladium catalysts, led to partial fragmentation of the synthesized oligomer during deprotection when relatively long strands were synthesized on the support. In contrast, using a β-cyanoethyl protective group and the standard hydrazine deprotection step leads to very low yields of the desired conjugate pRNA. The removal of the β-cyanoethyl group by hydrazine, and desired conversion into a phosphodiester which can be deprotected by the hydrazine, is slower than the undesired side reaction of nucleophilic cleavage of the phosphotriester bonds of the conjugate by hydrazine. Surprisingly, treatment of the pRNA-DNA conjugate while bound to the CPG support with a solution of an alkylamine in an inert solvent, after the completion of synthesis, avoids this problem. After treatment, the β-cyanoethyl protective group may be deprotected with hydrazine without cleaving the pRNA-DNA conjugate. Preferably, a secondary alkylamine in an inert solvent is used. Preferred secondary alkylamines include dimethylamine, diethylamine, dipropylamine, dibutylamine, dipentylamine, dihexylamine, di-N-octylamine, di-N-decylamine, didodecylamine, N-ethylmethylamine, N-methyl-N-propylamine, N-methylbutylamine, N-methylpentylamine, N-methylhexylamine, N-ethylpropylamine, N-(N-butyl)-N-propylamine, N-amyl-N-butylamine, N,N'-di-N-butyl-1.6-hexanediamine, N,N'-dimethyl-1,3-propanediamine, N,N'-dimethyl-1,6-hexanediamine. Diethylamine is particularly preferred. The alkylamine is preferably in solution at a concentration of about 0.2% to about 10%, more preferably from about 1% to about 5%, and more preferably at a concentration of about 1.5%. Suitable solvents for use include dichloromethane, chloroform, carbon tetrachloride, dichlorethane, tetrahydrofuran, toluol, diethylether, ethanol, methanol, acetonitrile, hexane, and heptane. Applicants have found an about 1.5% solution of diethylamine in dichloromethane to be particularly suitable. The intermediate obtained after treatment can readily be deprotected by hydrazine and purified chromatographically. Thus, directly synthesized pRNA-DNA conjugates may now be made easily in good yield.

It is often desirable to link pre-synthesized binding systems to finished nucleic acids. Nucleic acids which are obtained from natural sources or via enzymatic reactions such as, e.g., in vitro transcription (also frequently used for preparing aptamers and aptazymes) are more advantageously conjugates to SBSs with a functional linker. However, many biochemical conjugation methods described in the literature (e.g. Hermanson, G. T.; Bioconjugate Techniques, Academic Press, San Diego 1996) have proved chemically unsuitable for the nucleic acids and/or the synthetic binding units. Several methods for linking nucleic acids with nucleic acids utilize the hybridization of the nucleic acids in order to achieve initial attachment and positioning, followed by covalently linking the strands (e.g., photochemically via psoralen.) Such method are not useful for SBU/NA conjugation, as the SBUs do not pair with nucleic acids. Applicants disclose several novel conjugates based on hydrazine and hydrazide chemistries for linking pre-made SBUs and NAs together into conjugates. Hydrazide-modified nucleic acids or synthetic binding units have advantages compared with amino-modified nucleic acids or synthetic binding units, because they can be used over a wider pH range, and because the products formed are relatively stable, even without the reduction step required for the amino-modified nucleic acids or synthetic binding units. Hydrazine conjugation chemistries have been utilized for nucleic acids, as described in WO00/19653. However, applicants have found that hydrazine chemistries are particularly useful and effective for coupling pRNA, pDNA, and CNA SBUs to nucleic acids. For instance, conjugates with X of the formula:

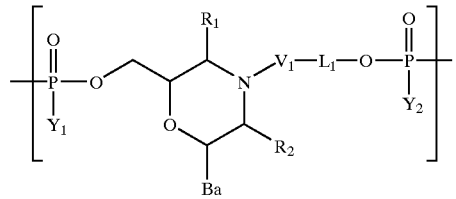

may be obtained by reacting a first conjugate moiety (the SBU or NA of the conjugate) containing a hydrazide with a second conjugate moiety containing an terminal ribonucleoside (or simply a ribose, without a base). This is illustrated in FIG. 5. An advantage of this method is that the nucleic acid to be conjugated does not have to be chemically modified: either a naturally occurring terminal riboside may be used, or one may be added to a deoxyribonucleic acid enzymatically with a terminal transferase. The ribonucleotide may be oxidized with periodate to give the corresponding aldehydes, which then react with amines or hydrazides to give stable conjugates.

In addition, applicant has developed several other novel hydrazide and hydrazine coupled conjugates for use in the invention. Those with the formula:

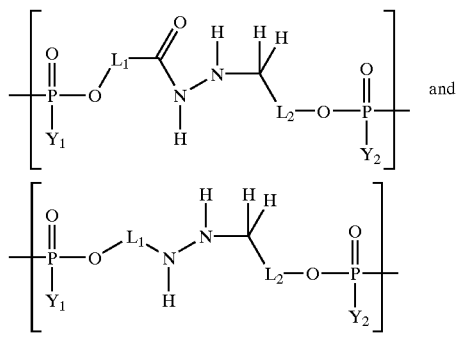 and can be produced by reacting an aldehyde first moiety with a hydrazide or hydrazine second moiety, respectively. Example 2.2 shows a method for preparing a hydrazide-modified pRNA conjugate. An aldehyde function is obtained at the 3' end of the oligonucleotide, if the nucleic acid is synthesized on a commercially available glyceryl support (e.g.: Glen Research Corp., Sterling, Va., USA; catalog No. 20-2933-41) and subsequently oxidized with sodium periodate. This variation is particularly useful conjugation with RNA, since the first RNA building block at the 3' end is no longer attacked by periodate, remaining completely intact. If it is desired to introduce the aldehyde function at the 5' end, it is possible during synthesis to link up a phosphoramidite building block which either already contains a protected aldehyde function or includes a protected diol (e.g. described in EP 0 360 940), which can be cleaved subsequently by means of periodate. The two components are reacted in phosphate buffer, pH 7.4, in the presence of sodium cyanoborohydride, and the product is isolated (e.g., by RP-HPLC).

In addition, the novel conjugates linked by an X of the formula:

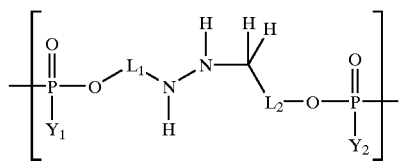

are useful in the invention. These may be obtained by a method analogous to that of the hydrazide conjugates by reacting a semicarbazone or thiosemicarbazone containing first conjugate moiety with an aldehyde containing second conjugate moiety.

An additional conjugate for use in the present invention comprises and X of the formula:

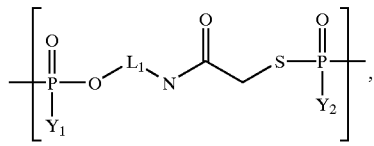

which may be obtained by treating a thiol on a first conjugate moiety with iodoacetate, and then reacting it with an amine on a second conjugate moieity. See In addition to the relatively simple conjugates described above, more complex novel conjugate structures wherein n, m, or both, are $\geq 2$ may be easily prepared using the guidance provided herein. Where $n \geq 2$, the conjugate comprises multiple nucleic acids. Likewise, when $m>1$, the conjugate comprises multiple SBUs. Using a method for preparing and purifying conjugates of synthetic binding units and nucleic acids it is possible for various conjugates to be prepared and tested for their applicability for addressing, sorting and immobilizing nucleic acids (NA) on the support material. Thus, conjugates may be designed which differ by:

a) the choice of binding unit,
b) the choice of nucleic acid,
c) the structure of the linkage between nucleic acid and binding unit,
d) the orientation of the nucleic acid,
e) the number of synthetic binding units conjugated with a nucleic acid.

Such multi-component conjugates are may be formed as linear-linked chain structures, or as branched structures utilizing a branching moiety, as described below. Multi-SBU structures have several uses, including: increasing the immobilization bond strength through the formation of multiple SBSs to immobilize one or more conjugated nucleic acids, providing multiple SBUs for use with different arrays of immobilized SAUs, and providing an extra informational dimensionality to the molecule by choosing conditions under which the SBUs bind to the SAUs to require multiple SBU/SAU binding events for immobilization (e.g., the nucleic acid is immobilized only at a location to which both $SAU_1$ and $SAU_2$ are attached, but not one to which just $SAU_1$ is attached.) This latter alternative is particularly attractive in mass-produced systems, as it allows shorter sequences of synthetic binding system components to be utilized to convey the 16 same level of specificity as longer sequences (e.g., two 6-mers rather than a single 12-mer.) In addition, by utilizing branching groups or linear structures one may conjugate multiple NAs to one or more SBUs. This allows the creation of an immobilizable probe structure with multiple functionalities (e.g., capture probes for two genetic loci, or forward and reverse SDA probes as illustrated in FIG. 25).

The SBUs and NAs of the complex conjugates may be linked together via a linker group X or branching group W, in various configurations. For instance, conjugates may be formed with any of the following structures:

(NA)—$X_1$—(SBU)—$X_2$—(NA)

(SBU)—$X_1$—(NA)—$X_2$—SBU)

(NA)—W—(—(SBU))$_u$ (SBU)—W—(NA))$_u$ ((NA)—)$_u$—W—((SBU))$_u$.

with u being an integer between 2 and 6, preferably 2 or 3, in which (NA) Is as defined above,
(SBU) Is as defined above,
W is a branching group which makes it possible to conjugate a plurality of synthetic binding systems with at least one nucleic acid. W preferably has the general formula:

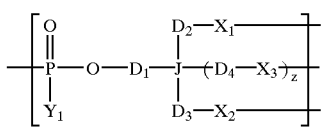

wherein $Y_1$ is OH, SH, $NH_2$ or $CH_3$;

wherein $D_1$, $D_2$, $D_3$, and $D_4$, are, independently, a covalent bond or a linker chain moiety comprising a saturated or unsaturated, branched or unbranched, substituted or unsubstituted, chain of 1 to 10 carbon atoms and 0 to 4 heteroatoms selected from the group consisting of O, S, and N;

wherein J is carbon or nitrogen;

wherein z is 0 or 1, further wherein z is 0 if J is nitrogen; and wherein $X_1$, $X_2$, and $X_3$, are independently X as described above.

Preferred branching groups include:

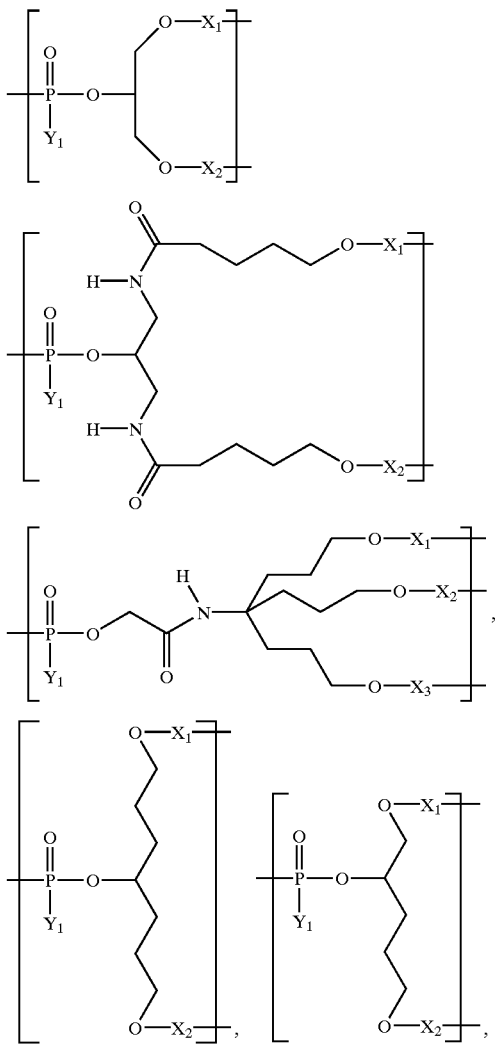

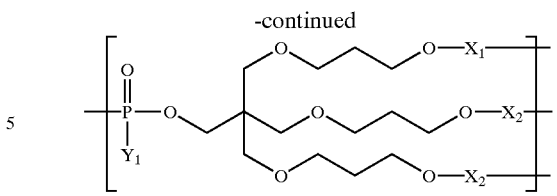

When utilizing polymeric SBUs, one of the choices in the construction of conjugates is the sequence of monomeric units in the SBU and its corresponding SAU. For use in methods of the present invention where sets of SBUs and SAUs are utilized to create arrays and other supermolecular structures, sets of suitable synthetic binding units (SBU) and complementary address units (SAU) are greatly advantageous. Using the described synthetic binding units and address units, it is possible to define a set of pairing systems which are similar in their properties but orthogonal to one another. The term "orthogonal," as used herein, means that the members of a set or group of SBUs hybridize with the other members of the set and the complementary SAU's of the other members of the set to an lesser extent than the average hybridization of all possible sequences of the same length. The concept of orthogonality is illustrated in the data in FIG. 14. As shown here, most of the sequences in this group are substantially orthogonal to each other. The 118 and 119 pairs are less orthogonal to each other than the others, though, and probably should not be utilized in the same set.

In general, set of synthetic binding units and address units preferably contains a set of different sequences of monomeric units ($R^s$s) having from 3 to 15, particularly preferably from 6 to 10 monomer building blocks. The $R^s$ sequences are preferably orthogonal within the group. Nitrogen heterocycle moieties, specifically nitrogenous base moieties, are very useful because a large number of possible combinations of subunits can be made, allowing for the production of relatively large, orthogonal groups of SBUs. The described SBUs and SAUs show mutually orthogonal behavior under high stringency conditions, and in this respect are substantially more efficient than DNA or RNA. It is, however, in addition possible to define individual subgroups of the set, which show mutually orthogonal behavior even with less stringent conditions.

In particular, the applicants have found useful sets of synthetic binding units and synthetic address unit, having the structure:

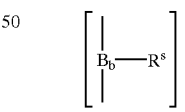

wherein $B_b$ id s backbone moiety which connects the monomeric unit to the oligomer (e.g.,) a pyransosyl or cyclohexyl ring), and wherein $R^s$ is a specific recognition moiety comprising a nitrogen heterocycle moiety, wherein the monomeric units are linearly arranged according to the formula, $$B_{s1}\text{—}(J)\text{—}B_{s2} \text{ or}$$

$$B_{s1}\text{—}(J)\text{—}B_{s2}\text{—}B_{s3}$$

wherein s1, s2, and s3 are, independently, an integer between 0 and 10, more preferably between 0 and 2, and B is any monomeric building block as is used for synthesizing the synthetic binding units (SBU), and J is a sequence of recognition moieties (R$^s$, wherein J may be the same or different than J'. In these structures, the sequences J and J' are preferably, independently, selected from group A described below, or are selected from the group B, described below, and sequences J and J' are selected from the same group.

| SEQ. ID No. | SBU/SAU Ref. No. | pRNA Sequence, 4'→2' |
|---|---|---|
| 1 | 1a | A A T G C C T A |
| 2 | 1b | T A G G C A T T |
| 3 | 3a | A A T C G C T A |
| 4 | 3b | T A G C G A T T |
| 5 | 4a | A A G T C C T A |
| 6 | 4b | T A G G A C T T |
| 7 | 6a | A A T G T C C A |
| 8 | 6b | T G G A C A T T |
| 9 | 7a | A A T C C G T A |
| 10 | 7b | T A C G G A T T |
| 11 | 10a | A A T T C G C A |
| 12 | 10b | T G C G A A T T |
| 13 | 11a | A A C G T T C A |
| 14 | 11b | T G A A C G T T |
| 15 | 12a | A G T A C T C A |
| 16 | 12b | T G A G T A C T |
| 17 | 13a | A A T C T C G A |
| 18 | 13b | T C G A G A T T |
| 19 | 14a | A A G C T C T A |
| 20 | 14b | T A G A G C T T |
| 21 | 15a | A C T A G C T A |
| 22 | 15b | T A G C T A G T |
| 23 | 16a | A A G T T C C A |
| 24 | 16b | T G G A A C T T |
| 25 | 17a | A A G C C T T A |
| 26 | 17b | T A A G G C T T |
| 27 | 18a | A T G A C C T A |
| 28 | 18b | T A G G T C A T |
| 29 | 24a | A A C G C T T A |
| 30 | 24b | T A A G C G T T |
| 31 | 25a | A C T G A C T A |
| 32 | 25b | T A G T C A G T |
| 33 | 28a | A A T T G C C A |

-continued

| SEQ. ID No. | SBU/SAU Ref. No. | pRNA Sequence, 4'→2' |
|---|---|---|
| 34 | 28b | T G G C A A T T |
| 35 | 29a | A A C C G T T A |
| 36 | 29b | T A A C G G T T |
| 37 | 30a | A G T C A C T A |
| 38 | 30b | T A G T G A C T |
| 39 | 31a | A A C T G C T A |
| 40 | 31b | T A G C A G T T |
| 41 | 34a | C T G G C A T A |
| 42 | 34b | T A T G C C A G |
| 43 | 35a | C C A G T C T A |
| 44 | 35b | T A G A C T G G |
| 45 | 36a | A A T G C G T A |
| 46 | 36b | T A C G C A T T |
| 47 | 37a | A A T C C T A G |
| 48 | 37b | C T A G G A T T |
| 49 | 102a | T C C T G C A T T C |
| 50 | 102b | G A A T G C A G G A |
| 51 | 103a | C T C T A C G T C T |
| 52 | 103b | A G A C G T A G A G |
| 53 | 104a | C C T C G T A C T T |
| 54 | 104b | A A G T A C G A G G |
| 55 | 105a | T T C T G T A T C C |
| 56 | 105b | G G A T A C A G A A |
| 57 | 106a | C T T T A T G C C T |
| 58 | 106b | A G G C A T A A A G |
| 59 | 109a | C C C A C T T G T T |
| 60 | 109b | A A C A A G T G G G |
| 61 | 110a | T C T G C T C A T C |
| 62 | 110b | G A T G A G C A G A |
| 63 | 113a | C T C A C C T A T T |
| 64 | 113b | A A T A G G T G A G |
| 65 | 117a | T T C T A T A C T C |
| 66 | 117b | G A G T A T A G A A |
| 67 | 118a | T G T T T G G G T G |
| 68 | 118b | C A C C C A A A C A |
| 69 | 119a | T G G T C G G T T G |
| 70 | 119b | C A A C C G A C C A |
| 71 | 120a | T G G T T A T C T G |

-continued

| SEQ. ID No. | SBU/SAU Ref. No. | pRNA Sequence, 4'→2' |
|---|---|---|
| 72 | 120b | C A G A T A A C C A |
| 73 | 121a | C G T G T A T G T A |
| 74 | 121b | T A C A T A C A C G |
| 75 | 122a | C T C C A T G T T C |
| 76 | 122b | G A A C A T G G A G |

Thus, substantially orthogonal groups of SBUs or SAUs may be produced by simply selecting any number (2, 5, 10 etc.) of sequences for use as SBUs or SAUs in the set from either group of sequences below:
  Group A: SEQ ID NOS. 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, and 75
  Group B: SEQ. ID Nos. 4, 6, 8, 10, 12, 14, 16, 18, 20, 22, 24, 26, 28, 30, 32, 34, 52, 54, 56, 58, 60, 62, 64, 66, 68, 70, 72, 74, and 76
More preferred subgroups of sequences from which to choose synthetic binding units for use in arrays requiring strict orthogonality for sorting are given below:
Group A' (8-mers): SEQ. ID Nos. 3, 5, 7, 9, 11, 13, 15, 17, 19, 21, 23, 25, 27, 29, 31, 33, 35, 37, 39, 41, 43, 45, and 47
Group B' (8-mers): SEQ. ID Nos. 4, 6, 8, 10, 12, 14, 16, 18, 20, 22, 24, 26, 28, 30, 32, 34, 36, 38, 40, 42, 44, 46, and 48
Group A''' (10-mers): SEQ. ID Nos. 49, 51, 53, 55, 57, 59, 61, 63, 65, 67, 69, 71, 73, and 75
Group B' (10-mers): SEQ. ID Nos. 50, 52, 54, 56, 58, 60, 62, 64, 66, 68, 70, 72, 74, and 76
Group A''' (more preferred 10-mers): SEQ. ID Nos. 49, 51, 53, 57, 59, 61, 65, 69, 71, and 75
Group B''' (more preferred 10-mers): SEQ. ID Nos. 50, 52, 54, 58, 60, 62, 66, 70, 72, and 76

For use in sets of conjugates or addresses, the sets of orthogonal sequences may be present, for example, as a pRNA, a pDNA, a mixture of pRNA and pDNA or as 1' a CNA. As interactions with native nucleic acids are not of concern when using the synthetic binding systems of the invention, the sequences for use in sets of conjugates or addressing units may be fully optimized for orthoganality, without the requirement for deleting any naturally occurring sequences. This is a considerable advantage over the use of nucleic acids as immobilization moieties in previous methods.

SAUs for use with the SBU Conjugates in the Invention

SAUs are the coordinating specific binding pairs of the SBUs of the conjugates, and so generally share similar characteristics with the SBUs. The main difference is that SAUs are attached to a support material, rather than being conjugated to a nucleic acid or other biomolecule. The SAUs may be attached to a single solid support (as in a planar rectangular array) or to several distinct supports (as in a set of beads, dipsticks, or the wells of a microtiter plate). Preference is given for utilizing sets of binding addresses which do not cross-react under the particular application conditions (e.g., physically separated in a planar array, vs. able to interact with each other on a set of beads) and which react in a similar way to stringency conditions such as, for example, pH, ionic strength, temperature, electrical potential, denaturing agents, etc., and which show similar stability properties. Thus, the SAUs preferably belong to one molecular class (e.g., all pRNA, all CNA, etc.). For specific embodiments, however, it is also possible to combine SAUs with different properties on the same support.

Any suitable support material may be used as the surface to which the SAU is attached. For instance, solid materials insoluble under the application conditions may be used. These include silicon, silicon dioxide, silicon nitride, controlled porosity glass, ceramics, metals, preferably precious metals, in particular gold or platinum, or semiconductors, metal silicilide, plastics and polymers, including conductive polymers. In addition porous materials such as, inorganic sol-gels, and hydrogels or biopolymers may be used as support materials. These include, for example, cellulose, agarose polyacrylamide, polymethacrylamide, and organic polymer hydrogels. The surfaces of the support materials can be a single material, or several materials in layers or coatings. The coatings may be in the form of monomolecular layers, of a coating containing a plurality of stacked layers, or of a coating containing disordered layers. The structure of the support layer will depend on its purpose: for instance, an agarose bead or silicon wafer surface may simply serve as a solid support to localize the SAU in a particular known position. Sensor arrays, such as the SPR devices utilized in the experiments, the support may comprise a derivatized metal surface for the direct attachment of the SAU to the sensor. Conversely, active electronic arrays, as utilize in the active supramolecular array construction below, comprise an electrode at the array locations below a permeation layer (e.g., agarose or polyacrylamide hydrogel).

As the SBSs of the invention may be utilized particularly advantageously with active electronic arrays (as the devices are described in the above referenced patents, incorporated herein by reference), this particular embodiment will be described in more detail. A particular characteristic of permeation layers utilized in active electronic arrays is that they are porous, allowing penetration of conjugates, nucleic acids or samples deep into the layer, and providing a large surface area for interactions to occur. These permeation layers also separate the nucleic acids at the activated locations from the harsh electrochemical environment immediately at the electrode. Furthermore, the surfaces of support materials or of polymers applied to support materials frequently have functional groups which allow the covalent or stable non-covalent attachment or linkage of address units of the binding systems. Examples of such functional groups are activated esters, aldehydes, thiols, amines, as well as streptavidin, avidin, and other biotin-binding proteins. etc.

In addition to the active electronic arrays (as described in the above referenced patents, and also in U.S. Pat. No. 5,605,662, incorporated fully herein by reference), typical support materials also include other devices, such as sensor chips, chips with flow-through systems or channels, fluidic systems, beads, magnetic beads, microtiter plates, stationary chromatographic phases and also other solid materials which can be used in heterogeneous assay systems.

Passive and Active Methods of Producing Supramolecular Array Structures

As described above, conjugate formation makes it possible to encode the individual nucleic acids (NAs) with one or more synthetic binding units. Encoding is defined herein as the unambiguous assignment of a specifically addressable synthetic binding unit to a nucleic acid so that subsequently the nucleic acid is specifically, able to be spatially located, immobilized, sorted, and thus detected on a support material via the specific interaction between address unit and complementary binding unit. Thus, sets or libraries of conjugates can be prepared in which various NAs are encoded by one or a group of SBUs. For example, one can produce a library in which all NAs are encoded by a different SBU, or where all NAs are encoded by a known group of SBUs. Conversely, one can produce libraries in which all SBUs encode a single NA, or a known group of NAs. If one produces a library in which all NAs are encoded by a single unique SBU, a strict 1:1 conjugate library results.

Figure 7:
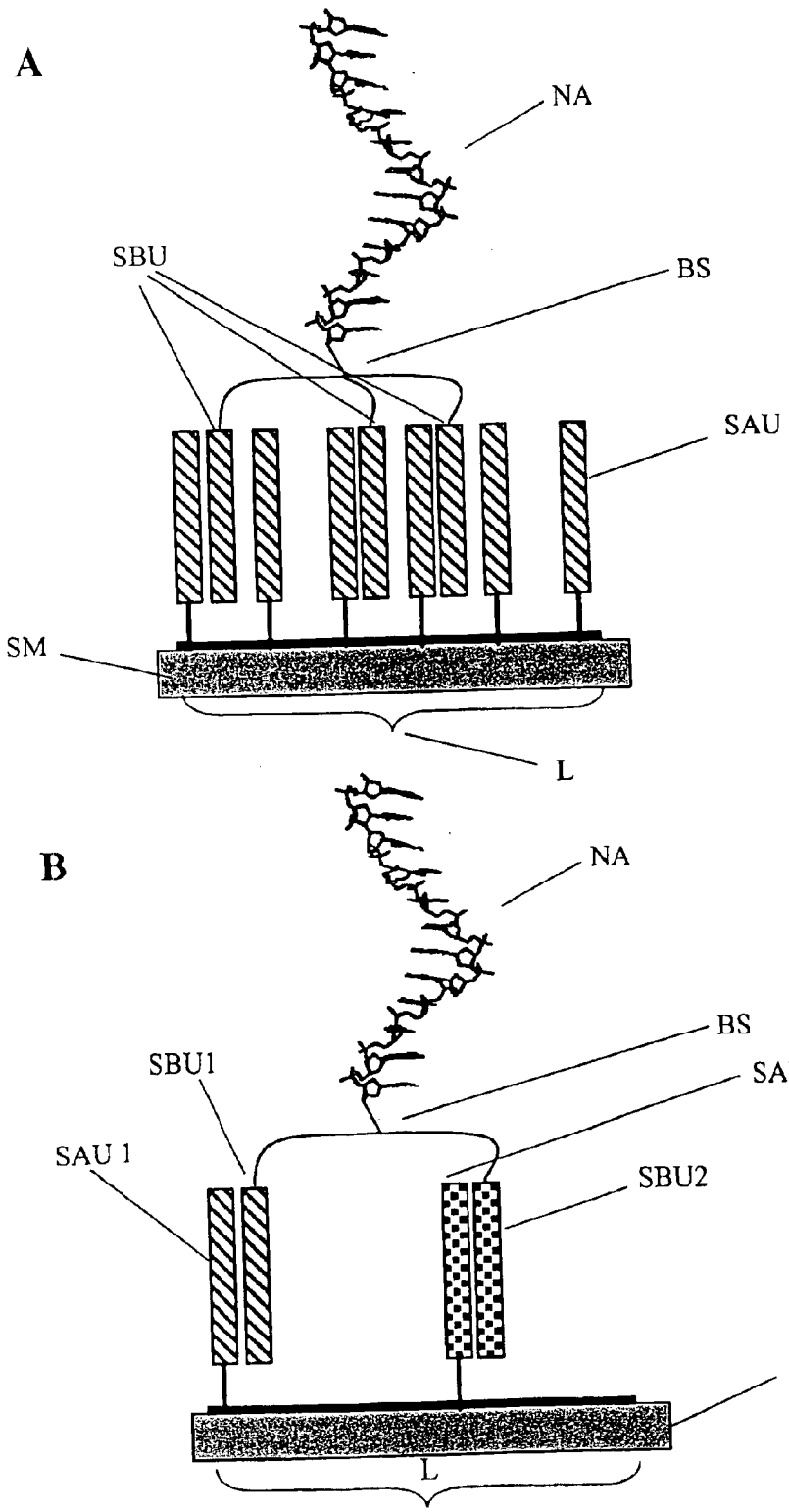
FIG. 7.
Figure 10:
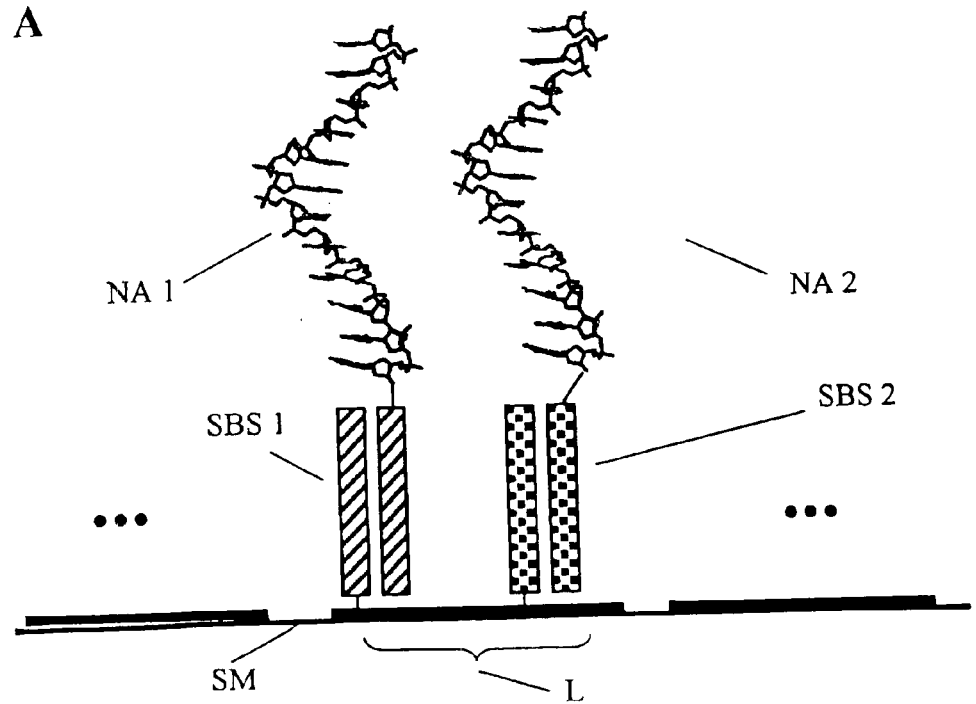
FIG. 10: An illustration of an additional embodiment in which a plurality of different molecular species or nucleic acids (NA1 and NA2) are immobilized next to one another on the same array position, or capture site. This can be achieved, as depicted in 10A, by fixing two different SAU's to one site to form two different binding systems (SBS) at one array location (L). Or, as depicted in B, the same effect may be achieved by using the same binding system (SBS), and using conjugates of different nucleic acids (NA 1 and NA 2) with the same SBU.
Figure 10:
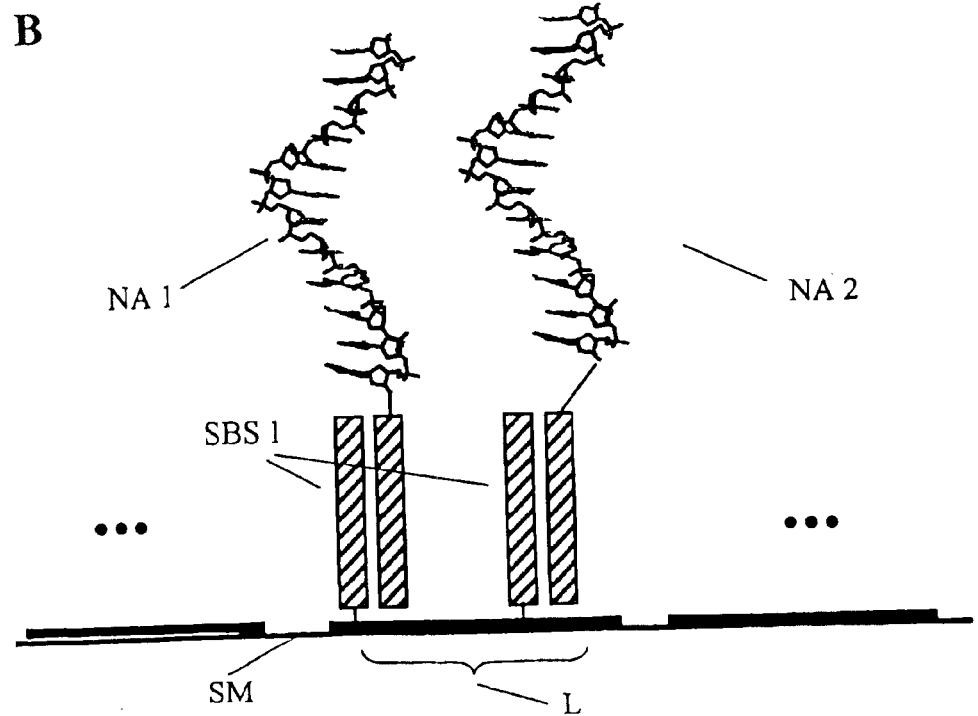
Figure 11:
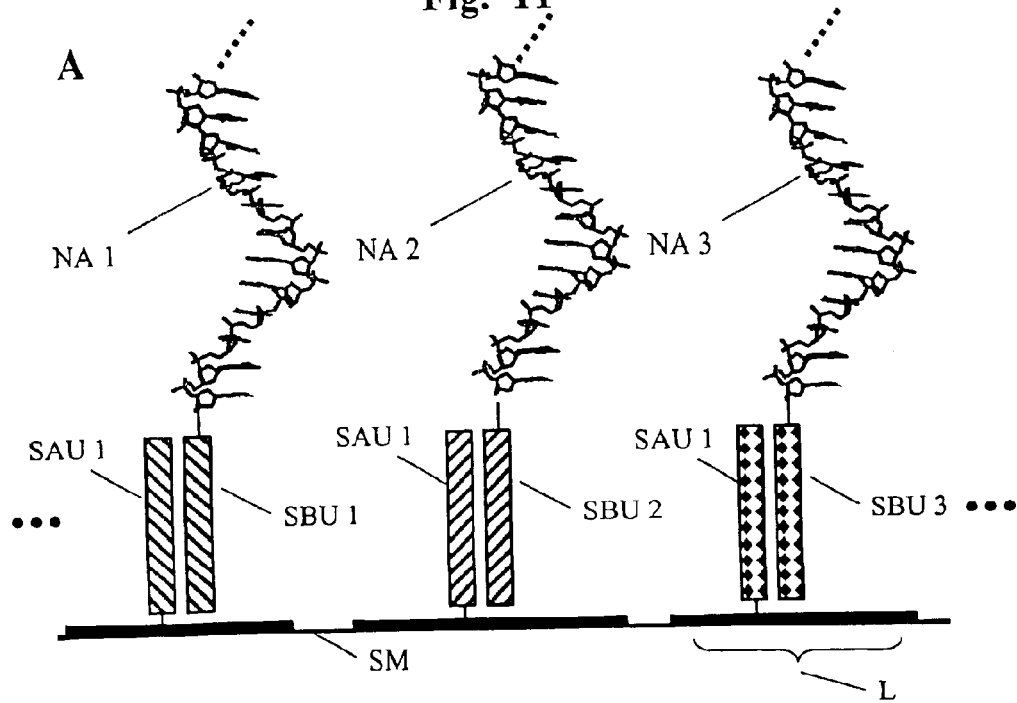
FIG. 11: An illustration of the use of synthetic binding addresses and conjugates of synthetic binding units with nucleic acids for the construction of arrays on support materials (SM). Figure A shows an embodiment in which different nucleic acids (NA 1, NA 2, NA 3, . . . ) are immobilized on different locations (L) of the support material using different binding units (SBU 1, SBU 2, SBU 3, . . . ) and different address units (SAU 1, SAU 2, SAU 3. . . ). The SAUs of the locations are, for example, simply spotted on passive arrays, or may be electronically addressed to capture sites above electrodes in the case of active electronic arrays. A characteristic of the embodiment is that each array location carries a distinctive binding address. Although this is illustrated here as a separate SAU for each SP, the distinctive addresses may as easily be formed by mixtures of SAU's (e.g., SAU 1 &2 at L 1, SAU 3&4 at L 2, etc.).
Figure 11:
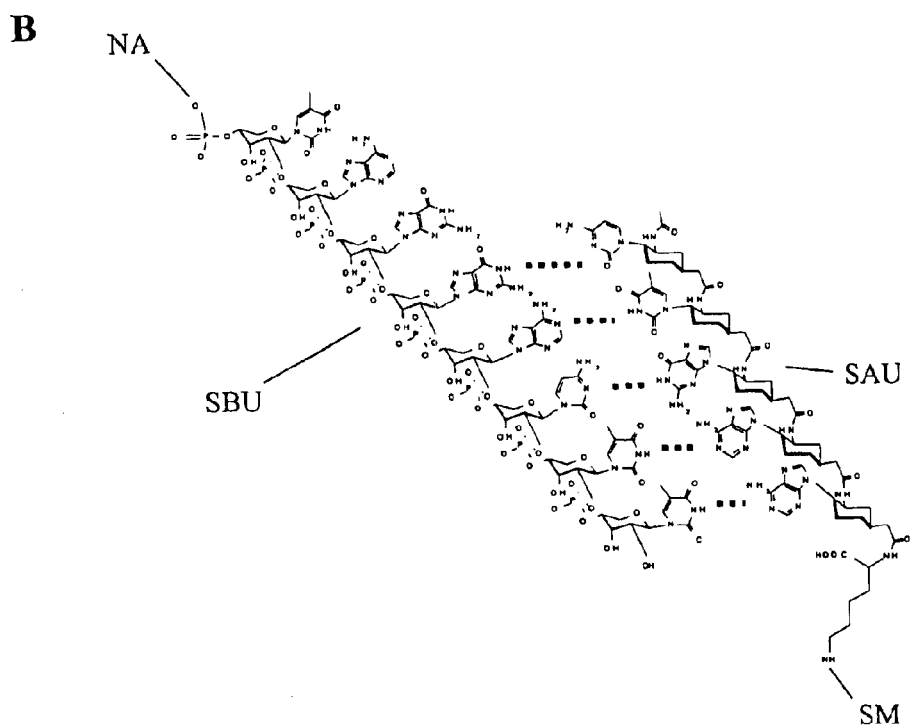

When contacted with the coordinating SAU under the appropriate conditions for binding, the SBU of a conjugate binds with the SAU to form an SBS-immobilized nucleic acid. The specific binding of the synthetic binding unit (SBU) to the synthetic address unit (SAU) preferably forms position-resolved synthetic binding systems (SBS) and constructs, and this leads to the sorting and/or immobilization of the conjugates onto the surface of the support at particular locations where the SAUs are attached. Thus, K is advantageous to attach SAUs, or defined groups of SAUs, to predetermined locations on the support, so that the identity of the immobilized nucleic acids may be determined in a position-dependent manner. For instance, the SAUs may be attached in an array of locations (rectangular, circular, or any other suitable pattern), in order to produce an array of immobilized nucleic acids at the predetermined locations. An array of this kind is prepared analogously to the methods used in DNA chip technology (cf.: Microarray Biochip technology; Schena, M. Eaton Publishing, Natick, 2000; DNA Microarrays, Schena, M., in Practical Approach Series, Oxford University Press, Oxford 1999). The attachment of the synthetic address units on the support material via a covalent linkage is particularly advantageous, although biotin/streptavidin type systems have also been used with good results. Branched systems in which one SAU is provided with a plurality of hydrazides as reactive groups have proved useful, in particular with active ester permeation layers on active electronic arrays. The provision of a multiplicity of reactive groups in a molecule leads to a faster and more stable immobilization on the support material (PCT/US00/22205). (See FIG. 4B) If a location comprises a mixture of SAUs, then several nucleic acids with different SBUs may be immobilized at a the location (see FIG. 10), or nucleic acids conjugates to multiple different SBUs may be immobilized at the location (see FIG. 7).

Thus, in one group of embodiments of the present invention conjugates in which a nucleic acid is conjugated with a plurality of synthetic binding units (either the same, or different) are used. Systems of this kind are possible by using branching building blocks (Shchepinov, M. S.; Udalova, I. A.; Bridgman, A. J.; Southern, E. M; Nucleic Acids Res.; 25, 4447–4454 (1997)) in combination with the above-described methods. See FIG. 7. The advantage of such a molecular architecture is that, due to the multiple binding systems in one conjugate, the interaction of the mobile binding system with the part of the binding system, which is immobilized on the support material, becomes multiple and cooperative. As a result, it is possible to achieve an extremely stable immobilization of the conjugates on the support material for specific applications, while maintaining the selectivity of the binding system. As discussed earlier, these systems also allow the use of shorter SBUs to produce a greater variety of specific binding pairs than is possible using a single SBU of the same length. Systems of this kind are novel and the applicants were able to obtain them for the first time.

Figure 1:
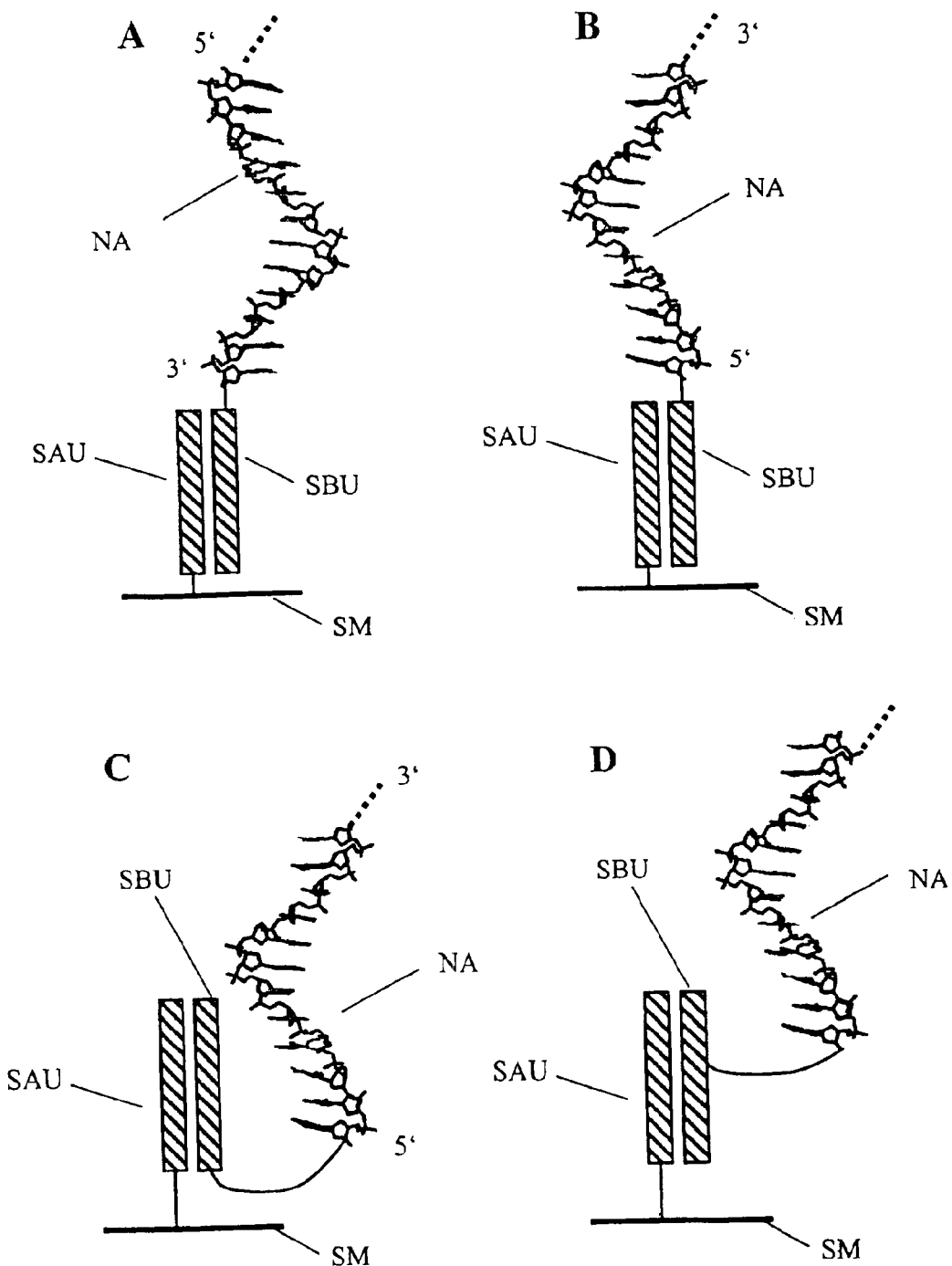
FIG. 1: A diagrammatic representation of some preferred arrangements for linking nucleic acids (NA) to synthetic binding units (SBU,) and how such conjugates can be used for immobilization on support materials (SM) using synthetic addressing units (SAU.)

FIG. 1 depicts some of the possible orientations of conjugates bound to SAUs on the surface of support materials. Depending on application, particular embodiments are preferred. For enzymatic processing of a nucleic acid part of a conjugate as a primer for a polymerase reaction, the 3' end of the nucleic acid is preferably free. This can be achieved, for example, by initiating the chemical synthesis on a CPG support with the nucleic acid part and then synthesizing the binding unit onto the nucleic acid (FIG. 1C; FIG. 2C) (see: DE19741715 or WO99/15539: "Pentopyranosylnucleosid, seine Herstellung und Verwendung" ["Pentopyranosyl nucleoside, and the preparation and use thereof"]). It is possible here, where appropriate, as depicted in FIG. 2F to insert segments as linker or spacer by modifying the nucleic acid or using commercially available modified building blocks, as described above. Such a separation of binding unit and nucleic acid is useful whenever, under the application conditions, the spatial proximity of the systems leads to steric problems, for example to poorer hybridization of the nucleic acid with the sample. Such conjugates may be obtained particularly effectively by using the novel deprotection method.

Figure 3:
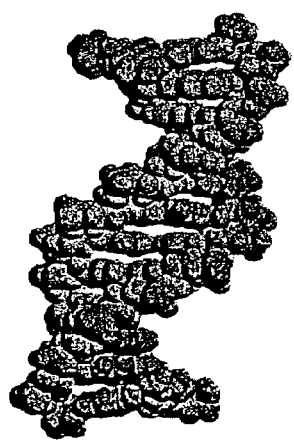
FIG. 3: A diagrammatic representation of the three dimensional structural difference between nucleic acids and the preferred synthetic binding systems for use in the invention.
Figure 3:
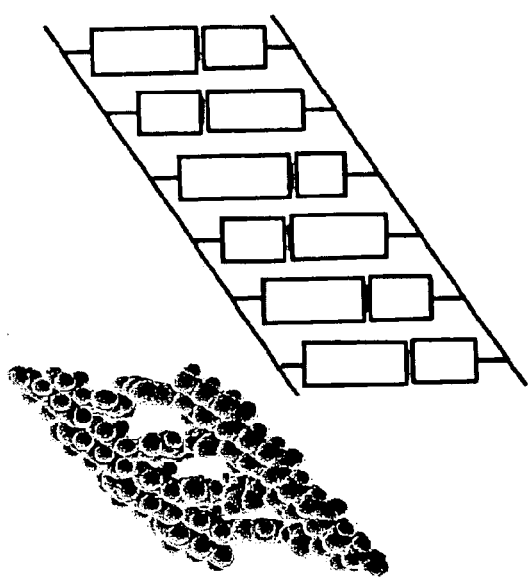
Figure 3:
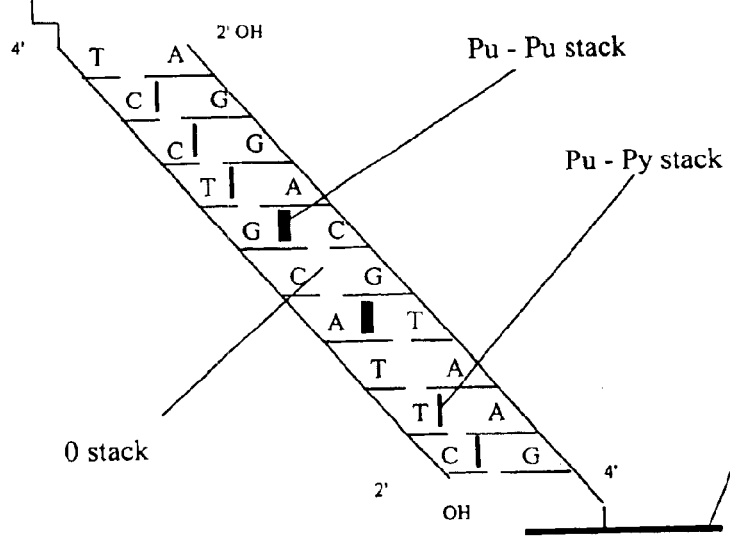

The synthetic binding systems, in particular pRNA, pDNA and CNA, form substantially more stable pairs than naturally occurring nucleic acids, such as DNA. Surprisingly, it was found that pRNA oligonucleotides composed of eight monomer units (8 mers) achieve a stability which is matched for DNA only by 25 mers. Furthermore, the stability of pRNA is determined by the number of base stacking interactions between the strands rather than by the CG content. A strong base-stacking interaction of this type between the strands via the n electron systems of the bases is not possible in the helical structure of DNA and RNA (see FIG. 3), as compared to the normal RNA/DNA base-stacking energy effects. As a result, the temperature stability increases continuously with the sequence length of pRNA, pDNA or CNA duplexes, or heteroduplexes, and this makes it possible for the synthetic binding systems to tolerate relatively high preparation and assay temperatures which are more stringent for the nucleic acid components of the conjugates.

Figure 9:
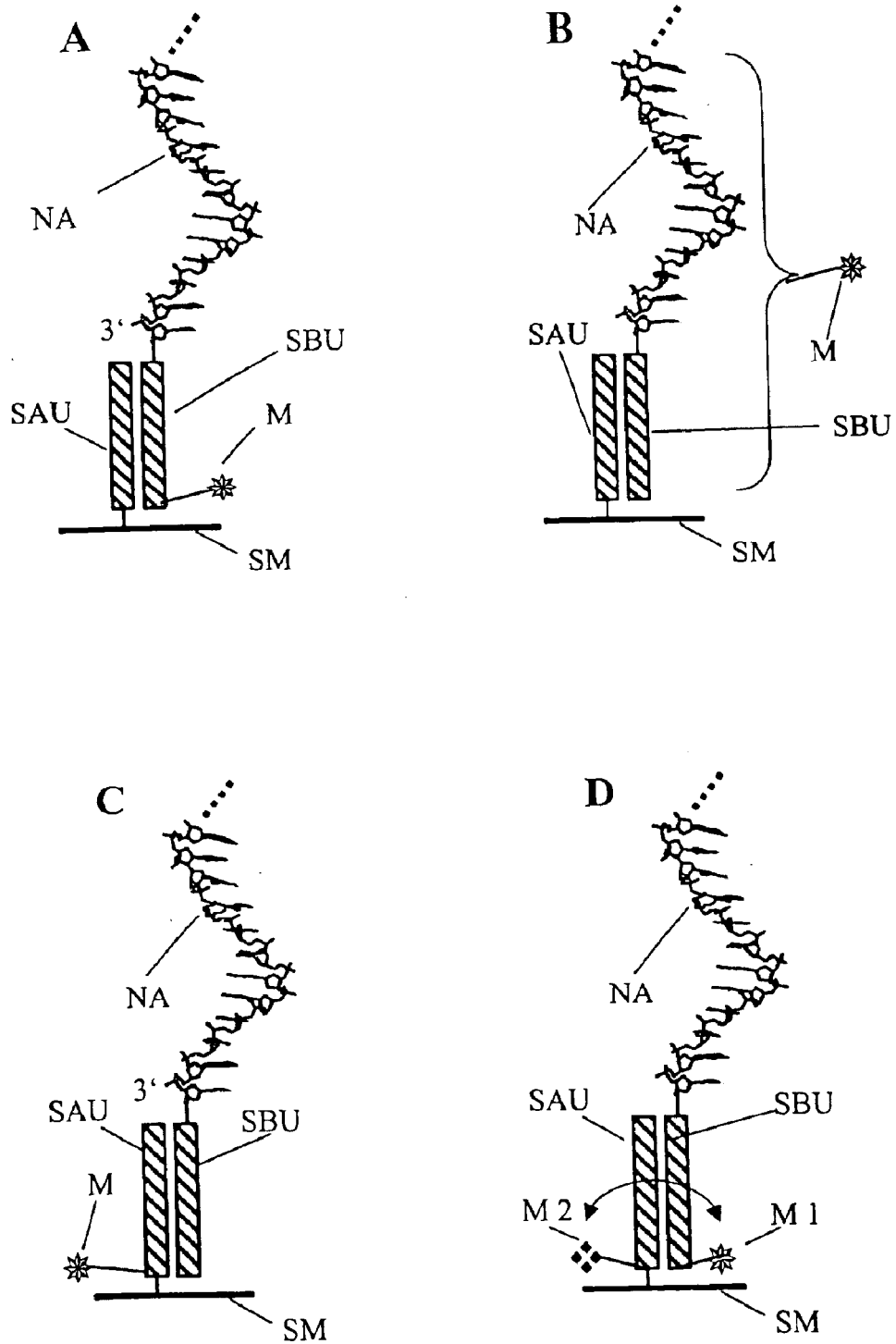
FIG. 9: A diagram of some possible embodiments of labeled synthetic binding addresses and synthetic binding units or conjugates. 9A shows a conjugate of a nucleic acid (NA) and synthetic binding unit (SBU) with a marker at the end of the binding unit, as through the end phosphate (SM=support material). B depicts the arrangement for the marker group (M) to be located at any position in the conjugate, for example through the use of a base-labeling moiety. C shows the use of a labeled synthetic binding address. D shows the joint use of two marker groups (M1 and M2) which have been adjusted to one another and give a signal in the form of fluorescence quenching or fluorescence resonance energy transfer (FRET) when a conjugate binds to the synthetic binding address.

In further embodiments, it is advantageous to use labeled conjugates of synthetic binding units and nucleic acids for monitoring, control and quality assurance of the immobilization on the support materials (see FIG. 9). Suitable labels are here in particular fluorescent dyes, dyes, radioisotopes and enzymes or micro-particles, as described above. These may be detected by fluorescent, luminescent, visible spectrum absorption or transmission (calorimetric), scintillation counting, or other suitable means. In one embodiment, the conjugate of synthetic binding unit and nucleic acid is provided with a label which is differentiable from a second label for detecting the interaction between the nucleic acid and sample components. Preferably, "quality control" labels do not interact, interfere or overlap with the second label. Detection of the labeled species on the conjugate or detection of the signal generated by the labeled species indicates whether the conjugate has been immobilized as desired. In another embodiment, the address unit of the synthetic binding systems, which has been immobilized on the support material, may be labeled with a species 1 which can interact specifically with a labeled species 2 which is connected with the conjugate of synthetic binding system and nucleic acid. See FIG. 9. Typical examples of such interactions are fluorescence quenching using quenchers and fluorescence resonance energy transfer. Preferred groups for fluorescence quenching are DABCYL and the Black Hole Quencher™ moieties. Systems of this kind advantageously indicate by the specific interaction the correct immobilization of the conjugates. Since in the case of fluorescence quenching correct immobilization leads to a decrease in the fluorescence signal, conjugates immobilized on the support material are obtained, which can be used to carry out further detection by fluorescence without interference of the fluorescence used for detecting the immobilization of the conjugates.

Supramolecular constructs of immobilized nucleic acids can thus be produced by passive binding of the SBU/NA conjugates to one or more SAUs attached to a solid support. On passive, diffusion- or convection-controlled array supports, each binding address allows only immobilization of a particular conjugate provided with the complementary part of the binding address. This results from the fact that the arrays can be exposed in each cycle only to one mixture of conjugates, which is identical over the entire array. Thus, only one cycle (M=1) is possible, as the entire array is contacted with all conjugates of a set of conjugates C. In this case therefore, the number N of binding addresses determines at the same time the number of possible different immobilized conjugates of synthetic binding units and nucleic acids, which can be immobilized and sorted on the support material (See FIG. 13).

The specific recognition of the addresses for self-organization allows the described method to immobilize in parallel N conjugates and therefore N different nucleic acids on support materials in one cycle. Likewise, all positions of such arrays can be contacted under the conditions of the application only with one type of sample at the same time and under conditions identical for all positions of the array. An advantage of the embodiment is that the user need not provide any particular apparatus or instruments, in order to generate an array of nucleic acids. The array of synthetic address units is universal and can therefore be employed for generating a multiplicity of nucleic acid arrays. The user requires only one set or set of nucleic acids individually encoded with SBUs. The nucleic acids organize and separate themselves on the support material with fixed SAUs by the specific molecular recognition of SAUs and SBUs and provide a specific immobilization.

Another advantage, as compared to spotting of individual nucleic acids, is that the user, since he applies sets of encoded nucleic acids to the support material, is able to carry out all necessary process steps on the conjugates as an entire set after conjugation of nucleic acids with SBUs. For example, instead of N individual desalting, purification or concentration steps, only one of those steps is required for the set. This makes it possible to save material and process steps. Moreover, these error-prone steps are all carried out in one step, so that there is no deviation from nucleic acid to nucleic acid. This eliminates variability caused by individual treatment of the nucleic acids, which could distort the quantitative quality of data gathered from an assay carried out on the array.

In contrast to passive array construction techniques, the generation of an array on an active location device allows the selective sorting of multiple set of conjugates. In general, active location array devices are devices in which individual locations are activatable to produce conditions favorable for SBS formation specifically at the location. Thus, the "activatable" locations are individually selectable in a controlled fashion. Such activation may be of a chemical (e.g., remotely controlled release of a hybridization promoting agent at the location) or physical nature (e.g., electric or magnetic field, IR [heat] or photonic energy, mechanical exposure [see, e.g, the device produced by Clondiag, Germany, described in WO01/02094] etc.). Of particular use and effectiveness in the array construction methods of the invention are active electronic arrays, in which individual locations on the array may be activated by an associated electrode. For example, see U.S. Pat. No. 5,605,662 "Active Programmable Electronic Devices for Molecular Biological Analysis and Diagnostics". Since active electronic arrays make it possible to actively control the electrokinetic movement and concentration, or addressing, of synthetic address units (SAU), of SBU-NA conjugates, and of samples to particular positions of the array, it is possible to immobilize N×M different conjugates on such active electronic arrays with a number N of different binding addresses, by performing M addressing cycles in succession.

Thus, when generating the array of immobilized synthetic address units for use in the active construction of arrays, several positions of the array are initially (and, optionally, simultaneously) provided with identical binding addresses. The SAUs may be spotted for high-throughput manufacturing, or may be electronically addressed, as depicted in FIG. 12A. In electronic addressing methods, in each of N steps at least M identical synthetic address units (SAU) are immobilized in parallel so that, in the end, a chip array of N different synthetic address units is obtained, with each SAU present in at least M fold repetition.

M mixtures (sets) of up to N conjugates of nucleic acids (NA) and complementary SBUs are then addressed to N array positions. In pure array0-construction embodiments where all N conjugates to be immobilized, each individual synthetic binding unit complementary to a specific address unit is present as a conjugate with a specific nucleic acid, and the group (set) of the activated locations contains the individual binding addresses at any locations where the immobilization of the corresponding nucleic acid (NA) is desired. In some assay-type embodiments, the user may not initially know if all N conjugates are present (e.g., if certain amplicons from a sample are present.) In these embodiments, the N conjugates present will form SBSs with the SAUs of the activated locations, positioning the nucleic acids from the sample.

Utilizing this system, any number of patterns for immobilization may be obtained. Usually, for immobilization of nucleic acids to form an array for later use, the set of the positions addressed in one cycle will contain each binding address only once. Addressing of the mixtures is repeated M times, and washing between the steps guarantees that the unbound conjugates of the first set are completely removed before a new set is applied and addressed. Optionally, the activated locations may be electronically washed by briefly reversing the bias of the electrode at the locations. If the active electronic array is part of a more complex sample preparation system with collection electrodes, the washed unbound conjugates may be collected at the counter-charged electrode for further disposal. If desired, SAUs, or more preferably mixtures of all SAUs used or all possible SAUs, may be attached to the counter-electrode to act as a collection "sink" for all conjugates washed from the locations by the electronic washing step.

This procedure allows a significant time reduction and simplification of the method of immobilization of different nucleic acids on an array. The advantages are best exploited if the number N of the addresses and the number M of the cycles are the square roots of the number of array positions. The optimum for a 100-position array are 10 different binding addresses employed in 10 immobilization cycles and 10 addressing cycles. Thus, to load the array with 100 different nucleic acids, 20 (=10+10) process steps are required instead of 100 individual immobilization steps for the individual nucleic acids. If each step requires 3 minutes to cycle, an array may be loaded in an hour compared to five.

Figure 12:
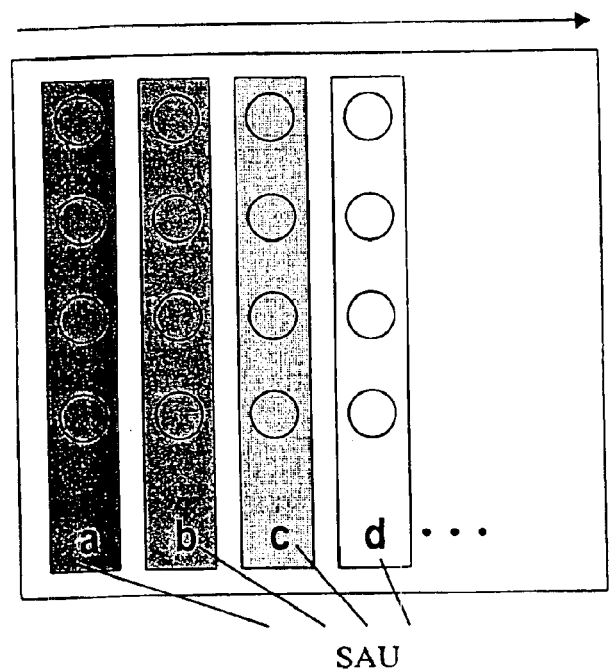
FIG. 12: A diagram showing an embodiment of the method for using synthetic address units and conjugates of synthetic binding units with nucleic acids to construct arrays on support materials. As illustrated, individual array positions can specifically and independently of one another be addressed by utilizing array surfaces with individually activatable locations, such as, for example, active electronic arrays. Initially, N different binding addresses (a, b, c, . . . N) are fixed to the surface of the support material. In this step, synthetic address units are affixed to groups of M-number of active sites utilizing the same immobilization method (e.g., biotin-streptavidin interaction, or hydrazide-active ester chemistry) in a number of steps (e.g., spotting or electronic addressing.) The immobilization is preferably carried out so that identical synthetic binding units are deposited either in rows or columns, although other geometries (e.g., squares, crosses, circles, or even randomly chosen groups of sites) may be used. Thus an array of different binding addresses is obtained, in which each unit appears in M-fold repetition (FIG. 12A). In the following steps, conjugates of nucleic acids and synthetic binding units are contacted with the array generated previously. Although this can be carried out either individually using individual SBU/NA conjugates, sets of different SBU/NA conjugates are advantageously used to immobilize up to N different SBU-encoded nucleic acids in one step. It is important that the method can only be used in those arrays in which individual array positions can be activated specifically and independently of one another, e.g., in active electronic arrays. The activated positions in each step create a condition which is favorable to the binding of the SBUs with the attached SAUs.
Figure 12:
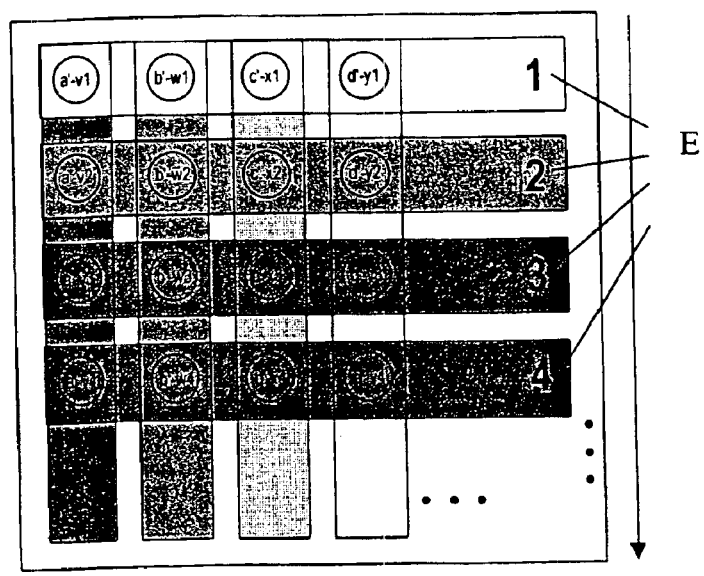

The advantage for a 100-position array is reduction by a factor of 5 in time spent. If the time required for preparing the array from SAUs is not included in the calculation, the time is reduced by a factor of 10. Since the array of SAUs is universal, the array can be prepared in advance. Because of these time savings, mega-arrays of 10,000 different nucleic acids may be generated in 5 hours (2.5 with a pre-made SAU array,) and 100,000 in 16 hours (8). For this embodiment it is unimportant whether the synthetic address units are fixed in rows and columns, as depicted in FIG. 12, or other suitable formats.

One of ordinary skill will appreciate that novel array structures are produced by the active array construction methods of the invention, as compared to those generated utilizing passive array construction techniques. In a passive array, the finished product is a set of N immobilized nucleic acids, immobilized by N distinct SBSs. In contrast, in an array produced by active construction methods, at least two different nucleic acids are immobilized by the same SBS, at different locations. In practice, large groups of 10, 20, 100 or more different nucleic acids will be immobilized at different locations by the same SBS.

Use of the Conjugates and Supramolecular Array Structures in Biological Assays

The passive and active arrays prepared according to the method can be used in in complete analogy to the arrays generated by traditional methods, in addition to having 1: several distinctive uses. The arrays can be used, for example, for SNP or STR (short tandem repeats) assays, as described by Gilles et al WO00/58522, or by Sosnowski et al. U.S. Pat. No. 6,207,373, all of which are incorporated fully herein by reference.

One application of the embodiment is the use of nucleic acids encoded with synthetic binding units for immobilizing capture stabilizer oligonucleotides for SNP assays (Gilles, P. N. et al. Nature Biotechnology, 17, 365–370 (1999)). In the SNP assay, capture stabilizer oligonucleotides or amplified nucleic acids are immobilized on an array. An array of 100 (W) different capture stabilizer oligonucleotides with 10 (N) SBS addresses is prepared, according to the method described in Example 1, by preparing conjugates form SBUs and NA. The capture stabilizer oligonucleotides used may be conjugates with a free 5' or 3' end of the nucleic acid. The capture stabilizer oligonucleotides are combined to sets of 10 (N) conjugates, each SBU in the set conjugating with a specific nucleic acid and each SBU being present in the set only once. 10 (M) sets are prepared in total. An array having 10 (N) different SAUs, with each SAU being present in 10 (M)-fold repetition, is prepared according to the method described in Example 5. The example utilizes an active location array whose positions can be contacted individually (in M cycles) with nucleic acids, conjugates, and sets, preferably an active electronic array. A first set of capture stabilizer oligonucleotides encoded with SBUs is applied to the array. This application takes place under stringency conditions which make the specific and stable binding of SBU to SAU possible. The set is contacted with a group or set of positions, in which a specific SAU occurs in each case once (or in as many times as the immobilization of a specific capture stabilizer oligonucleotide is desired). For active electronic arrays, the contacting is carried out by active electronic directing of the sets to the desired positions. The contacting can take place sequentially or in parallel for all positions of the set. The specific binding of SAU and SBU leads to the sorting and immobilization of the conjugates on the positions such that on each position one specific capture stabilizer oligonucleotide is immobilized.

The array is then washed, removing all conjugates of the first set except for the specifically immobilized conjugates. Then a second set of conjugates is applied and the above-described steps are repeated. In this way, an array is obtained after 10 (M) cycles, in which the 100 (W) different capture stabilizer oligonucleotides are immobilized, and the array can then be contacted with the sample nucleic acids to carry out a capture sandwich assay. Electronic or passive hybridization assay formats may be utilized, although electronic assay formats are advantageously utilized with multiple samples. For instance, if in the capture immobilization steps, 10 sets of 100 different captures are created simultaneously on a 1000 location device, then 10 different samples may be electronically hybridized individually to each set of captures, and then analyzed at one time in a final reporter probe hybridization step. This is an example of an assay where the array is constructed before the SBU conjugates of the array are contacted with the sample.

For immobilizing amplified nucleic acids, SBU-encoded primers are used. Such primers allow the incorporation of SBUs directly into the products of a sample nucleic acid amplification reaction. After carrying out the amplification, and optional combining of amplification products, the encoded amplified nucleic acids may be easily sorted onto sets of activated locations by their SBUs, as described above. In amplification, a single set of encoded primers may be utilized multiple amplification, and the products combined for electronic addressing, or multiple sets of encoded primers may be used for parallel amplification of nucleic acids. In multiplex reactions, treatment (e.g. desalting, purification, concentration) of the encoded amplified nucleic acids can be carried out together, leading to a reduction in the requisite steps and material. The sets are then immobilized on the array, as described above, with individual amplified nucleic acids again being immobilized on individual positions. The immobilized amplicons may then be analyzed and detected by passive or electronic hybridization of reporter/stabilizer probes, or by any other suitable method. This is an example of an assay where the array is constructed after the SBU conjugates are contacted with a sample.

As defined herein, target molecules are all compounds which can interact in a sequence-specific way with nucleic acids. For instance, target molecules may be particular nucleic acids; nucleic acid binding peptides or proteins such as: operator proteins, receptors, antibodies or functional parts thereof (e.g, Fv fragments, single-chain Fv fragments or Fab fragments,) or enzymes; and also nucleic acid binding cell components (e.g., lipids, glycoproteins, filament components), or viruses and virus components (e.g., capsids, viroids), and their derivatives, such as, for example, their acetates. Usually, however, "target molecule" refers to nucleic acids in a sample.

Also, a "sample" as used herein is any solution and/or mixture of components of natural or artificial origin, which is contacted with components of the system described here. Biological samples are often preferred, as they are the usual source of nucleic acids of interest. Biological samples for use in the invention are preferably derived from a sample selected from the group consisting of human materials, animal materials, plant materials, fungal materials, cell cultures, viral cultures, food samples, and water samples. In this context "materials" encompasses all bodily fluids, secretions, excretions, soft or hard tissues, and other organism-associated matter which may contain nucleic acids, including nucleic acids from infectious organisms. Samples may be subjected to preparation steps, such as purification of nucleic acids, amplification, or other types of enzymatic processing, before use.

Contact between potential target molecules of the sample and the NAs of the conjugates may take place before, after, or occasionally during immobilization of the NA/SBU conjugates on the support material by the SAU addresses. The presence and/or the amount of targets in the sample specifically binding to the conjugates (in the case of hybridization assays,) and/or to the presence, amount or properties of the nucleic acid (NA) itself (in the case of amplified or enzymatically modified conjugates) may then be detected by suitable means. In this context, samples include all molecules, biomolecules, mixtures, and reagents which are contacted with the nucleic acids (NA) immobilized on the support materials in order to derive information about type and/or presence or frequency of the target molecules in the sample. The samples may thus contain, in particular, labeled and/or unlabeled probes, hybridization probes, enzymes and mixtures for enzymatic reactions, or other reagents for a particular assay format. The sample components may be processed or labeled to suit the particular assay method. Suitable labels for use in assays in the invention include those listed above for conjugates and SAUs.

An additional aspect of the invention is the unique re-usability of the SAU-addressed supports. The immobilized nucleic acids of the conjugates may be relatively easily removed, in contrast to the traditional immobilization systems (e.g., covalent or as biotin/streptavidin linkages.) The binding properties of the synthetic binding systems can be influenced by setting particular stringency conditions (pH, salt content, temperature, voltage, denaturing agents, etc.) so as to remove all conjugates of synthetic binding units and nucleic acids from the support material. A preferred method is the addition of a basic solution (NaOH, KOH, $NH_4OH$, etc.) to lower the pH. Alternative methods include the use of denaturing agents such as dimethylformamide, formamide, dimethylsulfoxide. If the linkage of the synthetic address unit of the synthetic binding system to the support material is itself stable toward the conditions, then an array of immobilized synthetic address units (SAU) is retained after a such a stringency treatment. The array can then be used again for the immobilization of new conjugates of synthetic binding units (SBU) and nucleic acids (NA), just like a freshly prepared array of SAUs. Reusing the support material with the immobilized synthetic address units (SAU) saves material (support material and address units) and time when preparing the array of immobilized SAUs. The use of synthetic binding systems (SBS) is therefore advantageous compared with the use of irreversible systems such as biotin-streptavidin, for example. An example of regenerating a support material is described in Example 8. These embodiments of the invention are particularly attractive when arrays comprising intricate functional elements, such as sensor arrays or active electronic array devices, are used.

As briefly described in the SNP example, the methods of the invention also provide ways to use of conjugates of synthetic binding units and nucleic acids to sort and address to support materials, in parallel, nucleic acids which are identical as to sequence or composition, but have been obtained from different sources. This aspect is particularly useful in passive arrays, where samples cannot be sorted on supports a simply by activating particular locations in the array. For the determination of gene expression patterns, for example, the different expression of identical genes may be compared at different developmental stages, points in time after a stimulus, or in different populations, all on the same passive array. Advantageously, the informational dimensionality of the synthetic binding systems (SBS) is utilized in order to encode each gene studied in each sample with an individual address (binding unit, SBU) by utilizing SBU-conjugates as amplification primers with a cDNA sample.

After the gene amplicons of the samples of different origin are so labeled, they may be combined and further processed together. This avoids variability in treatment of the samples individually, and allows the uniform and coordinated addressing of the identical nucleic acids from different sources on the same array under precisely the same conditions. As a result, a considerably higher accuracy and lower variation (standard deviation) of the data can be achieved. In contrast to the commonly used encoding by different dyes, encoding by specific synthetic binding units (SBU) allows a considerably higher number of different simultaneously usable codes. An overlapping of visible spectrum signals is also prevented, since the encoding here serves to spatially separate the encoded nucleic acids. In contrast, dyes do not allow a separation of this kind, with the result of a frequent spectral overlapping of the dyes, which makes signal separation more difficult.

An this type of embodiment of the invention of the embodiment, is depicted in FIG. 13B. Here, different times, stages or populations of particular species of nucleic acids, for example particular genes, on an array are compared with one another. For this purpose, a standard array of attached synthetic address units may be utilized, wherein each position has a distinct SAU address. Although each gene in each sample is given a distinct SBU in this passive example, an alternative would be to use repeated addresses and SBU conjugates, as long as the addresses are handled in separate sets using an active location array. The times to be compared of one species are directed to the positions either as a mixture simultaneously, or sequentially. The specific recognition of synthetic address units by the synthetic binding units immobilizes on each array position only the conjugate which specifically pairs with the SAU at that position.

The target nucleic acids in the samples may be detected and/or quantified by means of labels, as described previously for quality control labels, either on the targets themselves or on hybridized probes. In alternative embodiments, mass spectrometry, such as MALDI-TOF, may also be utilized, with or without mass-labeling techniques. Various detection schemes have been devised for immobilized nucleic acid array formats, and the person of ordinary skill will readily appreciate their application to assays utilizing the arrays and methods of the invention.

Enzymatic Reactions Utilizing SBU-NA Conjugates

As has been previously discussed, the conjugates of the invention may be utilized in polymerase reactions for the enzymatic amplification of target nucleic acids in a sample. Surprisingly, applicants have found that conjugates comprising at least one synthetic binding unit (SBU) and at least one nucleic acid section (NA) may serve as substrates for enzymatic reactions which utilize nucleic acids as a substrate, and are thus compatible with the commonly used enzymatic processes of biotechnological production methods. For use in the enzymatic methods of the invention, the synthetic binding units of the conjugates preferably include pRNA, pDNA and/or CNA sections, these sections being able to mediate specific and reversible binding by hybridization. The nucleic acid section (NA) comprises at least one nucleotide, or nucleic acid-compatible nucleotide analog.

Thus, the basic enzymatic method of the invention is simply contacting a conjugate with at least one enzyme which utilizes naturally occurring nucleic acids as a substrate, and further contacting the mixture with other reagents necessary for the action of the enzyme. Then, the mixture is allowed to incubate under conditions suitable for the enzyme for an amount of time sufficient to effect the enzymatic modification of the conjugate. Both the reagents necessary and the conditions will vary considerably from enzyme to enzyme and between process utilized for different effects. For instance, the reagents may include an additional template nucleic acid or target nucleic acid, such as in a polymerase or template-dependent ligase reaction. Depending on the procedure, further auxiliary substances such as, for example, buffers, acids, bases, coenzymes, nuclease inhibitors, etc., may be added. Or the reagents could include nucleotides for a polymerase or terminal transferase reaction. Likewise, conditions such as temperature vary widely between "thermostable" enzymes, such as those derived tog from *Thermus aquaticus* and similar species, and heat-labile enzymes derived from, e.g., *Escherichia coli*. Applicants have found, however, that the conjugates may be used similarly to regular nucleic acid substrates. The use of the conjugates in a particular known enzymatic nucleic acid reaction will, therefore, require a minimum of experimentation. In addition, combinations of enzymes may be utilized in typical processes utilizing concerted enzyme activities, such as TMA (RNA polymerase, RNAse H and reverse transcriptase), and SDA (restriction endonuclease and polymerase).

Thus, the NA/SBU conjugates described are modified by the particular enzymes, utilizing any requisite template nucleic acids, target nucleic acids and/or nucleoside triphosphates (NTPs), depending on the method used. The term template nucleic acid means a natural nucleic acid which hybridizes to the nucleic acid section (NA) of the NA/SBU-conjugate substrate and serves as template for the linkage or synthesis of the target nucleic acid. The target nucleic acid is understood to be a natural nucleic acid which is enzymatically linked to the nucleic acid section (NA) of the NA/SBU conjugate, or is enzymatically synthesized, modified or degraded by the reaction after contacting the NA of the conjugate. The nucleic acid section (NA) may be covalently linked to the target nucleic acid, or may be hybridized to the nucleic acid section (NA) of an NA/SBU conjugate and enzymatically degraded or modified. The hybridization may also start enzymatic degradation or enzymatic modification of the nucleic acid section (NA) itself (e.g., by RNAse H activity).

The product of the enzymatic modification of the conjugate is a conjugates whose nucleic acid part has been processed. The final product will thus depend on the enzymatic process employed. Polymerase reactions (including DNA polymerase, RNA polymerase, and reverse transcriptase reactions) produce amplicons conjugated to SBUs. Ligation reactions produce SBU conjugates with additional nucleic acid sequences appended. Nuclease reactions (restriction endonuclease, exonuclease, endonuclease, RNAse, DNAse, etc.) cleave a portion of the nucleic acid section of the conjugate off. Terminal transferase reactions add one or more nucleotides to the end of the nucleic acid of the conjugate (such as for labeling or homopolymeric tailing.) And myriad other enzymatic reactions are available to phosphorylate, dephosphorylate, methylate, or otherwise modify nucleic acids.

Preferred NA/SBU-conjugates for use in the enzymatic methods include those described above. Depending on application, particular embodiments are preferred. Thus, for a polymerase or amplification reaction, the nucleic acid section of an NA/SBU conjugate should have a free 3' end. In contrast, ligases require a free phosphate at the 5' end of a nucleic acid for linkage to the 3' end of a nucleic acid. In some embodiments of the invention, this is a linkage to the 3' end of an RNA.

Exemplary enzymes include the polymerases used for amplifying nucleic acids, in particular DNA polymerases such as, for example, Taq polymerase, Vent exo polymerase, Klenow enzyme, T7 DNA polymerase, Pol 1, T4 DNA polymerase, PFV1 polymerase, Pwo polymerase or Pfu polymerase, in addition to RNA polymerases such as T7 RNA polymerase, T3 RNA polymerase, SP6 RNA polymerase and reverse transcriptase. Further exemplary enzymes include nucleases such as, for example, restriction endonucleases, exonucleases, RNases such as, for example RNase H or RNase A. These additionally include DNA and RNA ligases such as, for example, T4 DNA ligase, T4 RNA ligase, kinases, methylases, and terminal transferases or methyltransferases. Reactions with RNA ligases and DNA ligases are very useful for producing lengthened conjugates. In addition, nucleases are also useful is enzymatic modification assays, such as the quencher-release type restriction endonuclease assay depicted in FIG. 20.

In a preferred embodiment, the conjugates are enzymatically modified polymerases with the addition of nucleoside triphosphates to produce amplicons with attached SBUs. For this purpose, the NA/SBU conjugates are used as primer-substrates in polymerase reactions, with the nucleic acid section of the NA/SBU hybridized with a template nucleic acid. With the addition of polymerase and the nucleoside triphosphate monomers (NTPs), the polymerase used the template nucleic of acid strand to add complementary nucleotides to the 3' end of the nucleic acid section (NA), thus synthesizing a complementary strand. PCR and similar methodologies are preferred, and strand displacement amplification (SDA), is also preferred.

For use of NA/SBU conjugates as nucleic acid primers in enzymatic reactions of this kind, the conjugates must be stable under the reaction conditions, in particular to the repeated heating and cooling of PCR reactions. Here, the conjugates of nucleic acid sections (NA) with synthetic binding units (SBU) comprising pRNA, pDNA and/or CNA proved particularly suitable. Furthermore, the synthetic binding unit (SBU) of the conjugate must be neither an inhibitor of nor a competing substrate for the enzyme. Such a competitive in inhibition of the enzyme is advantageously not exhibited by the NA/SBU conjugates described.

Anchored strand displacement amplification (SDA) is an efficient method for multiplex amplification and discrimination of gene targets, which can advantageously utilize the novel mixed-address array structures (see FIG. 24), and branched conjugate structures (see FIG. 25) of the invention. Anchored SDA facilitates multiplex amplification because the amplification primer sets (forward and reverse) act as discrete units on at each location on the array, such as on the locations of an active electronic microchip. The amplification primer sets can be spatially separated into discrete zones on the chip by attaching the primers to specific binding units (SBU) that bind exclusively to their corresponding specific address units (SAU) a the locations. This allows the creation of discrete zones of amplification that share only enzymes and reagents, wherein the amplification products are rapidly captured by the high local concentration of primers. This localization of the primers and amplicons greatly reduces primer—primer interactions while maintaining a completely open architecture that greatly simplifies the amplification process.

FIGS. 27A through 27E illustrate the principles of SBU anchored SDA. For simplicity, this description is for a single primer pair used to amplify a single target sequence: however, the method can be extended to any number of targets and primers desired. Unique SDA primer-SBU constructs (Primer 1 and Primer 2) are electronically addressed to a specific location on the microchip. The target is introduced together with the appropriate dNTP, buffers, salts, restriction enzyme, and polymerase. The chip is heated to dissociate the double-stranded template (or this step is carried out before introducing the template), and each target is copied onto its respective SBU-anchored SDA primer by the action of the polymerase. Extension of the bumper primer creates a new double stranded target leaving the target copy (S1) attached to SBU1. A second bumper primer initiates polymerization from the distal end of S1 and creates a double stranded restriction site proximal to the SBU1 attachment point. The process repeats (nick-strand displacement synthesis cycle) to produce multiple copies of truncated S1. An analogous process can occur at Primer 2-SBU2. This completes the initiation process (Phase 1). In Phase 2, the multiple copies of S1 generated in Phase 1 are captured by Primer 2-SBU2 which subsequently may be extended by the polymerase. Inclusion of a second bumper primer and introduction of a second restriction site results in strand displacement and amplification of S2, leading to exponential amplification (Phase 3). In the absence of the second bumper primer and restriction site, the amplified S1 produced at Primer 1 is captured at Primer 2 and subsequently can be detected via the hybridization of an appropriately designed fluorescently (or otherwise) labeled reporter probe. Exponential amplification may be allowed to proceed in order to increase amplification. In this case, an additional unique capture probe-SBU construct can be used to capture the amplification products and confine them to a discrete location on the chip.

In another preferred embodiment of the invention, NA/SBU conjugates are ligated with a target nucleic acid. Here, the ligases links the free 5' end of the NA conjugate substrate with the 3' end of a target nucleic acid. Several single-strand ligases are known which advantageously require no additional template nucleic acid strand in order to ligate the two nucleic acids. RNA ligases in particular, in contrast to DNA ligases, link nucleic acids fairly efficiently without a template (cf.: England, T. E.; Nature, 275, 560–561 (1978) or England, T. E.; Bruce, A. G.; Uhlenbeck, O. C. METHODS IN ENZYMOLOGY 65(1), 65–74 (1980) or Romaniuk, Paul J.; Uhlenbeck, Olke C. Methods Enzymol. 100, 52–9 (1983)). Thus, a RNA ligase may use a conjugate of a synthetic binding unit (SBU) and a short modified nucleic acid section (NA) (as little as one nucleotide), and link the conjugate with the 3' end of an RNA. This is reaction is preferred for providing enzymatically processed conjugates for the above-described applications without using a template nucleic acid. In a variant of this embodiment, template dependent ligases which carry out a ligation of two nucleic acids are used.

In another embodiment, target nucleic acids which have been hybridized to the nucleic acid section of an NA/SBU conjugate are specifically degraded by the addition of nucleases. In this embodiment, particular preference is given to the use of restriction endonucleases and RNase H (which is double-strand specific). In these embodiments, either the nucleic acid (NA) of an NA/SBU conjugate or a target nucleic acid are degraded, cut, hydrolyzed or fragmented by the nuclease. Again, the enzyme recognizes as a substrate an NA/SBU conjugate hybridized with a target nucleic acid. For example, RNase H digests an RNA strand if this strand hybridizes to a DNA strand or an SBU-modified DNA strand (DNA/SBU conjugate). Such reactions are important, e.g., in the selective destruction of specific interfering RNAs present in a biological sample. In this example, a sample or cell containing the target RNA is mixed with a DNA/SBU conjugate whose DNA sequence is complementary to the RNA. RNase H may be added to the mixture, or the natural endogenous RNAse H activity may be used in the case of total cell extracts. Surprisingly, we can show that NA/SBU conjugates can be used in the methods without reduction in the enzymatic activity as compared with using unconjugated DNA.

Preferably, the nucleic acid section (NA) of the NA/SBU conjugates comprises at least one nucleotide, preferably 1 to 50 nucleotides. For ligation reactions, particularly preferred nucleic acid section lengths are 1 to 20 nucleotides, more preferably from 1 to 10, and most preferably from 1 to 5 nucleic acids for ligation. Preferred nucleic acid lengths are 10 to 40 nucleotides, more preferably 17 to 30 nucleotides, for polymerization and enzymatic nucleic acid degradation reactions, which require a specifically hybridized sequence. Surprisingly, applicants have found that the enzymatic activity may occur as near as less than 30, 20, 15, 10, 7, 5, or 2 nucleotides, or even 1 nucleotide of the point of conjugation between the NA and the SBU.

The enzymatic reaction can take place here using NA/SBU conjugates in solution, or immobilized NA/SBU conjugates (e.g., as in the case of enzymatic reporting by primer extension). The NA/SBU conjugates modified enzymatically in solution may then be immobilized on such surfaces buy SAU sorting after completion of the enzymatic reaction. The enzymatically obtained conjugates thus produced and immobilized can now be used to investigate samples in various assay formats as described above, or the enzymatic process itself may be utilized as part of the assay.

The synthetic binding units (SBU) themselves cannot be synthesized, amplified, modified, processed, ligated, fragmented or hydrolyzed by enzymes which are known from nucleic acid technology, such as polymerases, ligases, nucleases, restriction enzymes. This property is particularly advantageous when using conjugates of synthetic binding units and nucleic acids in enzymatic processes as described here, as the SBU is not modified, blocked, removed or processed by the enzymatic steps normally necessary for processing the sample or the nucleic acid. Thus, the use of NA/SBU conjugates is thus advantageous for the production of amplified conjugates analogously to the processes described in JP 03151900 and WO 93/25563.

EXAMPLES

Example 1

Synthesis of Conjugates of Nucleic Acids and Synthetic Binding Systems

Nucleic acids, oligonucleotides, synthetic binding systems and/or NA/SBU conjugates may be prepared according to the solid phase method on an automated synthesizer Expedite 8905 from Applied Biosystems. As utilized in the following examples, nucleic acids or oligonucleotides or the corresponding nucleic acid part of conjugates are synthesized using commercially available phosphoramidites including the reverse phosphoramidites for 5'-3' synthesis (Cruachem). For solid synthesis of nucleic acids, the synthesis cycles and conditions suggested by the manufacturer of the equipment and/or amidite supplier were used. The same is true for the use of linking building blocks, linkers, modifiers or branching amidites (as available from Glenn Research or Chemgenes).

For pRNA synthetic binding systems, the conditions and monomers described in the appropriate references are used. Although the basic method for solid-phase synthesis of the pRNA synthetic binding systems is the same, important differences compared with standard DNA synthesis are the use of adapted synthesis cycles with longer coupling time, the use of 6% dichloroacetic acid for detritylation and the use of pyridinium hydrochloride as activator. For conjugates, preference is given to using the β-cyanoethyl protective group on the phosphoramidite in conjunction with the special deprotection protocol described hereinafter. The monomers are dried beforehand in 1% vacuo over potassium hydroxide and employed as a 0.1 M solution in dry acetonitrile.

As an alternative to pRNA or pDNA synthesized by phosphoramidite chemistry, CNA with its amidic backbone may be synthesized according to the methods described in WO 99/15509, and utilized with the proper functional group modification in the coupling reactions below.

The chromatographic purification of the nucleic acids, synthetic binding systems and conjugates is carried out via RP-HPLC. Column: Merck LiChrospher RP 18 or Phenomex Luna Phenyl-Hexyl, 10 μM, analytical: 4×250 mm, flow=1.0 ml/min, semi-preparative: 10×250, flow=3.0 ml/min; buffer: A: 0.1 M triethylammonium acetate (TEAA) pH=7.0 in water, B: 0.1 M TEM pH=7.0 in acetonitrile/water (95:5); gradient: 0% B to 100% B in 100 min for analytical and preparative separations).

Electrospray mass spectra (ESI-MS) were recorded on a Finnigan LCQ apparatus in negative ionization mode. MALDI mass spectra were recorded on an Applied Biosystems Voyager DEPro.

Surprisingly, applicants have found that synthetic binding systems and conjugates are obtained in particularly good yields and in particularly good purity if a treatment with an alkylamine, such as diethylamine in dichloromethane, is carried out before deprotection and removal from the synthesis support.

General Protocol for Cyanoethyl Deprotection of Synthetic Binding Systems and Conjugates:

After solid phase synthesis according to the phosphoramidite method, the support is initially mixed with a 1.5% (w/v) solution of diethylamine in dichloromethane and shaken at room temperature, in the dark, overnight (15 h). It is also possible to rinse the synthesis support with the solution of reagents continuously instead of using a batch process. The solution is discarded and the support is washed with three portions of each of the following solvents: dichloromethane, acetone, water. During this treatment, the target molecules remain immobilized on the support. They are removed and deprotected only in the following step.

General Protocol for the Deprotection and Removal from the Synthesis Support of Synthetic Binding Systems and Conjugates (Hydrazinolysis):

The moist CPG support from the above protocol is mixed with 24% aqueous hydrazine hydrate and shaken at 4° C. for 18 h. Hydrazine is removed by solid phase extraction using Sep-Pak C18 cartridges 0.5 g Waters, No. 20515. For this purpose, the cartridge is activated by rinsing with 10 ml of acetonitrile. The hydrazine solution, diluted with five times the volume of triethylammonium bicarbonate buffer (TEAB) pH 7.0, is then loaded onto the column and the product is bound. Hydrazine is removed by washing with TEAB. The product is then diluted with TEAB/acetonitrile (1:2). Alternatively, hydrazine may be removed via RP-HPLC if a hydrazine-resistant column is used. Here, Poros R3 (Applied Biosystems) has proven useful. The elution conditions correspond to those described above. Product-containing fractions are combined and evaporated to dryness in vacuo. Analysis and preparative purification are carried out via RP-HPLC as described above. For pDNA and conjugates thereof, it is also possible to use aqueous ammonia for deprotection under the conditions common in DNA synthesis chemistry (25% solution, 55° C., overnight).

Example 1.1

Conjugates of $^{4'}$pRNA$^{2'}$-$^{5'}$DNA$^{3'}$(FIG. 1C; FIG. 2C; FIG. 2F)

The synthesis was begun with a standard solid phase DNA synthesis in the 3'-5' direction to produce the desired DNA sequence. If a linking group or branching group was desired, the appropriate synthesis building blocks were coupled to the 5' end of the product under the conditions indicated by the manufacturer. If the DNA was directly linked to pRNA through a phosphate, (FIG. 2C), no linker phosphoramidite was used. Next, the monomer building blocks of pRNA were coupled under the special conditions described above so that a SBU binding address of the desired length and sequence was obtained. If a labeled conjugate was desired, marker phosphoramidites were coupled to the conjugate in an optional last step, or utilized as an initial coupled reagent of in the synthesis. Here, the fluorescent dye phosphoramidites Cy3 and Cy5 (Amersham Pharmacia Biotech) were useful, but it is also possible to use any other suitable phosphoramidite dyes derivatives known from DNA synthesis. The conjugate was worked up, deprotected, isolated and purified as described above. Analogously, it is possible to prepare conjugates of pRNA and modified nucleic acids (e.g. 2'-O-methyl RNA). For this, 2'-O-methylphosphoramidites are coupled after the pRNA. The nucleic acid was also occasionally phosphorylated at its 5' end, as shown below. For this purpose, building blocks known to the skilled worker for introducing phosphates were used.

Applying the general protocol led to the following conjugates (bold=pRNA; *italics*=DNA):

```
IL4RP102a:  ⁴'TCCTGCATTC²'-⁵'GCA TAG AGG CAG AAT AAC AGG³'      [SEQ ID NO. 77]
retention time: 23.7 min; M calc.: 9697; M obs.: 9696

IL4RP103a:  ⁴'CTCTACGTCT²'⁵'GCA TAG AGG CAG AAT AAC AGG³'       [SEQ ID NO. 78]
retention time: 22.2 min; M calc.: 9697; M obs.: 9696

IL4RP104a:  ⁴'CCTCGTACTT²'⁵'GCA TAG AGG CAG AATAAC AGG³'        [SEQ ID NO. 79]
retention time: 21.7 min; M calc.: 9697; M obs.: 9696
```

-continued

Feto1-102a: ⁴'TCCTGCATTC²'⁵'*AGA AAT CTC ACA TGG ACA TCT TCA*³' [SEQ ID NO. 80]
retention time: 22.2 min; M calc.: 10770; M obs.: 10771

Feto2-102a: ⁴'TCCTGCATTC²'⁵'*CCT GGG CTT TGC AGC ACT TCT C*³' [SEQ ID NO. 81]
retention time: 22.3 min; M calc.: 9830; M obs.: 9822

Example 1.2

Conjugates of ⁵'DNA³'-⁴'pRNA² (FIG. 1A; FIG. 2A; FIG. 2D)

The synthesis was begun with a pRNA synthesis as described above, producing the desired pRNA SBU on the synthesis support. If a linking group or branching group was desired, the appropriate synthesis building blocks were coupled to the product using conditions indicated by the manufacturer. As above, when pRNA was directly linked to DNA by a phosphate (FIG. 2A), no further linker was added. Standard DNA phosphoramidites and synthesis cycles we re then used in order to synthesize the DNA sequence desired. If a labeled conjugate was desired, marker phosphoramidites were be coupled to the conjugate as describe d above. The conjugate was worked up, deprotected, isolated and purified as described above. Analogously, conjugates of 2'O-methyl RNA and pRNA were also obtained by using if 2'-O-methylphosphoramidites instead of DNA phosphoramidites.

Applying the general protocol led to the following conjugates (bold=pRNA; *italics*=DNA); *italics, underlined*=2'-O-methyl RNA):

IL4CS-102a:      ⁵'*CCC CAG TGC TGG*³'⁴'TCCTGCATTC²' [SEQ ID NO. 82]
retention time: — min; M calc.: 6800; M obs.: 6801

IL6CS-103a      ⁵'*ATGCTAAAGGACGTCATTGCACAATCTTAA*³'⁴'CTCTACGTCT²' [SEQ ID NO. 83]
retention time: 27 min; M calc.: 12391; M obs.: —

IL4RCS-104a:     ⁵'*GG AGT TTG TAC ATG CGG TGG AGC*³'⁴'CCTCGTACTT²' [SEQ ID NO. 84]
retention time: 27 min; M calc.: 10354; M obs.: 10353

P-OMeC-TAGGATT:  phosphate-⁵'*C*³'⁴'TAGGATT²' [SEQ ID NO. 85]
retention time: 39' min; M calc.: 3154; M obs.: 3153

Example 1.3

Conjugates of ³'DNA⁵'-⁴'pRNA²'(FIG. 1B; FIG. 2B; FIG. 2E)

This preferred embodiment was carried out analogously to the protocol described in Example 1.2. The only difference was using for the synthesis of the DNA part reverse 1, phosphoramidites (Cruachem) which allow assembly of the DNA chain in the 5'-3' direction. As in Example 1.2, this also led to a conjugate carrying a free 3' end. If the 3' end is needed, for example, for an enzymatic elongation reaction (PCR), a marker must not be attached to this phosphate. It is possible to prepare labeled conjugates with a free 3' phosphate by starting synthesis with a support-bound dye, or using labeled amidites which allow continuation of the synthesis of the molecule at the start of the solid phase synthesis. Such an amidite is Cy3 phosphoramidite (Amersham Pharmacia Biotech).

Applying the general protocol led to the following conjugates (bold=pRNA; *italics*=DNA):

IL4RP104aCy3: ³'*GGA CAA TAA GAC GGA GAT ACG*⁵'⁴'CCTCGTACTT²' [SEQ ID NO. 86]
retention time: 25 min; M calc.: 10221; M obs.: 10220

Example 1.4 pRNA-DNA Conjugate as an Example of Conjugating a Preformed Synthetic Binding System with Nucleic Acid The modified DNA oligonucleotide IL4CsrU, 5'-d(CCC CAG TGC TGG)-rU-3' [SEQ ID NO. 87] (FIG. 5) was obtained by standard DNA synthesis on a ribo-U CPG support and obtained from a commercial DNA oligo supplier (BioSpring, Frankfurt am Main). An aliquot of this nucleic acid was dissolved in an appropriate amount of deionized water to obtain a 5 mM solution. 20 µl (100 nmol) of the solution were introduced into a 1.5 ml Eppendorf microreaction vessel. 1 µl of a 0.1 M aqueous sodium periodate solution was added. The vessel was left standing at room temperature in the dark for one hour. Excess periodate was then removed by adding 1 µl of a 0.5 M sodium sulfite solution. After 15 minutes, 10 µl of a 1 M sodium phosphate buffer pH 7.4 were added and the resulting solution was transferred to a 1.5 ml Eppendorf microreaction vessel in which 8.4 nmol of a hydrazide-modified dye-labeled pRNA oligo, 4' hydrazide-TTACGGAT-Cy3 2' [SEQ ID NO. 88], had been evaporated to dryness beforehand. After mixing, the solution was left standing in the dark for one hour. Work-up: the product was purified by means of RP-HPLC. According to HPLC, the yield is 84% based on hydrazide-pRNA oligo used 4.1 nmol of conjugate were isolated, which corresponds to an isolated yield of 49% conjugate. The conjugate was characterized by means of MALDI-TOF MS: M calc.: 7210; M obs.: 7180 (broad signal); retention time: DNA: 20.4 min; hydrazide pRNA: 41.2 min; conjugate: 38.2 min All nucleic acids which contain a terminal cyclic cis-diol (e.g., RNA, aptamers and aptazymes,) can be conjugated by this method. Alternatively, a ribonucleoside may be incorporated into a DNA, PNA, or other nucleic acid terminus, or a SBU (e.g., pRNA) for use as a coupling moiety.

Figure 6:
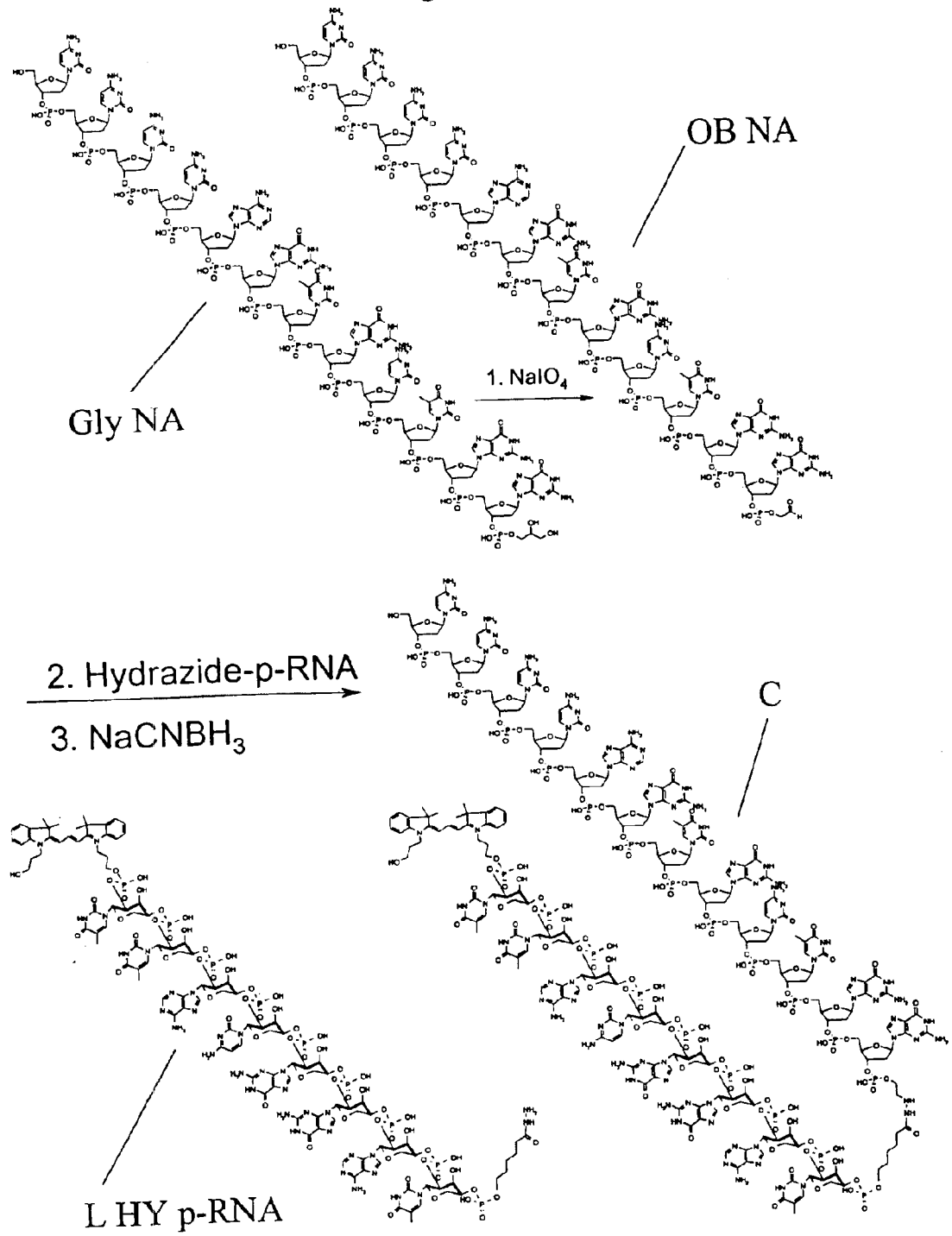
FIG. 6: An illustration of the conjugation of a 3' glyceryl-modified DNA (Gly NA) via the oxidized aldehyde DNA (OB NA) intermediate with a 2' Cy3-labeled and 4' monohydrazide-modified pRNA (L HY pRNA) to give a conjugate (C) as described in Example 1.5.

Example 1.5 pRNA-DNA Conjugate as an Example of Conjugating a Preformed Synthetic Binding System with a Nucleic Acid For this method, the DNA should contain a cis-diol, which may be provided by synthesizing the nucleic acid on glyceryl supports, e.g.: Glen Research Corp., Sterling, Va., USA; catalog No. 20-2933-41 (FIG. 6). The modified DNA oligonucleotide (e.g.: IL4CSGly, 5'-CCC CAG TGC TGG-Gly-3') (SEQ ID NO. 89] was dissolved in water and reacted with sodium periodate in a 1.5 ml Eppendorf microreaction vessel. Excess sodium periodate was removed by adding sodium sulfite solution. Sodium phosphate buffer pH 7.4 was added and the resulting solution is mixed with a hydrazide-modified pRNA oligo (e.g.: 4' hydrazide-TAGGCATT-Cy3 2') (SEQ ID NO. 90] and sodium cyanoborohydride. After mixing, the solution was left standing in the dark. The mixture as worked up by HPLC and the product was characterized by MALDI-TOF MS.

Example 1.6

Conjugation of a Nucleic Acid with a Plurality of Synthetic Binding Units

Figure 8:
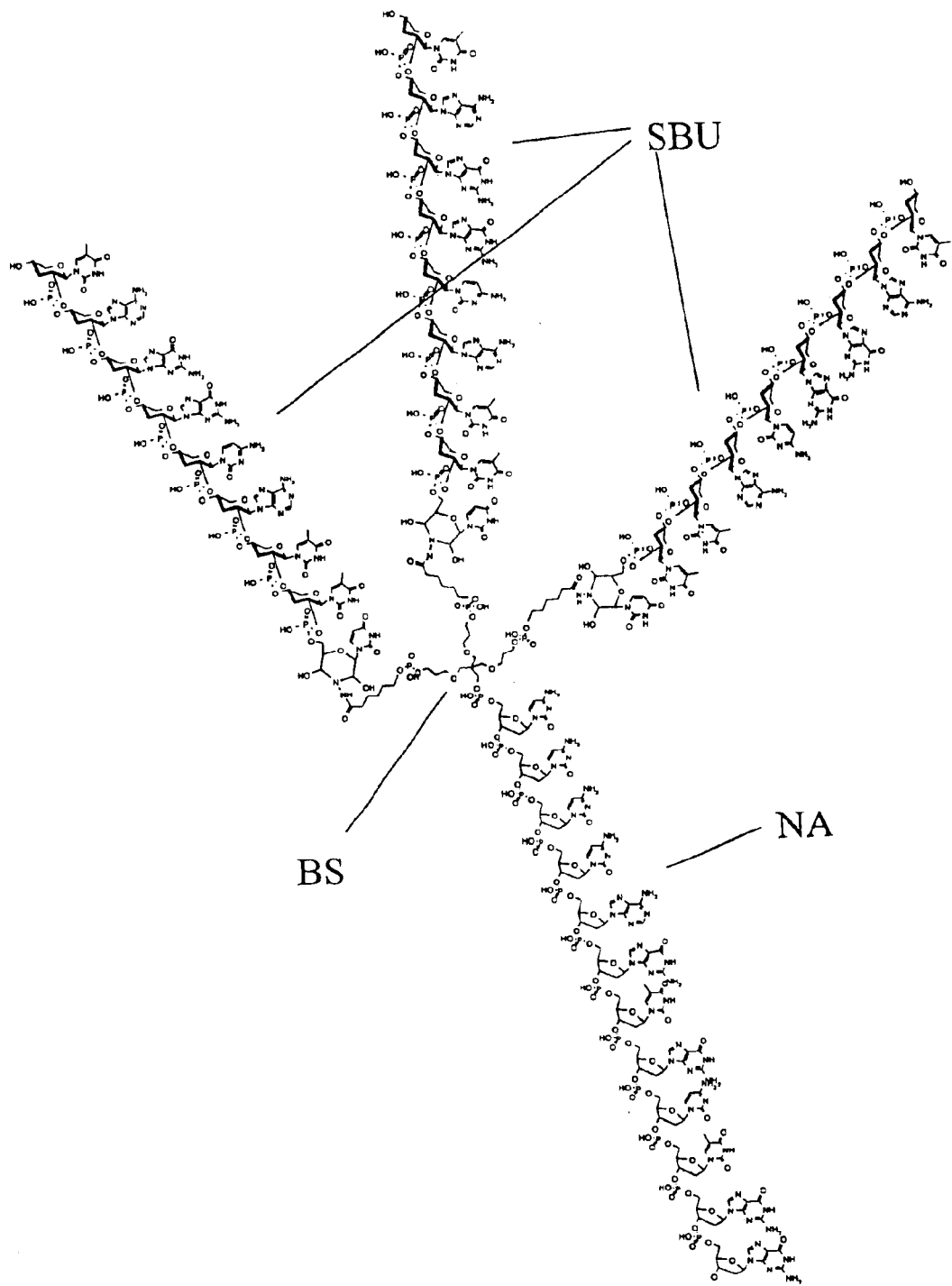
FIG. 8: An illustrative conjugate in which a nucleic acid (NA) is linked via a branching site (BS), or a branching moiety W, to a plurality of identical binding units (SBU).

Branching building blocks for use in the solid-phase synthesis of oligonucleotides are known from the literature (Shchepinov, M. S.; Udalova, I. A.; Bridgman, A. J.; Southern, E. M; Nucleic Acids Res.; 25, 4447–4454 (1997)). Coupling of a triple-branching building block (Trebler Phosphoramidite, Glen Research catalog No. 10-1922-90) and subsequent coupling of a hydrazide phosphoramidite to the 5' end of a still support-bound DNA oligonucleotide with the sequence 5'-CCC CAG TGC TGG3' [SEQ ID NO. 91] led to a nucleic acid containing three reactive hydrazide-precursor end groups. The building block was deprotected and worked up by standard methods, as described in Example 2.2. The product DNA oligonucleotide was, analogously to the method in Example 1.4, reacted with a pRNA synthetic binding unit carrying a an ribonucleotide building block on one end. The pRNA was obtained by synthesizing the SBU on a ribo-U support, and subsequent deprotection. Carrying out the conjugation as reaction according to the above mentioned protocol provided the desired product (FIG. 8).

Example 2.1

Figure 4:
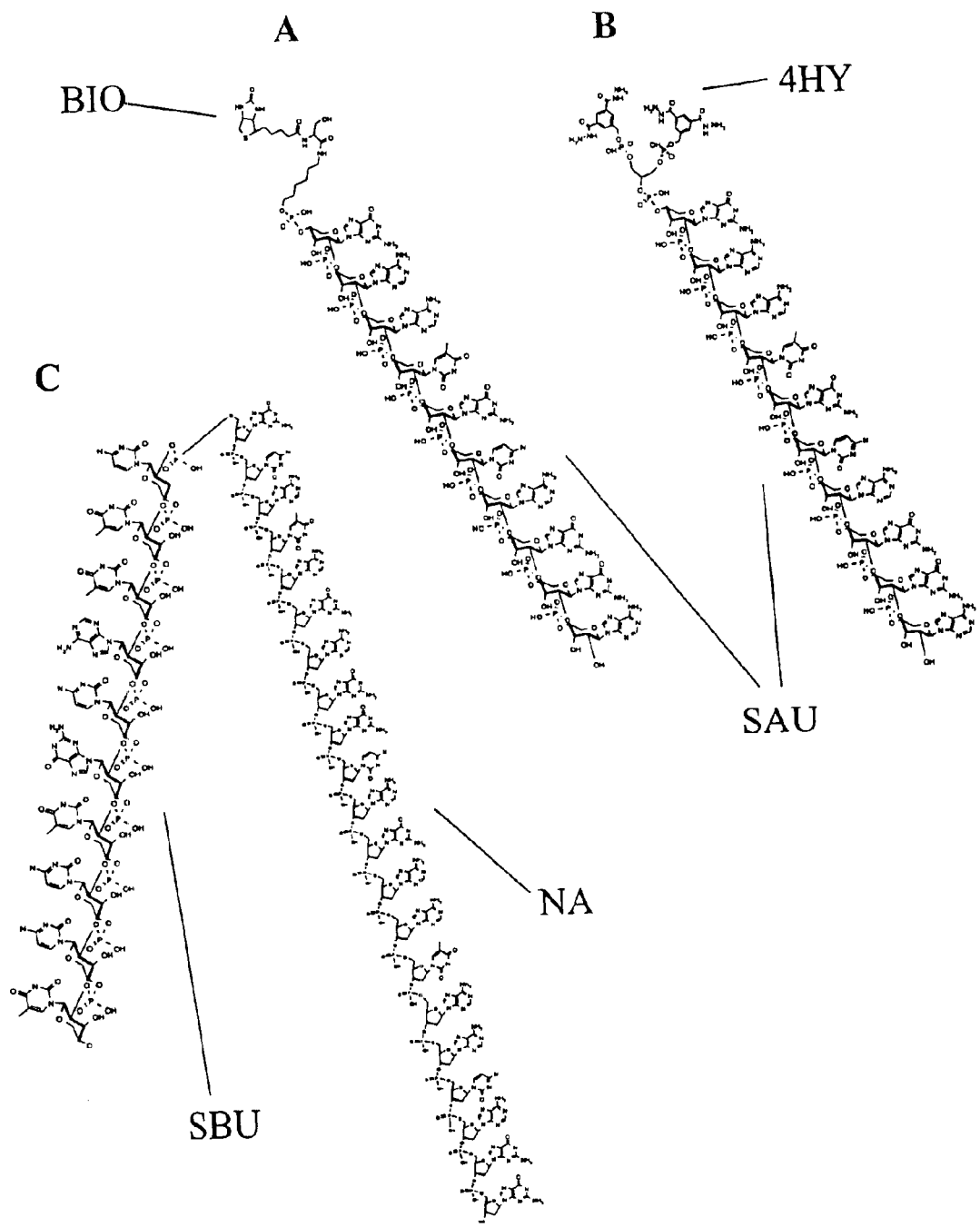
FIG. 4: An exemplary illustration of some embodiments of pRNA binding addresses and conjugates. 4A shows a synthetic address unit (SAU) having a 4' end biotin (BIO) for immobilization on support materials coated with streptavidin, 4B shows a synthetic address unit (SAU) with a tetrahydrazide (4HY) moiety for immobilization on active ester surfaces, and 4C shows a conjugate of a pRNA unit (SBU) and a DNA (NA).

Production of 4'-Biotin-pRNA as an Example of Synthesizing Synthetic Address Units (FIG. 4a)

A 10 mer pRNA address unit synthesized according to the methods described was first deprotected on the CPG support by removing its trityl protective group by dichloroacetic acid. After activation and coupling of a biotin phosphoramidite (Cruachem) with DCI and subsequent oxidation, a biotin derivative was thus introduced via a phosphodiester bond at the 4' end of the pRNA address. Chromatographic purification and analytical characterization are carried out by the protocols described.

Examples:

Bio-102b  Bio-GAATGCAGGA:    [SEQ ID NO. 92]
retention time: 25.4 min; M calc.: 3753; M:
obs.: 3754

Bio-103b  Bio-AGACGTAGAG:    [SEQ ID NO. 93]
retention time: 26.2 min; M calc.: 3753; M:
obs.: 3754

Bio-104b  Bio-AAGTACGAGG:    [SEQ ID NO. 94]
retention time: 26.1 min; M calc.: 3753; M.:
obs.: 3754

Other biotin-labeled pRNA SAUs utilizes, for example, in the surface plasmon resonance (SPR) experiments described in Example 8, below, were prepared analogously to those shown above.

Example 2.2

Production of 4' Tetrahydrazide-pRNA as an Example of Synthesizing Synthetic Address Units (FIG. 4B)

A 10 mer address unit prepared according to the pRNA synthesis protocol above was first deprotected on the CPG support by removing its trityl protective group by dichloroacetic acid. After activation and coupling of a symmetric branching phosphoramidite (ChemGenes) with pyridinium hydrochloride and subsequent oxidation, a branching diol was introduced via a phosphodiester bond at the 4' end of the pRNA. Then, a diester phosphoramidite was double-coupled to produce a branched tetraester binding address which, after cyanoethyl deprotection and subsequent hydrazinolysis, was directly reacted to give the tetrahydrazide.

Protocol for preparing the diester phosphoramidite diethyl 5-[[[[bis(1-methylethyl)amino](2-cyanoethoxy)phosphino]oxy]methyl]-1,3-benzenedicarboxylate: 1.29 g (5 mmol) of diethyl 5-(hydroxymethyl)isophthalate [252.27] (98%, Aldrich; CAS 181425-91-2) were dissolved in 20 ml of dry dichloromethane at room temperature and mixed with 2.59 g (40 mmol, 4 eq) of N-ethyldiisopropylamine [129.25] and 1.3 g (11 mmol, 1.1 eq) of 2-cyanoethyl N,N-diisopropylchlorophosphoramidite [236.68] (Aldrich; CAS 89992-70-1). After 15 min at room temperature, thin layer chromatography (ethyl acetate/n-heptane (1:4) showed completion of the reaction. The mixture was concentrated and mixed with 30 ml of ethyl acetate/n-heptane (2:3). The precipitated hydrochloride was removed by filtration. The filtrate was concentrated and applied directly to a chromatography column. Elution with ethyl acetate/n-heptane (1:4) gave 1.6 g (70%) of diethyl 5-[[[[bis(1-methylethyl)amino](2-cyanoethoxy)phosphino]oxy]methyl]-1,3-benzenedicarboxylate as a colorless oil. $C_{22}H_{33}N_2O_6P$; $^1$H-NMR 8.59 (m, 1H, arom.), 8.21 (m, 2H, arom.), 4.87–4.75 (m, 2H, $CH_2$ cyanoethyl), 4.41 (q, J=6.98 Hz, 4H, $CH_2$ ethyl), 3.95–3.80 (m, 2H, 2×CH i-Pr), 3.74–3.61 (m, 2H, $CH_2$ cyanoethyl), 2.66 (t, J (P,H)=6.45 Hz, 2H, O—$CH_2$-arom), 1.41 (t, J=6H, 2×$CH_3$ ethyl), 1.23–1.20 (m, 12H, $CH_3$, i-Pr): $^{31}$P-NMR (CDCl$_3$): δ 149.94; $^{13}$C-NMR (CDCl$_3$): δ=165.8 (C=O), 140.2 (C—$CH_2$—O—P), 132.1 (2×C arom.), 131.1 (2×C—H arom), 129.7 (C H arom), 117.6 (CN), 64.7 (P—O—$CH_2$-arom), 61.4 (2×$CH_2$ ethyl), 58.6 (O—$CH_2$—$CH_2$—CN), 43.4 (2×C—H i-Pr), 24.7 (4×$CH_3$ i-Pr), 20.5 (O—$CH_2$—$CH_2$—CN), 14.4 ($CH_3$ ethyl); HRMS 453.2156 ([M+H]+$C_{22}H_{34}N_2O_6P$ calculated: 453.21545). Chromatographic purification and analytical characterization were carried out according to the protocols described above.

Examples:

```
4HY-102b  4HY-GAATGCAGGA:      [SEQ ID NO. 95]
retention time: 20.7 min; M calc.: 3985; M:
obs.: 3986

4HY-103b  4HY-AGACGTAGAG:      [SEQ ID NO. 96]
retention time: 20.8 min; M calc.: 3985; M:
obs.: 3986

4HY-104b  4HY-AAGTACGAGG:      [SEQ ID NO. 97]
retention time: 20.8 min; M calc.: 3985; M:
obs.: 3986
```

Example 3.1

Immobilization of Hydrazide-Modified SAUs on Active Electronic Arrays

Experiments were carried out on a NanoChip™ Molecular Biology Workstation (Nanogen Inc. San Diego, USA). The immobilization of hydrazide-modified SAUs uses arrays carrying a chemical modification which can react with the hydrazide. A array modification for such use is an activated es ter-modified permeation layer array as described in (PCT/US00/22205). Here, the surface of the support material was coated with polyacrylamide into which N-hydroxysuccinimide activated esters have been copolymerized. Immobilization efficiency was improved by using SAUs carrying on one end several (e.g. four) hydrazides (see Example 2.2). The hydrazide-modified SAUs were dissolved in 50 mM histidine buffer at a concentration of 500 nM and electronically addressed to the desired locations on the device at 2.2 V for 3 minutes. They were attached at the locations via by reacting the hydrazides with the activated esters to form covalent bonds.

The arrays obtained in this way were used for the immobilization of conjugates in the same manner as the arrays having SAUs fixed via a non-covalent biotin/streptavidin interaction.

Example 3.2

Immobilization of Biotinylated Synthetic Address Units on Active Electronic Arrays Experiments are carried out on a NanoChip™ Molecular Biology Workstation and NanoChip™ cartridges (Nanogen Inc. San Diego, USA). The immobilization of the synthetic address units on the array used standard electronic addressing protocols as are stated by the manufacturer for DNA. Briefly, biotinylated pRNA address units were dissolved in 50 mM β-histidine at a concentration of 500 nM. This solution was applied to the chip and the address units were directed electronically to the desired locations. For this purpose, the desired array locations are biased at an electric potential which leads to concentration of the SAUs. For negatively charged synthetic address units, e.g., pRNAs, the positions were biased positive. A good addressing procedure for pRNA and pDNA was addressing with +2.0 V for 1 minute, in the experience of the applicants.

The array of synthetic address units obtained in this way, or by the hydrazide attachment method above, can be used universally. Depending on the set of conjugates applied, such an array becomes a special application-based array.

Example 4

Selective Immobilization of 10 Different Conjugates on Active Electronic Arrays

From the synthetic binding systems described in Example 8, 10 (N=10) systems were selected, which were substantially orthogonal, and do not significantly interact with one another (102a,b; 103a,b; 104a,b; 106a,b; 109a,b; 110a,b; 117a,b; 119a,b; 120a,b; 122a,b). The immobilization schedule and addressing schedule are depicted in the table below.

The synthetic address units were attached to locations on a NanoChip™, as in Example 3.2, by means of biotin-streptavidin. The 10 different address units ("b" series) were loaded row by row such that identical address units were fixed at each of the 10 locations in one row. In order to ensure that each of the 10 address units is loaded only onto one row, the 10 active SAU attachment steps were carried out successively, with rinsing between the steps.

|    | 1    | 2    | 3    | 4    | 5    | 6    | 7    | 8    | 9    | 10   |
|----|------|------|------|------|------|------|------|------|------|------|
| 1  | 102b | 102b | 102b | 102b | 102b | 102b | 102b | 102b | 102b | 102b |
| 2  | 103b | 103b | 103b | 103b | 103b | 103b | 103b | 103b | 103b | 103b |
| 3  | 104b | 104b | 104b | 104b | 104b | 104b | 104b | 104b | 104b | 104b |
| 4  | 106b | 106b | 106b | 106b | 106b | 106b | 106b | 106b | 106b | 106b |
| 5  | 109b | 109b | 109b | 109b | 109b | 109b | 109b | 109b | 109b | 109b |
| 6  | 110b | NA   | 110b | 110b | 110b | 110b | 110b | 110b | 110b | 110b |
| 7  | 117b | 117b | 117b | 117b | 117b | 117b | 117b | 117b | 117b | 117b |
| 8  | 119b | 119b | 119b | 119b | 119b | 119b | 119b | 119b | 119b | 119b |
| 9  | 120b | 120b | 120b | 120b | 120b | 120b | 120b | 120b | 120b | 120b |
| 10 | 122b | 122b | 122b | 122b | 122b | 122b | 122b | 122b | 122b | 122b |

The complementary binding units used were the 10 pRNA sequences ('a' series) complementary to the 10 address units. For detection on the array, the binding units were labeled at the 2' end with a dye moiety (Cy3). The affinities of the synthetic binding systems were checked using a voltage of +2.0 V for in 180s. The concentration of the individual binding units was in all cases 100 nM in 50 mM histidine buffer. Each complementary binding unit was actively addressed column by column so that it was possible to study the binding of one binding unit to all 10 address units with one electrical activation. Using 10 active addressing steps successively (M=10), it was thus possible to test 10 synthetic binding units for their pairing properties with the 10 address units. The time for this parallel assay was 2 hours, while assaying 10 pairs on the surface plasmon resonance system (Example 8) required 50 hours. Here, the time advantage of encoding realized by the possible parallelization of working steps becomes immediately obvious. After actively directing the complementary binding addresses, the chip was washed with 40 ml of 50 mM NaCl HBS buffer and then read by the Nanogen workstation reader. The fluorograph obtained is shown in FIG. 15. Only the desired pairings show intense fluorescence. The fields with the heavy border in the table in FIG. 15 represent those positions of the Nanogen chip on which synthetic binding systems are located in which the attached SAUs and the addressed SBUs correspond to each other.

Example 5

Immobilization of Capture/Stabilizer Oligonucleotides on Active Electronic Arrays via Synthetic Binding Systems One hundred different capture/stabilizer oligonucleotides are immobilized on an active electronic array as follows: first an array of fixed SAUs is generated using 10 different SAUs (N=10). 10 array locations in columns (cf. FIG. 12) are in each case provided with identical SAUs. The preparation of such an array is described in Example 3.1 and Example 3.2.

Then, the conjugates of capture/stabilizer oligonucleotides and SBUs are prepared, as described in Example 1. Each oligonucleotide carries a specific SBU address. The conjugates are combined to sets of 10 conjugates each (in total 10 sets, M=10), each SBU having a particular NA conjugated to it in each set. The sets are dissolved in 50 mM histidine buffer at a concentration of 10 nM (per conjugate) and directed electronically to a first set of 10 positions. Care is taken here that each SAU appears only once in the set of addressed locations. An easy method of assuring this is, as depicted in FIG. 12, by attaching the SAUs in columns and addressing the sets of conjugates in rows. Electronic directing takes place at +2.1 V for 120 seconds. The sets may be directed to the positions either sequentially, partly in parallel, or simultaneously for all positions of the set. The specific recognition of SAU and SBU immobilizes only the conjugate with the matching recognition sequence on each individual location: in other words the set is sorted into individual conjugates and the individual conjugates are immobilized on specific array locations. Then the array is washed with 50 mM histidine buffer and the next set of conjugates is applied. Again, directing to 10 positions and washing is carried out. After 10 cycles (M=10), 100 positions are occupied by different capture/stabilizer oligonucleotides, and the array can be used for hybridization or other assays. Compared with sequentially loading an array with 100 individual nucleic acids, which requires 100 cycles, the number of cycles is reduced by 90%.

Using the nucleic acid array obtained in this way, it is possible to carry out all experiments and assays which can be carried out using an array prepared via direct immobilization of nucleic acids on the array positions, such as gene expression, SNP, and STR assays.

Example 5.2

Parallel Immobilization of Mixtures of pRNA-DNA Conjugates: Selectivity of Immobilization On an active electronic array 5 pRNA SAUs ("b" Series, sequences 102b, 103b, 104b, 106b, 109b) were attached in rows using biotin/streptavidin interactions as described previously (Example 2.1). A standard Streptavidin/Agarose NanoChip cartridge is used. Attaching conditions: 50 mM Histidine 500 nM SAU, 2.0 V, 60 s.

Five different mixtures of 10 pRNA-DNA conjugates were made by mixing individually synthesized conjugates (Example 1.2) at 50 nM each. Within each mixture 9 conjugates were Cy3 labeled and one was unlabeled. Each mixture was addressed simultaneously to a column of locations with five different pRNA addresses. Addressing conditions were 50 mM Histidine, 50 nM for each conjugate, 2.0 V, 180 s.

Mixture 1: DTD-102a; EH1-103a-Cy3; CYP19-104a-Cy3; 178850-106a-Cy3; 192610-109a-Cy3; 195088-110a-Cy3; EPHX2-117a-Cy3; NAT12-119a-Cy3; GSTA1-120a-Cy3; NAT1 B-122a-Cy3

Mixture 2: DTD-102a-Cy3; EH1-103a; CYP19-104a-Cy3; 178850-106a-Cy3; 192610-109a-Cy3; 195088-110a-Cy3; EPHX2-117a-Cy3; NAT12-119a-Cy3; GSTA1-120a-Cy3; NAT1B-122a-Cy3

Mixture 3: DTD-102a-Cy3; EH1-103a-Cy3; CYP19-104a; 178850-106a-Cy3; 192610-109a-Cy3; 195088-110a-Cy3; EPHX2-117a-Cy3; NAT12-119a-Cy3; GSTA1-120a-Cy3; NAT1 B-122a-Cy3

Mixture 4: DTD-102a-Cy3; EH1-103a-Cy3; CYP19-104a-Cy3; 178850-106a; 192610-109a-Cy3; 195088-110a-Cy3; EPHX2-117a-Cy3; NAT12-119a-Cy3; GSTA1-120a-Cy3; NAT1B-122a-Cy3

Mixture 5: DTD-102a-Cy3; EH1-103a-Cy3; CYP19-104a-Cy3; 178850-106a-Cy3; 192610-109a; 195088-110a-Cy3; EPHX2-117a-Cy3; NAT12-119a-Cy3; GSTA1-120a-Cy3; NATIB-122a-Cy3

Unbound material was washed off and the Cy3 fluorescence of the array is imaged on an NanoChip Molecular Biology Workstation. The results are listed in the following Table. (See FIG. 18). The one pad per column which corresponds to the SAU/SBU of the unlabeled conjugate within the mixture showed low fluorescence: This demonstrated that there was little unspecific binding of the 9 other conjugates to these positions.

|      | 1      | 2      | 3      | 4      | 5      |
|------|--------|--------|--------|--------|--------|
| 102b | 97.2   | 1048.6 | 1048.6 | 1048.6 | 1048.6 |
| 103b | 1048.6 | 211.1  | 1048.6 | 1048.6 | 1048.6 |
| 104b | 1048.6 | 1048.6 | 233.0  | 1048.6 | 1048.6 |
| 106b | 1048.6 | 1048.6 | 1048.6 | 171.3  | 1048.6 |
| 109b | 1048.6 | 1048.6 | 1048.6 | 1048.6 | 179.6  |

Note:
A fluorescence value of 1048.6 indicates saturated fluorescence. The real value is higher then.

As a second step, a mixture of Cy5 labeled DNA strands complementary to the DNA part of the conjugates (Cy5-DTD-Comp, Cy5-EH1-Comp; Cy5-CYP19-Comp, Cy5-178850-Comp; Cy5-192610-Comp.) was addressed simultaneously to the columns of immobilized conjugates (25 nM per DNA, 2.0 V, 180 s). Again Unbound material was washed off and the Cy5 fluorescence was imaged. Fluorescence signals at all positions showed that conjugates capture complementary DNA. The pads with unlabeled conjugates also captured DNA complements, demonstrating that the labels did not have any effect on hybridization efficiency.

|      | 1      | 2      | 3      | 4      | 5      |
|------|--------|--------|--------|--------|--------|
| 102b | 1048.6 | 1048.6 | 1048.6 | 1048.6 | 1048.6 |
| 103b | 724.6  | 663.4  | 631.1  | 868.7  | 1048.6 |
| 104b | 666.0  | 611.3  | 525.1  | 552.9  | 557.4  |
| 106b | 611.2  | 692.6  | 488.1  | 540.4  | 682.6  |
| 109b | 541.6  | 614.7  | 552.4  | 611.1  | 668.9  |

Note:
A fluorescence value of 1048.6 indicates saturated fluorescence. The real value is higher then.

Sequences:

| Name | Sequence *italics* = DNA (5#-3'); bold = pRNA (4'-2') | |
|---|---|---|
| 102b | Bio-4'GAATGCAGGA2' | [SEQ ID NO. 98] |
| 103b | Bio-4'AGACGTAGAG2' | [SEQ ID NO. 99] |
| 104b | Bio-4'AAGTACGAGG2' | [SEQ ID NO. 100] |
| 106b | Bio-4'AGGCATAAAG2' | [SEQ ID NO. 101] |
| 109b | Bio-4'AACAAGTGGG2' | [SEQ ID NO. 102] |
| DTD-102a | 5'*CTCAACTGACATATAGCATTGGGCA*3'-4'TCCTGCATTC2' | [SEQ ID NO. 103] |
| EH1-103a | 5'*ACCCTCACTTCAAGACTAAGATTGAAGGTA*3'-4'CTCTACGTCT2' | [SEQ ID NO. 104] |
| CYP19-104a | 5'*ACCCGGTTGTAGTAGTTGCAGGCAC*3'-4'CCTCGTACTT2' | [SEQ ID NO. 105] |
| 178850-106a | 5'*ACAACAATTTGAAGCTTCTGTAATTTTG*3'-4'CTTTATGCCT2' | [SEQ ID NO. 106] |
| 192610-109a | 5'*TGTCAGCCTTGCTACTTGAAGGTAC*3'-4'CCCACTTGTT2' | [SEQ ID NO. 107] |
| 195088-110a | 5'*CCCCTGTAGGTTGCTTAAAAGGGAC*3'-4'TCTGCTCATC2' | [SEQ ID NO. 108] |
| EPHX2-117a | 5'-*GCATGGATGGCAGCATTGTTCTGAA*-3'-4'TTCTATACTC2' | [SEQ ID NO. 109] |
| NAT12-119a | 5'-*GAGGTTCAAGCGTAAATAAGTATATTT*-3'-4'TGGTCGGTTG2' | [SEQ ID NO. 110] |
| GSTA1-120a | 5'-*CTTCTTTCAGTGGGAGGGAACTATTGAG*-3'-4'TGGTTATCTG2' | [SEQ ID NO. 111] |
| NAT1B-122a | 5'-*ACATTTATTATTATTATTATTATTATTTG*-3'-4'CTCCATGTTC2' | [SEQ ID NO. 112] |
| DTD-102a-Cy3 | 5'*CTCAACTGACATATAGCATTGGGCA*3'-4'TCCTGCATTC2'-Cy3 | [SEQ ID NO. 113] |
| EH1-103a-Cy3 | 5'*ACCCTCACTTCAAGACTAAGATTGAAGGTA*3'-4'CTCTACGTCT2'-Cy3 | [SEQ ID NO. 114] |
| CYP19-104a-Cy3 | 5'*ACCCGGTTGTAGTAGTTGCAGGCAC*3'-4'CCTCGTACTT2'-Cy3 | [SEQ ID NO. 115] |
| 178850-106a-Cy3 | 5'*ACAACAATTTGAAGCTTCTGTAATTTTG*3'- 4'CTTTATGCCT2'-Cy3 | [SEQ ID NO. 116] |
| 192610-109a-Cy3 | 5'*TGTCAGCCTTGCTACTTGAAGGTAC*3'-4'CCCACTTGTT2'-Cy3 | [SEQ ID NO. 117] |
| 195088-110a-Cy3 | 5'*CCCCTGTAGGTTGCTTAAAAGGGAC*3'-4'TCTGCTCATC2'-Cy3 | [SEQ ID NO. 118] |
| EPHX2-117a-Cy3 | 5'-*GCATGGATGGCAGCATTGTTCTGAA*-3'-4'TTCTATACTC2'-Cy3 | [SEQ ID NO. 119] |
| NAT12-119a-Cy3 | 5'-*GAGGTTCAAGCGTAAATAAGTATATTT*-3'-4'TGGTCGGTTG2'-Cy3 | [SEQ ID NO. 120] |
| GSTA1-120a-Cy3 | 5'-*CTTCTTTCAGTGGGAGGGAACTATTGAG*-3'-4'TGGTTATCTG2'-Cy3 | [SEQ ID NO. 121] |
| NAT1B-122a-Cy3 | 5'-*ACATTTATTATTATTATTATTATTATTTG*-3'-4'CTCCATGTTC2'-Cy3 | [SEQ ID NO. 122] |
| Cy5-DTD-Comp | 5'-Cy5-TGCCCAATGCTATATGTCAGTTGAG-3' | [SEQ ID NO. 123] |
| Cy5-EH1-Comp | 5'-Cy5-TACCTTCAATCTTAGTCTTGAAGTGAGGGT-3' | [SEQ ID NO. 124] |
| CyS-CYP19-Comp | 5'-Cy5-GTGCCTGCAACTACTACAACCGGGT-3' | [SEQ ID NO. 125] |
| Cy5-178850-Comp | 5'-Cy5-CAAAATTACAGAAGCTTCAAATTGTTGT-3' | [SEQ ID NO. 126] |
| Cy5-192610-Comp | 5'-Cy5-GTACCTTCAAGTAGCAAGGCTGACA-3' | [SEQ ID NO. 127] |
| Cy5-195088-Comp | 5'-CY5-GTCCCTTTTAAGCAACCTACAGGGG3' | [SEQ ID NO. 128] |
| Cy5-EPHX2-Comp | 5'-CY5-TTCAGAACAATGCTGCCATCCATGC-3' | [SEQ ID NO. 129] |
| Cy5-NAT12-Comp. | 5'-CY5-AAATATACTTATTTACGCTTGAACCTC-3' | [SEQ ID NO. 130] |
| Cy5-GSTA1-Comp. | 5'-Cy5-CTC AAT AGT TCC OTO CCA CTG AM GM G-3' | [SEQ ID NO. 131] |
| Cy5-NAT1B-Comp. | 5'-Cy5-CM ATA ATA ATA ATA ATA ATA ATA ATA AAT GT-3' | [SEQ ID NO. 132] |

Example 5.3

Parallel Immobilization of Mixtures of p-RNA-DNA Conjugates Selectivity of Immobilization with 10 SAU/SBU Step 1: p-RNA Synthetic Address Unit (SAU) Array Construction On an active electronic array 10 p-RNA SAU's ("b" Series, sequences 102b, 103b, 104b, 106b, 109b, 110b, 117b, 119b, 120b, 122b) were attached in rows by biotin/streptavidin attachment (Example 2.1). A standard Streptavidin/Agarose NanoChip cartridge was used. Attaching conditions: 50 mM Histidine 250 nM SAU, 2.0 V, 60 s. An array with 10 identical p-RNA addresses in each row, each row having a distinct p-RNA address, was obtained.

Step 2: DNA Array Construction

One mixture of 10 p-RNA-DNA conjugates was made by mixing individually synthesized conjugates (Example 1.2) at 40 nM each. Within the conjugate mixture each DNA sequence was coded by a specific p-RNA SBU (DTD-102a, EH1-103a, CYP19-104a, 178850-106a, 192610-109a, 195088-110a, EPHX2-117a, NAT12-119a, GSTA1-120a, NAT1B-122a). The conjugate mixture was actively addressed simultaneously to all 10 pads of one column, with a set of 10 locations with 10 different p-RNA addresses. Ten columns were addressed sequentially with the same conjugate mixture. Note: by using 10 different mixtures of DNA-p-RNA conjugates (wherein within each mixture each DNA is coded by a different p-RNA SBU but in different mixtures different DNA's are coded with repeating p-RNA SBU's) instead of one conjugate mixture it, is possible to construct an array of 100 different DNA sequences with the same number of addressing steps and within the same time as in this experiment. Addressing conditions were 50 mM Histidine, 40 nM for each conjugate, 2.0 V, 180 s) The conjugate mixture was heated to 95° C. for 5 min and rapidly chilled on an ice bath immediately prior addressing in order to disrupt secondary structures and putative DNA—DNA interactions. The sequences of the conjugates in the mixture were as follows:

| | | |
|---|---|---|
| DTD-102a | 5'*CTCAACTGACATATAGCATTGGGCA*3'-4'TCCTGCATTC2' | [SEQ ID NO. 133] |
| EH1-103a | 5'*ACCCTCACTTCAAGACTAAGATTGAAGGTA*3'-4'CTCTACGTCT2' | [SEQ ID NO. 134] |
| CYP19-104a | 5'*ACCCGGTTGTAGTAGTTGCAGGCAC*3'-4'CCTCGTACTT2' | [SEQ ID NO. 135] |
| 178850-106a | 5'*ACAACAATTTGAAGCTTCTGTAATTTTG*3'-4'CTTTATGCCT2' | [SEQ ID NO. 136] |
| 192610-109a | 5'*TGTCAGCCTTGCTACTTGAAGGTAC*3'-4'CCCACTTGTT2' | [SEQ ID NO. 137] |
| 195088-110a | 5'*CCCCTGTAGGTTGCTTAAAAGGGAC*3'-4'TCTGCTCATC2' | [SEQ ID NO. 138] |
| EPHX2-117a | 5'-*GCATGGATGGCAGCATTGTTCTGAA*-3'-4'TTCTATACTC2' | [SEQ ID NO. 139] |
| NAT12-119a | 5'-*GAGGTTCAAGCGTAAATAAGTATATTT*-3'-4'TGGTCGGTTG2' | [SEQ ID NO. 140] |
| GSTA1-120a | 5'-*CTTCTTTCAGTGGGAGGGAACTATTGAG*-3'-4'TGGTTATCTG2' | [SEQ ID NO. 141] |
| NAT1B-122a | 5'-*ACATTTATTATTATTATTATTATTATTTG*-3'-4'CTCCATGTTC2' | [SEQ ID NO. 142] |

(Bold: p-RNA; *Italics*: DNA)

An array of DNA captures immobilized on an active electronic Nanogen Chip was obtained. Within each row of the chip the same DNA capture sequence was immobilized.

Step 3: Probing

To show the selectivity of the immobilization of the DNA capture sequences the chip was probed with 10 mixtures of unlabeled, Cy3, and Cy5 labeled DNA reporter sequences complementary to the DNA capture sequences immobilized by the SBSs.

The mixtures were as follows:

a) Within each mixture one DNA reporter was unlabeled (Mixture No. 1: reporter No. one; mixture No. 2: reporter No. 2; . . . ; mixture No. 10: reporter No. 10)

b) Within each mixture every second reporter sequence was labeled with the same type of fluorescent dye, and adjacent reporters has different dyes, within the mixtures.

| | | |
|---|---|---|
| DTDcomp | 5'-TGC CCA ATG CTA TAT GTC AGT TGA G-3' | [SEQ ID NO. 143] |
| EH1comp | 5'-TAC CTT CAA TCT TAG TCT TGA AGT GAG GGT-3' | [SEQ ID NO. 144] |
| CYP19comp | 5'-GTG CCT GCA ACT ACT ACA ACC GGG T-3' | [SEQ ID NO. 145] |
| 178850comp | 5'-CAA AAT TAC AGA AGC TTC AAA TTG TTG T-3' | [SEQ ID NO. 146] |
| 192610comp | 5'-GTA CCT TCA AGT AGC AAG GCT GAC A-3' | [SEQ ID NO. 147] |
| 195088comp | 5'-GTC CCT TTT AAG CAA CCT ACA GGG G-3' | [SEQ ID NO. 148] |
| EPHX2comp | 5'-TTC AGA ACA ATG CTG CCA TCC ATG C-Cy3-3' | [SEQ ID NO. 149] |
| NAT12comp | 5'-AAA TAT ACT TAT TTA CGC TTG AAC CTC-3' | [SEQ ID NO. 150] |
| GSTA1comp | 5'-CTC AAT AGT TCC CTC CCA CTG AAA GAA G-3' | [SEQ ID NO. 151] |
| NAT1Bcomp | 5'-CAA ATA ATA ATA ATA ATA ATA ATA AAT GT-3' | [SEQ ID NO. 152] |
| DTDcomp-Cy3 | 5'-TGC CCA ATG CTA TAT GTC AGT TGA G-Cy3-3' | [SEQ ID NO. 153] |
| EH1comp-Cy3 | 5'-TAC CTT CAA TCT TAG TCT TGA AGT GAG GGT-Cy3-3' | [SEQ ID NO. 154] |
| CYP19comp-Cy3 | 5'-GTG CCT GCA ACT ACT ACA ACC GGG T-Cy3-3' | [SEQ ID NO. 155] |
| 178850comp-Cy3 | 5'-CAA AAT TAC AGA AGC TTC AAA TTG TTG T-Cy3-3' | [SEQ ID NO. 156] |
| 192610comp-Cy3 | 5'-GTA CCT TCA AGT AGC AAG GCT GAC A-Cy3-3' | [SEQ ID NO. 157] |
| 195088comp-Cy3 | 5'-GTC CCT TTT AAG CAA CCT ACA GGG G-Cy3-3' | [SEQ ID NO. 158] |
| EPHX2comp-Cy3 | 5'-TTC AGA ACA ATG CTG CCA TCC ATG C-Cy3-3' | [SEQ ID NO. 159] |
| NAT12comp-Cy3 | 5'-AAA TAT ACT TAT TTA CGC TTG AAC CTC-Cy3-3' | [SEQ ID NO. 160] |
| GSTA1Comp-Cy3 | 5'-CTC AAT AGT TCC CTC CCA CTG AAA GAA G-Cy3-3' | [SEQ ID NO. 161] |
| NAT1Bcom-Cy3 | 5'-CAA ATA ATA ATA ATA ATA ATA ATA AAT GT-Cy3-3' | [SEQ ID NO. 162] |
| DTDcomp-Cy5 | 5'-Cy5-TGC CCA ATG CTA TAT GTC AGT TGA G-3' | [SEC ID NO. 163] |
| EH1comp-Cy5 | 5'-Cy5-TAC CTT CAA TCT TAG TCT TGA AGT GAG GGT-3' | [SEQ ID NO. 164] |
| CYP19comp-Cy5 | 5'-Cy5-GTG CCT GCA ACT ACT ACA ACC GGG T-3' | [SEQ ID NO. 165] |
| 178850comp-Cy5 | 5'Cy5-CAA AAT TAC AGA AGC TTC AAA TTG TTG T-3' | [SEQ ID NO. 166] |
| 192610comp-Cy5 | 5-Cy5-GTA CCT TCA AGT AGC AAG GCT GAC A-3' | [SEQ ID NO. 167] |
| 195088comp-Cy5 | 5'-CyS-GTC CCT TTT AAG CAA CCT ACA GGG G-3' | [SEQ ID NO. 168] |
| EPHX2comp-Cy5 | 5'-CY5-TTC AGA ACA ATG CTG CCA TCC ATG C-3' | [SEQ ID NO. 169] |
| NAT12comp-Cy5 | 5'-Cy5-AAA TAT ACT TAT TTA CGC TTG AAC CTC-3' | [SEQ ID NO. 170] |
| GSTA1Comp-Cy5 | 5'-Cy5-CTC AAT AGT TCC CTC CCA CTG AAA GAA G-3' | [SEQ ID NO. 171] |

Mixture1: DTDcomp, EH1comp-Cy3, CYP19comp-Cy5, 178850comp-Cy3, 192610comp-Cy5, 195088comp-Cy3, EPHX2comp-Cy5, NAT12comp-Cy3, GSTA1comp-Cy5, NAT1 Bcomp-Cy3

Mixture2: DTDcomp-Cy3, EH1comp, CYP19comp-Cy3, 178850comp-Cy5, 192610comp-Cy3, 195088comp-Cy5, EPHX2comp-Cy3, NAT12comp-Cy5, GSTA1comp-Cy3, NAT1 Bcomp-Cy5

Mixture 3: DTDcomp-Cy5, EH1comp-Cy3, CYP19comp, 178850comp-Cy3, 192610comp-Cy5, 195088comp-Cy3, EPHX2comp-Cy5, NAT12comp-Cy3, GSTA1comp-Cy5, NAT1 Bcomp-Cy3

Mixture 4: DTDcomp-Cy3, EH1comp-Cy5, CYP19comp-Cy3, 178850comp, 192610comp-Cy3, 195088comp-Cy5, EPHX2comp-Cy3, NAT12compCy5, GSTA1comp-Cy3, NAT1Bcomp-Cy5

Mixture 5: DTDcomp-Cy5, EH1comp-Cy3, CYP19comp-Cy5, 178850comp-Cy3, 192610comp, 195088comp-Cy3, EPHX2comp-Cy5, NAT12comp-Cy3, GSTA1comp-Cy5, NAT1Bcomp-Cy3

Mixture 6: DTDcompCy3, EH1comp-Cy5, CYPL9comp-Cy3, 178850comp-Cy5, 192610comp-Cy3, 195088comp, EPHX2comp-Cy3, NAT12comp-Cy5, GSTA1 comp-Cy3, NAT1 Bcomp-Cy5

Mixture 7: DTDcomp-Cy5, EH1comp-Cy3, CYP19comp-Cy5, 178850comp-Cy3, 192610comp-Cy5, 195088comp-Cy3, EPHX2comp, NAT12comp-Cy3, GSTA1 comp-Cy5, NAT1 Bcomp-Cy3

Mixture 8: DTDcomp-Cy3, EH1comp-Cy5, CYP19comp-Cy3, 178850comp-Cy5, 192610comp-Cy3, 195088comp-Cy5, EPHX2comp-Cy3, NAT12comp, GSTA1 comp-Cy3, NAT1 Bcomp-Cy5

Mixture 9: DTDcomp-Cy5, EH1comp-Cy3, CYP19comp-Cy5, 178850comp-Cy3, 192610comp-Cy5, 195088comp-Cy3, EPHX2comp-Cy5, NAT12comp-Cy3, GSTA1 comp, NAT1Bcomp-Cy3

Mixture 10: DTDcomp-Cy3, EH1comp-Cy5, CYP19comp-Cy3, 178850comp-Cy5, 192610comp-Cy3, 195088comp-Cy5, EPHX2comp-Cy3, NAT12comp-Cy5, GSTA1comp-Cy3, NAT1 Bcomp The reporter mixtures were addressed actively. All 10 pads of one column representing a set of 10 different DNA captures were addressed in parallel with one reporter mixture. Ten columns were addressed sequentially each with a different reporter mixture. Addressing conditions were 50 mM Histidine, 25 nM for each conjugate, 2.0 V, 180 s. The reporter mixture was heated to 95° C. for 5 min and rapidly chilled on an ice bath immediately prior to addressing in order to disrupt secondary structures and putative DNA—DNA interactions. The sequences of the reporters in the is, mixture were as noted in the above table. The chip was washed with high salt buffer (50 mM phosphate, 500 mM NaCl; pH7.0; 20 steps at 75 µl/s for 3 sec each) to remove unbound reporter oligonucleotides.

Thus, an array of bound reporter oligonucleotides where adjacent reporters are labeled with different fluorescent dyes was produced. On the positions of the diagonal (1,1,; 2,2, . . . 10,10) the reporter was unlabeled.

Step 4: Fluorescent Readout

The chip is imaged at low gain (128 µs) in both Cy3 (red) and Cy5 (green) channel:

Frame 1: GREEN (Cy3 Channel)

| columns | 1 | 2 | 3 | 4 | 5 | 6 | 7 | 8 | 9 | 10 |
|---|---|---|---|---|---|---|---|---|---|---|
| 1 | 31 | 461 | 38 | 484 | 38 | 496 | 40 | 518 | 53 | 585 |
| 2 | 572 | 47 | 529 | 65 | 535 | 66 | 656 | 69 | 783 | 63 |
| 3 | 58 | 267 | 87 | 269 | 98 | 294 | 89 | 298 | 101 | 341 |
| 4 | 553 | 74 | 656 | 84 | 643 | 83 | 658 | 69 | 657 | 65 |
| 5 | 32 | 568 | 55 | 717 | 68 | 727 | 66 | 722 | 77 | 659 |
| 6 | 573 | x | 586 | 72 | 863 | 77 | 859 | 89 | 826 | 81 |
| 7 | 39 | 352 | 62 | 448 | 77 | 500 | 67 | 525 | 72 | 400 |
| 8 | 466 | 75 | 641 | 115 | 722 | 111 | 711 | 88 | 670 | 97 |
| 9 | 58 | 478 | 94 | 576 | 102 | 650 | 107 | 645 | 92 | 582 |
| 10 | 456 | 90 | 455 | 93 | 488 | 99 | 527 | 107 | 559 | 63 |

Note:
Position 6-2 is the reference electrode and not used for addressing

Frame 1: RED (Cy5 Channel)

| columns | 1 | 2 | 3 | 4 | 5 | 6 | 7 | 8 | 9 | 10 |
|---|---|---|---|---|---|---|---|---|---|---|
| 1 | 14 | 15 | 583 | 16 | 467 | 15 | 527 | 15 | 644 | 16 |
| 2 | 14 | 17 | 19 | 606 | 30 | 542 | 28 | 667 | 30 | 720 |
| 3 | 189 | 20 | 21 | 34 | 156 | 36 | 158 | 42 | 177 | 36 |
| 4 | 15 | 414 | 22 | 18 | 18 | 415 | 25 | 448 | 28 | 490 |
| 5 | 336 | 19 | 358 | 18 | 18 | 17 | 458 | 23 | 496 | 23 |
| 6 | 15 | x | 22 | 686 | 22 | 17 | 20 | 723 | 34 | 717 |
| 7 | 356 | 31 | 411 | 38 | 484 | 29 | 22 | 28 | 484 | 34 |
| 8 | 20 | 468 | 41 | 528 | 46 | 542 | 32 | 27 | 26 | 497 |

-continued

| | | | | | Frame 1: RED (Cy5 Channel) | | | | |
|---|---|---|---|---|---|---|---|---|---|
| | | | | | Rows | | | | |
| columns | 1 | 2 | 3 | 4 | 5 | 6 | 7 | 8 | 9 | 10 |
| 9 | 331 | 35 | 411 | 34 | 454 | 38 | 485 | 34 | 23 | 24 |
| 10 | 19 | 388 | 43 | 345 | 47 | 351 | 39 | 403 | 23 | 16 |

Note:
Position 6-2 is the reference electrode and not used for addressing

The fluorescent pattern matches the expected localization of the fluorescence on the array, given the addressing patterns used. This demonstrates that:

1.) although mixtures of conjugates are addressed in parallel, each the DNA capture sequences is immobilized to a specific pad (location) on the array as defined by its p-RNA SBU/SAU recognition
2.) although addressed in parallel, each DNA reporter oligonucleotide is specifically bound by its matching DNA capture.

Example 5.4

Use of Immobilized Nucleic Acids in a SNP Determination

As a demonstration of the practical application of the synthetic binding system-immobilized nucleic acids to various assay formats, a single nucleotide polymorphism (SNP) type experiment was carried out using immobilized pRNA-DNA conjugates on a NanoChip™ device. The SNP discrimination assay format is standard on the device, and this particular variant utilizes base-stacking probes to better distinguish between wild-type and mutant nucleic acids. Instead of PCR amplicons synthetic oligonucleotides were used as targets.

A p-RNA synthetic binding address (H4-102b from Example 2.2) was fixed on four positions of a NanoChip cartridge as described in Experiment 3.1. A capture-stabilizer DNA-p-RNA conjugate was addressed to all four positions. The conjugate was bound to the surface by the specific p-RNA interaction leading to a single stranded DNA capture-stabilizer immobilized on the chip surface. Addressing conditions for the capture were: 50 nM conjugate; 50 mM Histidine; 2.0 V. 120 s. A wild type target sequence was addressed to position #1 of the chip (40 nM DNA, 50 mM Histidine; 2.0 V, 120 s). After washing of unbound material with histidine buffer, a mutant SNP target with a single base mutation was addressed to position #2 of the chip under the same conditions. To position #3 a 1:1 mixture of WT and mutant target was addressed. To position #4 a 1:4 mixture of WT and mutant target is addressed.

The reporting is done by passively hybridizing a mixture of the Cy3 labeled WT reporter and the Cy5 labeled mutant reporter to all positions of the chip (at 500 nM reporter, 50 mM phosphate pH 7.5, 500 mM NaCl). After washing with high salt buffer (50 mM phosphate pH 7.5, 500 mM NaCl) the fluorescence of the four chip positions is measured in the Cy3 and C5 channel. The Cy3 fluorescence is normalized (100% for the WT at position #1) and the Cy5 signal of the mutant SNP target is normalized (100%. at position #2).

The following signals are measured:

| Position | 1 | 2 | 3 | 4 |
|---|---|---|---|---|
| Sample | WT | SNP | WT/SNP 1:1 | WT/SNP 1:4 |
| Cy3 signal (1 = 100) | 100 | 1 | 30 | 7 |
| Cy5 signal (2 = 100) | 1 | 100 | 20 | 63 |

Example 6
Immobilization of Amplified Nucleic Acids

Amplified nucleic acids are immobilized by using conjugates of synthetic binding units and amplified nucleic acids.

```
WT target (synthetic)
5'-ggc gtt ttg caa aca tac ctt caa tct tag tct tga agt gag ggt Gtc tgt tga gaa tct cca    [SEQ ID NO. 180]
cct g-3'

Mutant target (synthetic)
5'-ggc gtt ttg caa aca tac ctt caa tct tag tct tga agt gag ggt Atc tgt tga gaa tct cca    [SEQ ID NO. 181]
cct g-3'

Capture-Stabilizer 3' p-RNA-102a
5'-acc ctc act tca aga cta aga ttg aag gta-3'4'-TCCTGCATTC-2'                              [SEQ ID NO. 182]

WT reporter (5' Cy3)
5'-tct caa cag aC-3'                                                                       [SEQ ID NO 183]

Mutant reporter (5' Cy5)
5'-tct caa cag aT-3'                                                                       [SEQ ID NO 184]
```

One method of obtaining such conjugates Is by using conjugates of SBUs and nucleic acids as primers for enzymatic amplification reactions, as described below. Typical amplification reactions for nucleic acids are the polymerase chain reaction (PCR), or isothermal methods as described by Westin et al. (J. Clinical Microbiol 39 (3) 1097–1104 (2001)). If the primer used in such methods is a conjugate, a conjugate is obtained in which the amplified nucleic acids are linked to an SBU.

Conjugates of this kind are immobilized on support materials by using the conjugates in the addressing protocols described above for capture/stabilizer conjugates: after the amplification reaction, the conjugates are combined, as desired, to form sets in which each SBU occurs only once. The conjugates are desalted (BioRad Bio-Spin columns) and diluted with 50 mM histidine buffer down to a final concentration of 2.5 to 10 nM. The conjugates are directed to the desired locations on a Nanogen instrument according to the protocols of the manufacturer (+2.0 V; 3 minutes). The specific recognition and binding of SBU and SAU immobilizes the conjugates so that, as a result, an array of amplified nucleic acids is obtained. Using this array, it is possible to carry out all experiments and assays which can be carried out using an array prepared via direct immobilization of nucleic acids amplicons on the array positions, such as gene expression and SNP assays.

Example 7

Immobilization of Amplified Nucleic Acids for Gene Expression Studies

The question of the relative frequency of particular nucleic acids, the mRNA of genes, is central to gene expression studies. For this purpose, mRNAs are isolated from it tissues or cells, and specific sections thereof are amplified. mRNA is isolated from tissues, as described in DNA Microarrays—A Practical Approach (Schena, M; Oxford University Press, Oxford, 1999), and particular nucleic acid sequences (genes) are amplified with specific biotinylated primers. If conjugates of nucleic acids and SBUs are used as primers instead, an encoded amplification product is obtained for the appropriate species. The amplification reaction is carried out for each time, stage or population individually according to the protocol stated. Identical gene sequences but from different times, stages or populations, are encoded with different SBUs. When examining a plurality of sequences at the same time, the nucleic acids may be amplified simultaneously according to a multiplex amplification reaction. After amplification, the conjugates are combined into sets such that a) all times, stages or populations of one species, which are to be compared, are gathered in one set (with a different SBU in each case) and that b) each SBU occurs only once in any one set.

An array of attached synthetic address units (SAU) is prepared according to the methods described in Example 3.1 and 3.2 (See FIG. 13B). On this array, the sets are directed to the locations of the SAUs complementary to the SBUs contained in the set by applying a voltage (+2.0 V for 3 min). In this connection, at least those locations which carry SAUs complementary to the SBUs of one gene are addressed simultaneously. As a result, the times, stages or populations of one gene, which are to be compared, may be immobilized under identical conditions. The amplicons bound to the array positions are then detected by hybridization with a labeled nucleic acid complementary to the gene amplicon.

Example 8

Detection of Stability and Selectivity of the Binding of Synthetic Binding Systems in a Multiplex SPR Experiment with 14 Different pRNA Address Unit/Binding Unit Pairs All SPR (surface plasmon resonance) experiments described were carried out in a BIAcore 2000 instrument from BIAcore (Uppsala, Sweden), with BIAcore Control 3.1 software. The sensograms recorded were evaluated and processed using the BIAevaluation 3.1 software. The biotinylated pRNA address units were attached to the surface of BIAcore chips "Sensor Chip SA." Each chip comprises four "channels" (fluidic conduits with the sensor surface) which are available both for immobilization and for detection. The buffer system used was BIAcore standard buffer HBS-EP. Each sensor chip used underwent a cleaning process prior to binding of the address units so that subsequently a constant baseline was obtained on all four channels.

In order to clean the Sensor Chip for optimal use in the experiments, a protocol was developed comprising the following steps:

1. 10 min washing with HBS-EP buffer (5 µl/min)
2. 1 min injection of 10 mM NaOH (5 µl/min)
3. 5 min washing with HBS-EP buffer (5 µl/min)
4. repeating twice steps 1–3

Immobilization of the pRNA Synthetic Address Units:

Biotinylated pRNA address units with "s" sequences with a 4' biotin (produced as in Example 2.1) were fixed to the Sensor Chip surface using protocols provided by the manufacturer of the instrument. Each channel (position on the BIAcore chip) is thus provided with a defined address unit. In order to ensure this, the attachment step had to be carried out successively for the 4 channels. The binding efficiency of the surface was improved by dissolving the address units separately in 500 mM NaCl HBS-EP (instead of Standard BIAcore buffer s50 mM NaCl HBS-EP). The concentration of the synthetic address units was always 100 nM.

Each channel was prepared at 295 K for two minutes at a flow rate of 5 µl/min so that after immobilization approximately 700–800 RU (resonance units) of substance were bound. After binding, each channel was washed with HBS-EP standard buffer for a further 10 min. Thus it was possible to bind four different address un its per chip. In order to assay 14 different address units, therefore 4 chips had to be used (3 chips with 4 address units and 1 chip with 2 address units). Each chip was always treated with identical protocols and buffer solutions.

Binding of Complementary Binding Units to the Surfaces:

A complementary synthetic bin ding unit was inject ed in to all four channels of a Sensor Chip so that it was possible, using one injection of substrate, to test directly four synthetic address units for their affinities to the binding unit. Binding of the complementary binding units was studied in 150 mM NaCl HBS-EP buffer at a flow rate of 30 µl/min at 295 K and an injection time of 2 min. The concentration of the 14 complementary binding units was always 300 nM: the solutions were prepared separately. After each injection, a washing step of 20 min followed in order to be able to estimate the strength of binding/affinity of the binding addresses. After binding of the individual conjugates was tested, the conjugates were stripped off by disrupting the SAU/SBU interaction with 15 mM NaOH. Subsequently, the chip was ready for another injection, i.e. the surface of the support material was regenerated and was available for further assays. The protocol was carried out 14 times on one chip in order to study each synthetic address unit for affinity to the synthetic binding units. For all 4 chips, therefore, the protocol had to be run 64 times.

Binding protocol of a Sensor Chip on 4 channels:

1. 2 min injection of complementary binding unit×(30 µl/min)*
2. 20 min washing with HBS-EP buffer (30 µl/min)
3. 1 min injection of 10 mM NaOH (5 µl/min)
4. 5 min washing with HBS-EP buffer (5 µl/min)
5. 1 min injection of 10 mM NaOH (5 µl/min)

6. 20 min washing with HBS-EP buffer (30 µl/min)
7. repeating 13×steps 1–6

The names of the synthetic binding unit and synthetic address units studied for their affinity and specificity are indicated in FIG. 14. The number denotes the name of the binding systems; 'b' in this experiment was the synthetic address unit fixed to the surface of the Sensor Chip; 'a' in this experiment was the synthetic binding unit whose binding to the address unit was shown. The synthetic address units were synthesized and purified as pRNA according to the methods described in Example 2.1.

The result of the SPR binding study is depicted in FIG. 14. The diagonal clearly indicates the specific binding of the synthetic binding systems. Note that off of the diagonal, most of the SBUs do not interact with non-corresponding SAUs, or do so to an extend that is much less than their interaction with their corresponding SAU. These sequences are "orthogonal" to each other. Off of the diagonal, unwanted interactions appear at a few positions, for example the 118 and 119 pairs. These two SBS sequences are only slightly orthogonal to each other. Combinations of synthetic address units and synthetic binding units showing such cross-reactions can be avoided if required for a particular experiment or for the construction of a particular array.

Example 9

Use of pRNA-DNA Conjugates as Primers in a PCR Reaction

For the PCR reaction a set of two different pRNA-DNA conjugates was used (set 1 and set 2) which serve as primers during the amplification reaction. The preparation of the primers by solid-phase synthesis is described in Example 1.1. With the aid of these novel primers, a defined sequence section from the gene of the α-fetoprotein from *Mus musculus* was amplified and isolated. The cDNA of the gene was used here for amplification. The primer constructs had the following sequences:

Set1:

Feto1-102a (rev. 1977–1953);

$^4$TCCTGCATTC$^{2'5'}$AGA AAT CTC ACA TGG ACA TCT TCA$^{3'}$[SEQ ID NO. 172]

Feto1 (for.; 1796–1820): 5'-G TCT GTT TCA CAG AAG AGG GTC CAA-3' [SEQ ID NO.173]

Set2:

Feto2-102a (for 1796–1820):

$^4$TCCTGCATTC $^{2'5'}$CCT GGG CTT TGC AGC ACT TCT C$^{3'}$ [SEQ ID NO. 174]

Feto2 (for.; 1634–1659): 5'-GA TCT GTG CCA AGC TCA GGG CAA AG-3' [SEQ ID NO. 175]

The sequence of the α-fetoprotein gene cDNA, from which the sequences were amplified, is:

Mouse mRNA encoding alpha-fetoprotein (a fetal serum protein): tcccacttcc agcactgcct gcggtgaagg aacaageagc cat-gaagtgg atcacacccg cttccctcat cctcctgcta catttcgctg cgtc-caaagc attgeacgaa aatgagtttg ggatagcttc cacgttagat tcctc-ccagt gcgtgacgga gaagaatgtg cttageatag ctaccatcac ctttacccag tttgttccgg aagccaccga ggaggaagtg aacaaaatga ctagcgatgt gttggctgca algaagaaaa actctggcga tgggtgttta gaaagccage tatctgtgtt tctggatgaa atttgccatg agacggaact ctctaacaag tatggactct caggctgctg cagccaaagt ggagtggaaa gacatcagtg tctgctggca cgcaagaaga ctgctccggc ctctgtccea cccttceagt ttccagaacc tgccgagagt tgcaaagcac atgaagaaaa cagggcagtg ttcatgaaca ggttcatcta tgaagtgtca aggaggaacc cct-tcatgta tgccccagcc attctgtcct tggctgctca gtacgacaag gtcgt- tctgg catgctgcaa agctgacaac aaggaggagt gcttccagac aaa-gagagca tccattgcaa aggaattaag agaaggaagc atgttaaatg agcatgtatg ttcagtgata agaaaatttg gatccegaaa cctccaggca acaaccatta ttaagctaag tcaaaagtta actgaagcaa attttactga gat-tcagaag ctggccctgg atgtggctca catccacgag gagtgttgcc aag-gaaactc gctggagtgt ctgcaggatg gggaaaaagt catgacatat atatgt-tctc aacaaaatat tctgtcaagc aaaatagcag agtgctgcaa attacccatg atccaactag gcttctgcat aattcacgca gagaatggcg tcaaacctga aggcttatct ctaaatccaa gccagttntt gggagacaga aatnttgccc aatttttcttc agaggaaaaa atcatgttca tggcaagcn tcttcatgaa tactcaa-gaa ctcacccccaa ccttcctgtc tcagtcattc taagaattgc taaaacgtac caggaaatat tggagaagtg ttcccagtct ggaaatctac ctggatgtea gga-caatctg gaagaagaat tgcagaaaca catcgaggag agccaggcac tgtc-caagca aagctgcgct ctctaccaga ccttaggaga ctacaaatta caaaatctgt tccttattgg ttacacgagg aaagcccctc agctgacctc agca-gagctg atcgacctca ccgggaagat ggtgagcatt gcctccacgt gctgc-cagct cagcgaggag aaatggtccg gctgtggtga gggaatggcc gacattttca ttggacattt gtgtataagg aatgaagcaa gccctgtgaa ctctg-gtatc agceactgct gcaactcttc gtattccaac aggaggctat gcatcaccag tttctgagg gatgaaacct atgccccctcc cccauctct gaggataaat tcatct-tcca caaggatctg tgccaagctc agggcaaage cetacagacc atgaaa-caag agcttctcat taacctggtg aagcaaaagc ctgaactgac agaggag-cag ctggcggctg tcactgcaga tttctcgggc cttttggaga agtgctgcaa agcccaggac caggaagtct gtttcacapa aizaigzcca aa-ttgattt ccaaaactcp tgatpctttg gQgcnaaa catctccaea azgaagage gacaaaaaaa togilgacg ctttgipg agcctttttgg cttaactgta act-gctagla ctttaaccac atgztgaaga tgtccatztg agatttctat accttaggaa taaaaacttt tcaactatt

[SEQ ID NO. 176]

The amplified gene fragment to be expected using primer set 1 is underlined in the sequence.

Amplification Protocol:

For the amplification, 4 µl of a dNTP mix (2.5 mM; Promega), 2.5 µl of Feto1-102a (rev.) (10 µM), 2.5 µl of Feto1 (for.) (10 µM), 1 µl of taq-polymerase (5 U/µl; Promega) and 2 µl of isolated cDNA from *Mus musculus* were added to 30 µl of DEPC water (Ambion) 5 µl of 10× thermophilic DNA-polybuffer (Promega), 3 µl of MgCl$_2$ (25 mM; Promega). For the PCR reaction, the 50 µl mixture was subjected to the following amplification cycle: pre-incubation at 95° C. for 2 min; 35-cycle PCR at 94° C. (15 sec), 55° C. (30 sec), 72° C. (30 sec) and finally 72° C. (7 min). After completion of the amplification, the reaction mixture was removed and stored at 4° C.

The amplification was carried out for different stages of expression of the α-fetoprotein gene using primer sets 1 and 2. Thus, the expression of the murine α-fetoprotein gene in murine fetal liver was determined for day 8 and day 14 developmental stages using the novel primers. As a control, a parallel reaction was performed using standard DNA primers, and analyzed on an agarose gel (see FIG. 22) for comparison. For analysis of the gene expression, a sample (20 µl) was removed from the PCR mixture, mixed with 2 µl of 6× loading buffer (Sigma) and the bands were separated on a 1.7% agarose gel.

As shown in FIG. 22, in Feto 1 and Feto 2 specific amplification products of the gene are formed using the conjugate primers whenever the products are also obtained an with DNA primers. Conversely, the conjugate primers produce no product whenever the DNA primers produce no product (e.g., Feto 2 d8), showing that non-specific amplification is not occurring. The dilution series of Feto 1-102a (rev.), in which the conjugate primer was used at decreasing concentrations, shows that primer dimers do not appear if relatively low amounts of the primer are used.

In addition, the SBU conjugate products of the PCR reaction were able to be immobilized by SBUs on a NanoChip™, in a procedure analogous to that in Example 4.

Example 10

Use of the pRNA-DNA Conjugates in Midi-Scale PCR (500 µl Reaction)

For particular applications larger amounts of encoded amplified nucleic acids are required. The following example describes the use of the pRNA-DNA conjugate for primer amplification of a fragment of the murine α-fetoprotein gene from a cDNA library in a relatively large PCR mixture (500 µl). Using identical primer sets, as described in Example 9, the following amplification protocol was applied.

For the amplification 4 µl of a dNTP mix (2.5 mM; Promega), 25 µl of Feto1-102a (rev.) (10 µM), 25 µl of Feto1 (for.) (10 µM), 10 µl of taq-polymerase (5 U/µl; Promega) and 20 µl of cDNA library from *Mus musculus* were added to 336 µl of DEPC water (Ambion) 50 µl of 10× thermophilic DNA-polybuffer (Promega), 30 µl of MgCl$_2$ (25 mM; Promega). For the PCR reaction, the 500 µl mixture was subjected to the following amplification cycle: pre-incubation at 95° C. for 2 min; 35-cycle PCR at 94° C. (15 sec), 55° C. (30 sec), 72° C. (30 sec) and finally 72° C. (7 min). After completion of the amplification, the reaction mixture was removed and stored at 4° C.

Analogously to Example 9, an agarose gel electrophoresis was carried out for the fractionation. The result is depicted in FIG. 22B. The gene fragments obtained were purified with the aid of the Quiagen purification kit and subsequently sequenced. The amplification of the desired sequence was confirmed.

Example 11

Ligation of a Conjugate with a Nucleic Acid by Means of T4 RNA Ligase

The enzymatic coupling between 5'-phosphate-(3'-O-methyl-RNA)-pRNA hybrid molecules (donor) and RNA (acceptor) by means of T4 RNA ligase is described below. For background on ligation reactions, see England, T. E.; Nature, 275, 560–561 (1978) or England, T. E.; Bruce, A. G.; Uhlenbeck, O. C. Methods in Enzymology 65(1), 65–74 (1980) or Romaniuk, Paul J.; Uhlenbeck, Olke C. Methods Enzymol. 100, 52–9 (1983)). In this reaction, a phosphodiester bond between the 5' phosphate of the RNA-pRNA hybrid molecule and the 3' OH group of an acceptor RNA is formed. The acceptor RNA used was prepared by in-vitro transcription according from a DNA template, using a 5' T7 promoter and T7 RNA polymerase.

Preparation of an in-vitro transcription template (for generating an acceptor RNA) by PCR using the following primers:

Oligonucleotide #1, Primer forward: 5'-TAATACGACTCACTATAGGG-3' [SEQ ID NO. 177]

Oligonucleotide #2, primer reverse: 5'-TGGGGCTAAGCGGGATCG-3-[SEQ ID NO. 178]

Oligonucleotide #3, template: 5'-GCTGCAGTAA-TACGACTCACTATAGGGGCTATAGCTCAGCTG-GGAGAGCGCTTGCCTGGGMGCAAGAGGTCAG-CGGTTCGATCCCGCTTAGCCCCACCGCGGCGT-CCATCCA-3' [SEQ ID NO. 179]

A PCR reaction mixture consisting of 1 µM primer forward (oligonucleotide #1), 1 µM primer reverse (oligonucleotide #2), 0.2 µM template (oligonucleotide #3), 2 mM MgCl$_2$, 50 mM KCl, 10 mM Tris/HCl (pH 9.0 at 25° C.), 0.1% (v/v) TritonX-100, 0.2 mM dNTP, 0.05 U/µl Taq polymerase (Promega) was used for a PCR amplification over 20 cycles according to the following temperature program:

| | | |
|---|---|---|
| 60 sec | 95° C. | |
| 30 sec | 95° C. | |
| 30 sec | 53° C. | } 20 cycles |
| 60 sec | 72° C. | |
| 120 sec | 72° C. | |

The acceptor RNA was then prepared by in-vitro transcription from the template. The unpurified PCR product was used as DNA template to an in-vitro transcription kit (Promega Ribomax™ largescale RNA production system T7). The in-vitro transcription mixture was incubated at 37° C. for 2–6 h. Subsequently, the transcription products were purified either by a preparative urea gel or by an RNeasy™ purification column (Qiagen). The success of the transcription reaction was monitored by fractionating the transcription products on a 10% polyacrylamide urea gel.

Enzymatic Linkage Between RNA-pRNA Hybrid Molecules and Acceptor RNA by Means of T4 RNA Ligase:

For ligating a 5'-phosphate-(3'-O-methyl-RNA)-pRNA-hybrid molecule (donor) with the acceptor RNA, 100 pmol of purified acceptor RNA were incubated together with 300 pmol or 1000 pmol of a 5'-phosphate-(3'-O-methyl-RNA)-pRNA-hybrid molecule (Described in Example 1.2) and 10 U T4 RNA ligase (MBI fermentas), 50 mM HEPES/NaOH (pH 8.0 at 25° C.), 10 mM MgCl$_2$, 10 mM DTT, 1 mM ATP, 20 µg/ml BSA and 10% (v/v) DMSO in a final reaction volume of 15 µl at 16° C. for 30 min.

To check the success of the ligation, an equal volume of a loading buffer (8.3 M urea, 50 mM EDTA) was added to the mixtures which, after heat denaturation (5 min at 80° C.), were fractionated on a 10% polyacrylamide urea gel (40 mA for approx. 20 min). The nucleic acids were then visualized in the gel by UV shadowing (FIG. 23A). In addition, it was possible to detect the particular ligation product in the gel by means of fluorescence scanning, owing to labeling the (3'-O-methyl-RNA)$_p$RNA half of the molecule with the fluorescence dye Cy3 (FIG. 23B). Since the acceptor RNA contains no dye, the RNA is not detectable in the fluorescence image. Due to its short length, the free pRNA conjugate also does not appear in the fluorescence image.

Example 12

Use of SBU-NA Conjugates as Primers in Anchored SDA Reactions

SDA forward and reverse primers (each containing a BsoBI endonuclease recognition sequence 5' of a sequence which is specific for a target nucleic acid) may be attached to SBUs by the methods described in Example 1. These are then electronically address to individual locations on the microchip array. Single or multiple SAU/SBU pairs can be employed at any one location, for the amplification of a single product, or multiplex amplification. An exemplary target for amplification would be the α-fetoprotein of *Mus musculus* described above, for which the above primer sequences, may be utilized with the addition of a BsoBI recognition site sequence (CIYCGRG). Template DNA from a sample is then electronically addressed and hybridized to the immobilized primers.

The amplification reaction is initiated by the addition of enzymes and bumper primers (Which hybridize 5' to the SDA primers on each strand of the target nucleic acid.) The chip is warmed to 60° C. for 5 min. 10 µL of a pre-warmed SDA mixture (6 mM morpholinopropane sulfonic acid

[MOPS]., pH 7.8; 1.7 mM [each] dGTP, dTTP, dATP, and thiolated dCTP; 85 mM KCl, 18 mM $MgCl_2$; 23 mM NaCl; 3.5 mM Tris-HCl, pH 7.9; 35 µM dithiothreitol; 1.5 U BsoBI; 0.8 U BstI polymerase; and 25 nM each bumper primer) is introduced to the chip. Following incubation for 30 min. at 60° C., the amplification reaction is stopped by washing the chip 5 times with 37.5 mM NaCl, 3.75 mM sodium citrate, pH 7.2. The anchored amplicons are denatured with alkaline solution (75 mM NaCl, 7 mM sodium citrate, pH 12.5) for 4 min and washed 5 times with 37.5 mM NaCl, 3.75 mM sodium citrate, pH 7.2, to removed non-anchored complementary amplicons. The anchored amplicons are subsequently detected via the hybridization with the appropriate reporter probe.

We claim:

1. A method for enzymatically modifying a conjugate comprising the steps of:
providing a conjugate comprising a nucleic acid and a synthetic binding unit, wherein the synthetic binding unit is selected from the group consisting of pRNA, pDNA, and CNA; and
contacting the conjugate with at least one enzyme to effect modification of the nucleic acid,
wherein when the synthetic binding unit is pRNA or pDNA, the synthetic binding unit and the nucleic acid are connected via a linkage selected from the group consisting of the 2' end of the synthetic binding unit to the 5' end of the nucleic acid, 2' end of the synthetic binding unit to the 3' end of the nucleic acid, 4' end of the synthetic binding unit to the 5' end of the nucleic acid, and 4' end of the synthetic binding unit to the 3' end of the nucleic acid.

2. The method of claim 1, further comprising contacting the conjugate and at least one enzyme with other reagents, wherein the other reagents include a nucleic acid which hybridizes to the nucleic acid of the conjugate.

3. The method of claim 1, further comprising contacting the conjugate and at least one enzyme with other reagents, wherein the other reagents include nucleoside triphosphates or modified nucleoside triphosphates.

4. The method of claim 1, wherein the at least one enzyme is selected from the group consisting of a polymerase, a ligase, an endonuclease, an exonuclease, a kinase, a methyltransferase, a methyl ase, a restriction endonuclease, and a terminal transferase.

5. The method of claim 1, wherein the at least one enzyme is a ligase, and the nucleic acid of the conjugate is modified by ligation of a terminus of the nucleic acid to at least one additional nucleic acid.

6. The method of claim 5, wherein the ligation is template-dependent, and wherein the nucleic acid of the conjugate and the at least one additional nucleic acid are hybridized to adjacent sequences of a template nucleic acid.

7. The method of claim 5, wherein the ligation is template-independent, and wherein the nucleic acid of the conjugate and the at least one additional nucleic acid are single stranded.

8. The method of claim 7, wherein the ligase used is a T4 RNA ligase.

9. The method of claim 5, wherein the ligation is a blunt-end, and wherein the nucleic acid of the conjugate and the at least one additional nucleic acid are double stranded.

10. The method of claim 1, further comprising contacting the conjugate and at least one enzyme with other reagents, wherein the at least one enzyme is a polymerase, wherein the nucleic acid of the conjugate has an unblocked 3' terminus, wherein the other reagents comprise a template nucleic acid to which the unblocked 3' terminus of the nucleic acid hybridizes, and wherein the nucleic acid is modified by the addition of at least one nucleoside complementary to the template nucleic acid to the 3' terminus of the nucleic acid.

11. The method of claim 10, further comprising the step of adding a dideoxynucleotide to the nucleic acid of the conjugate.

12. The method of claim 10, further comprising the step of adding a labeled nucleotide to the nucleic acid of the conjugate.

13. The method of claim 10 wherein the template nucleic acid is derived from a biological sample.

14. The method of claim 13 wherein the biological sample is derived from a sample selected from the group consisting of human materials, animal materials, plant materials, fungal materials, cell cultures, viral cultures, food samples, and water samples.

15. The method of claim 10 wherein the polymerase is at least one enzyme selected from the group consisting of DNA polymerases, RNA polymerases, and reverse transcriptases.

16. The method of claim 10 wherein at least a portion of the template nucleic acid sequence is amplified.

17. The method of claim 10, wherein the polymerase is a thermostable polymerase, and wherein the step of contacting the conjugate with at least one enzyme comprise thermocycling the conjugate and the at least one enzyme to alternately i) dissociate extension products from the template nucleic acid and ii) allow the hybridization of conjugate nucleic acid to the template and enzymatic extension of the nucleic acid of the conjugate, wherein at least a portion of the template nucleic acid sequence is amplified.

18. The method of claim 10, further comprising contacting the conjugate with a restriction endonuclease, wherein the nucleic acid of the conjugate comprises an endonuclease recognition sequence 5' of the 3' terminus which hybridizes to the template nucleic acid, and wherein at least a portion of the template nucleic acid sequence is amplified by strand displacement amplification.

19. The method of claim 10, wherein the polymerase is a mixture of an RNA polymerase and a reverse transcriptase, further comprising contacting the conjugate with a RNAase H enzyme, wherein at least a portion of the template nucleic acid sequence is amplified by transcription mediated amplification.

20. The method of claim 1, wherein the enzyme is a terminal transferase, and the nucleic acid of the conjugate is modified by addition of at least one nucleoside to the 3' terminus of the nucleic acid.

21. The method of claim 20, further comprising the step of adding a labeled nucleoside to the nucleic acid of the conjugate.

22. The method of claim 20, wherein a homopolymeric tail is added to the nucleic acid of the conjugate.

23. The method of claim 1, further comprising contacting the conjugate and at least one enzyme with other reagents, wherein the at least one enzyme is a restriction endonuclease, wherein the other reagents comprise a target nucleic acid to which at least a portion of the nucleic acid of the conjugate hybridizes, and wherein the nucleic acid of the conjugate and the target nucleic acid are cleaved by the restriction endonuclease.

24. The method of claim 1, further comprising contacting the conjugate and at least one enzyme with other reagents, wherein the at least one enzyme is a restriction endonuclease, wherein the other reagents comprise a target nucleic acid to which at least a portion of the nucleic acid of the conjugate hybridizes, and wherein the nucleic acid of the conjugate but not the target nucleic acid is cleaved by the restriction endonuclease.

25. The method of claim 1, further comprising contacting the conjugate and at least one enzyme with other reagents, wherein the at least one enzyme is a restriction endonuclease, wherein the other reagents comprise a target nucleic acid to which at least a portion of the nucleic acid of the conjugate hybridizes, and wherein the target nucleic acid but not the nucleic acid of the conjugate is cleaved by the restriction endonuclease.

26. The method of claim 1, further comprising contacting the conjugate and at least one enzyme with other reagents, wherein the enzyme is a RNAse H, wherein the other reagents comprise an RNA target nucleic acid to which at least a portion of the nucleic acid of the conjugate hybridizes, and wherein the target RNA nucleic acid hybridizing to the nucleic acid of the conjugate is degraded by the RNAse.

27. The method of claim 1, wherein the nucleic acid and the synthetic binding unit are joined at an attachment point, wherein the enzymatic modification is within 30 nucleotides of the attachment point.

28. The method of claim 1, wherein the nucleic acid and the synthetic binding unit are joined at an attachment point, wherein the enzymatic modification is within 20 nucleotides of the attachment point.

29. The method of claim 1, wherein the nucleic acid and the synthetic binding unit are joined at an attachment point, wherein the enzymatic modification is within 15 nucleotides of the attachment point.

30. The method of claim 1, wherein the nucleic acid and the synthetic binding unit are joined at an attachment point, wherein the enzymatic modification is within 10 nucleotides of the attachment point.

31. The method of claim 1, wherein the nucleic acid and the synthetic binding unit are joined at an attachment point, wherein the enzymatic modification is within 7 nucleotides of the attachment point.

32. The method of claim 1, wherein the nucleic acid and the synthetic binding unit are joined at an attachment point, wherein the enzymatic modification is within 5 nucleotides of the attachment point.

33. The method of claim 1, wherein the nucleic acid and the synthetic binding unit are joined at an attachment point, wherein the enzymatic modification is within 2 nucleotides of the attachment point.

34. The method of claim 1, wherein the nucleic acid and the synthetic binding unit are joined at an attachment point, wherein the enzymatic modification is the nucleotide at the attachment point.

35. The method of claim 1, wherein the nucleic acid is selected from the group consisting of deoxyribonucleic acids, ribonucleic acids, and chemically modified nucleic acids.

36. The method of claim 1, wherein the nucleic acid is selected from the group consisting of phosphorothioate nucleic acids, phosphorodithioate nucleic acids, methylphosphonate nucleic acids, 2'-O-methyl RNA, and 2'-fluoro RNA.

37. The method of claim 1, wherein the nucleic acid is selected from the group consisting of peptide nucleic acids (PNA) and locked nucleic acids (LNA).

38. The method of claim 1, wherein the nucleic acid is selected from the group consisting of an aptamer and an aptazyme.

39. The method of claim 1, wherein the conjugate further comprises at least one labeling moiety.

40. The method of claim 39, wherein the at least one labeling moiety is selected from the group consisting of fluorescent moieties, quencher moieties, visible dye moieties, radioactive moieties, chemiluminescent moieties, biotin moieties, hapten moieties, micro-particles, paramagnetic micro-particles, and enzymatic labeling moieties.

41. The method of claim 39, wherein the labeling moiety is a fluorescent dye moiety selected from the group consisting of: boron dipyrromethane difluoride dyes, cyanine dyes, fluorescein dyes, rhodamine dyes, phycoerythrin dyes, coumarin dyes, Texas Red dyes, green dyes, FAM, HEX, TET, TAMRA, ROX, EDANA, 4-Acetamido-4'-isothiocyanato-stilbene-2,2'-disulfonic acid, 4,4'-Diisothiocyanatostilbene-2,2'-disulfonic acid, Succinimidyl pyrene butyrate, Acridine isothiocyanate, Cascade Blue, Oregon Green, Lucifer Yellow vinyl sulfone, and IR1446.

42. The method of claim 39, wherein the labeling moiety is a quencher moiety selected from the group consisting of DABCYL, Reactive Red 4 (Cibacron Brilliant Red 3B-A), Malachite Green, 4-Dimethylaminophenylazophenyl-4'-isothiocyanate (DABITC), and 4,4'-Diisothiocyanatodlhydro-stilbene-2,2'-disulfonic acid moieties.

43. A method for enzymatically modifying a conjugate comprising the steps of:
providing a conjugate comprising a nucleic acid and a synthetic binding unit, wherein the synthetic binding unit is selected from the group consisting of pRNA, pDNA, and CNA, and wherein the nucleic acid and the synthetic binding unit are joined at a single attachment point; and
contacting the conjugate with at least one enzyme to effect modification of the nucleic acid, wherein when the synthetic binding unit is pRNA or pDNA, the synthetic binding unit and the nucleic acid are connected via a linkage selected from the group consisting of the 2' end of the synthetic binding unit to the 5' end of the nucleic acid, 2' end of the synthetic binding unit to the 3' end of the nucleic acid, 4' end of the synthetic binding unit to the 5' end of the nucleic acid, and 4' end of the synthetic binding unit to the 3' end of the nucleic acid.

44. The method of claim 43, further comprising contacting the conjugate and at least one enzyme with other reagents, wherein the other reagents include a nucleic acid which hybridizes to the nucleic acid of the conjugate.

45. The method of claim 43, further comprising contacting the conjugate and at least one enzyme with other reagents, wherein the other reagents include nucleoside triphosphates or modified nucleoside triphosphates.

46. The method of claim 43, wherein the at least one enzyme is selected from the group consisting of a polymerase, a ligase, an endonuclease, an exonuclease, a kinase, a methyltransferase, a methylase, a restriction endonuclease, and a terminal transferase.

47. The method of claim 43, wherein the at least one enzyme is a ligase, and the nucleic acid of the conjugate is modified by ligation of a terminus of the nucleic acid to at least one additional nucleic acid.

48. The method of claim 47, wherein the ligation is template-dependent, and wherein the nucleic acid of the conjugate and the at least one additional nucleic acid are hybridized to adjacent sequences of a template nucleic acid.

49. The method of claim 47, wherein the ligation is template-independent, and wherein the nucleic acid of the conjugate and the at least one additional nucleic acid are single stranded.

50. The method of claim 49, wherein the ligase used is a T4 RNA ligase.

51. The method of claim 49, wherein the ligation is a blunt-end, and wherein the nucleic acid of the conjugate and the at least one additional nucleic acid are double stranded.

52. The method of claim 43, further comprising contacting the conjugate and at least one enzyme with other reagents, wherein the at least one enzyme is a polymerase, wherein the nucleic acid of the conjugate has an unblocked 3' terminus, wherein the other reagents comprise a template nucleic acid to which the unblocked 3' terminus of the nucleic acid hybridizes, and wherein the nucleic acid is modified by the addition of at least one nucleoside complementary to the template nucleic acid to the 3' terminus of the nucleic acid.

53. The method of claim 52, further comprising the step of adding a dideoxynucleotide to the nucleic acid of the conjugate.

54. The method of claim 52, further comprising the step of adding a labeled nucleotide to the nucleic acid of the conjugate.

55. The method of claim 52, wherein the template nucleic acid is derived from a biological sample.

56. The method of claim 55, wherein the biological sample is derived from a sample selected from the group consisting of human materials, animal materials, plant materials, fungal materials, cell cultures, viral cultures, food samples, and water samples.

57. The method of claim 52, wherein the polymerase is at least one enzyme selected from the group consisting of DNA polymerases, RNA polymerases, and reverse transcriptases.

58. The method of claim 52, wherein at least a portion of the template nucleic acid sequence is amplified.

59. The method of claim 52, wherein the polymerase is a thermostable polymerase, and wherein the step of contacting the conjugate with at least one enzyme comprise thermocycling the conjugate and the at least one enzyme to alternately i) dissociate extension products from the template nucleic acid and ii) allow the hybridization of conjugate nucleic acid to the template and enzymatic extension of the nucleic acid of the conjugate, wherein at least a portion of the template nucleic acid sequence is amplified.

60. The method of claim 52, further comprising contacting the conjugate with a restriction endonuclease, wherein the nucleic acid of the conjugate comprises an endonuclease recognition sequence 5' of the 3' terminus which hybridizes to the template nucleic acid, and wherein at least a portion of the template nucleic acid sequence is amplified by strand displacement amplification.

61. The method of claim 52, wherein the polymerase is a mixture of an RNA polymerase and a reverse transcriptase, further comprising contacting the conjugate with a RNAase H enzyme, wherein at least a portion of the template nucleic acid sequence is amplified by transcription mediated amplification.

62. The method of claim 43, wherein the enzyme is a terminal transferase, and the nucleic acid of the conjugate is modified by addition of at least one nucleoside to the 3' terminus of the nucleic acid.

63. The method of claim 62, further comprising the step of adding a labeled nucleoside to the nucleic acid of the conjugate.

64. The method of claim 62, wherein a homopolymeric tail is added to the nucleic acid of the conjugate.

65. The method of claim 43, further comprising contacting the conjugate and at least one enzyme with other reagents, wherein the at least one enzyme is a restriction endonuclease, wherein the other reagents comprise a target nucleic acid to which at least a portion of the nucleic acid of the conjugate hybridizes, and wherein the nucleic acid of the conjugate and the target nucleic acid are cleaved by the restriction endonuclease.

66. The method of claim 43, further comprising contacting the conjugate and at least one enzyme with other reagents, wherein the at least one enzyme is a restriction endonuclease, wherein the other reagents comprise a target nucleic acid to which at least a portion of the nucleic acid of the conjugate hybridizes, and wherein the nucleic acid of the conjugate but not the target nucleic acid is cleaved by the restriction endonuclease.

67. The method of claim 43, further comprising contacting the conjugate and at least one enzyme with other reagents, wherein the at least one enzyme is a restriction endonuclease, wherein the other reagents comprise a target nucleic acid to which at least a portion of the nucleic acid of the conjugate hybridizes, and wherein the target nucleic acid but not the nucleic acid of the conjugate is cleaved by the restriction endonuclease.

68. The method of claim 43, further comprising contacting the conjugate and at least one enzyme with other reagents, wherein the enzyme is a RNAse H, wherein the other reagents comprise an RNA target nucleic acid to which at least a portion of the nucleic acid of the conjugate hybridizes, and wherein the target RNA nucleic acid hybridizing to the nucleic acid of the conjugate is degraded by the RNAse H.

69. The method of claim 43, wherein the enzymatic modification is within 30 nucleotides of the attachment point.

70. The method of claim 43, wherein the enzymatic modification is within 20 nucleotides of the single attachment point.

71. The method of claim 43, wherein the enzymatic modification is within 15 nucleotides of the single attachment point.

72. The method of claim 43, wherein the enzymatic modification is within 10 nucleotides of the single attachment point.

73. The method of claim 43, wherein the enzymatic modification is within 7 nucleotides of the single attachment point.

74. The method of claim 43, wherein the enzymatic modification is within 5 nucleotides of the single attachment point.

75. The method of claim 43, wherein the enzymatic modification is within 2 nucleotides of the single attachment point.

76. The method of claim 43, wherein the enzymatic modification is the nucleotide at the single attachment point.

77. The method of claim 43, wherein the nucleic acid is selected from the group consisting of deoxyribonucleic acids, ribonucleic acids, and chemically modified nucleic acids.

78. The method of claim 43, wherein the nucleic acid is selected from the group consisting of phosphorothioate nucleic acids, phosphorodithioate nucleic acids, methylphosphonate nucleic acids, 2'-O-methyl RNA, and 2'-fluoro RNA.

79. The method of claim 43, wherein the nucleic acid is selected from the group consisting of peptide nucleic acids (PNA) and locked nucleic acids (LNA).

80. The method of claim 43, wherein the nucleic acid is selected from the group consisting of an aptamer and an aptazyme.

81. The method of claim 43, wherein the conjugate further comprises at least one labeling moiety.

82. The method of claim 81, wherein the at least one labeling moiety is selected from the group consisting of fluorescent moieties, quencher moieties, visible dye moieties, radioactive moieties, chemiluminescent moieties, biotin moieties, hapten moieties, micro-particles, paramagnetic micro-particles, and enzymatic labeling moieties.

83. The method of claim 81, wherein the labeling moiety is a fluorescent dye moiety selected from the group consisting of: boron dipyrromethane difluoride dyes, cyanine dyes, fluorescein dyes, rhodamine dyes, phycoerythrin dyes, coumarin dyes, Texas Red dyes, green dyes, FAM, HEX, TET, TAMRA, ROX, EDANA, 4-Acetamido-4'-isothiocyanato stilbene-2,2'-disulfonic acid, 4,4'-Diisothiocyanatostilbene-2,2'-disulfonic acid, Succinimidyl pyrene butyrate, Acridine isothiocyanate, Cascade Blue, Oregon Green, Lucifer Yellow vinyl sulfone, and IR1446.

84. The method of claim 81, wherein the labeling moiety is a quencher moiety selected from the group consisting of DABCYL, Reactive Red 4 (Cibacron Brilliant Red 3B-A), Malachite Green, 4-Dimethylaminophenylazophenyl-4'-isothiocyanate (DABITC), and 4,4'-Diisothiocyanatodihydro-stilbene-2,2'-disulfonic acid moieties.

* * * * *

UNITED STATES PATENT AND TRADEMARK OFFICE
CERTIFICATE OF CORRECTION

PATENT NO. : 6,893,822 B2
DATED : May 17, 2005
INVENTOR(S) : Schweitzer et al.

It is certified that error appears in the above-identified patent and that said Letters Patent is hereby corrected as shown below:

Title page,
Item [75], Inventors, delete "Richard R. Anderson, Encinitas, CA (US);", "Michael D. Fiechtner, Poway, CA (US);" and "Jill M. Orwick, San Diego, CA (US);"
delete "Jochen Müller, Diez (DE);" and insert -- Jochen Müller-Ibeler, Diez (DE); --.

Signed and Sealed this

Eighth Day of November, 2005

JON W. DUDAS
*Director of the United States Patent and Trademark Office*